United States Patent
Woo et al.

(10) Patent No.: US 9,719,095 B2
(45) Date of Patent: Aug. 1, 2017

(54) VECTORS AND STRAINS FOR PRODUCING MYRCENE AND METHOD OF PRODUCING MYRCENE USING THE SAME

(71) Applicant: KOREA INSTITUTE OF SCIENCE AND TECHNOLOGY, Seoul (KR)

(72) Inventors: Han Min Woo, Seoul (KR); Eun Mi Kim, Seoul (KR); Youngsoon Um, Seoul (KR); Gyeongtaek Gong, Seoul (KR); Sun Mi Lee, Seoul (KR); Yunje Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 6 days.

(21) Appl. No.: 14/950,425

(22) Filed: Nov. 24, 2015

(65) Prior Publication Data

US 2017/0009240 A1 Jan. 12, 2017

(30) Foreign Application Priority Data

Jul. 8, 2015 (KR) .......................... 10-2015-0097250

(51) Int. Cl.
| | | |
|---|---|---|
| *C12N 15/52* | (2006.01) | |
| *C12N 15/72* | (2006.01) | |
| *C12N 15/71* | (2006.01) | |
| *C12N 9/10* | (2006.01) | |
| *C12N 9/88* | (2006.01) | |
| *C12N 9/04* | (2006.01) | |
| *C12N 9/12* | (2006.01) | |
| *C12N 9/90* | (2006.01) | |
| *C12N 15/70* | (2006.01) | |

(52) U.S. Cl.
CPC .......... *C12N 15/52* (2013.01); *C12N 9/0006* (2013.01); *C12N 9/1029* (2013.01); *C12N 9/1085* (2013.01); *C12N 9/1205* (2013.01); *C12N 9/1229* (2013.01); *C12N 9/88* (2013.01); *C12N 9/90* (2013.01); *C12N 15/70* (2013.01); *C12N 15/71* (2013.01); *C12N 15/72* (2013.01); *C12Y 101/01034* (2013.01); *C12Y 203/01026* (2013.01); *C12Y 205/01* (2013.01); *C12Y 207/01036* (2013.01); *C12Y 207/04002* (2013.01); *C12Y 401/01033* (2013.01); *C12Y 401/03* (2013.01); *C12Y 503/03002* (2013.01)

(58) Field of Classification Search
CPC .......... C12P 5/07; C12N 15/52; C12N 15/63; C12N 15/70
See application file for complete search history.

(56) References Cited

U.S. PATENT DOCUMENTS

| | | | | |
|---|---|---|---|---|
| 7,659,097 B2 * | 2/2010 | Renninger | .............. | C12P 5/007 435/128 |
| 8,415,136 B1 * | 4/2013 | Gardner | ............... | C12N 9/0006 435/254.2 |
| 8,889,383 B2 * | 11/2014 | Beck | .................... | C12N 9/0006 435/146 |
| 2010/0311065 A1 * | 12/2010 | Ubersax | ................. | C12N 15/52 435/6.14 |
| 2012/0288891 A1 * | 11/2012 | Meadows | ............... | C12P 19/62 435/53 |

FOREIGN PATENT DOCUMENTS

KR 10-2007-0103100 A 10/2007

OTHER PUBLICATIONS

Kim et al. Apr. 24, 2015; Microbial synthesis of myrcene by metabolically engineered *Escherichia coli*. Journal of Agriculture and Food Chemistry. 63: 4605-4612.*

Fischbach, Rebort J., Wolfgang Zimmer, and Jörg-Peter Schnitzler. "Isolation and Functional analysis of a cDNA encoding a myrcene synthase from holm oak (*Quercus ilex* L.)." *European Journal of Biochemistry* 268.21 (2001): 5633-5638.

Stolle, A., W. Bonrath, and B. Ondruschka. "Kinetic and mechanistic aspects of myrcene productions via thermal-induced β-pinene rearrangement." Journal of Analytical and Applied Pyrolysis 83.1 (2008): 26-36.

Sarria, Stephen, et al. "Microbial synthesis of pinen." *ACS synthetic biology* 3.7 (2014): 466-475.

Taek Soon, Lee, et al., "BglBrick vectors and datasheets: A synthetic biology platform for gene expression," *Journal of Biological Engineering*, vol. 5, No. 12, 2011, pp. 1-14.

* cited by examiner

*Primary Examiner* — Karen Cochrane Carlson
(74) *Attorney, Agent, or Firm* — NSIP Law

(57) ABSTRACT

Disclosed herein are an expression vector capable of expressing myrcene, an *Escherichia coli* strain transformed with the vector and having improved capability of producing myrcene and a method for producing myrcene and a method for recycling glycerol using the same. In an aspect, the transformed *Escherichia coli* strain of the present disclosure can produce myrcene with high purity on a large scale using glycerol or glucose as a carbon source. Also, the *Escherichia coli* strain of the present disclosure is economical and environment-friendly because it can produce high value-added myrcene using waste glycerol as a carbon source. In addition, the strongly volatile myrcene can be produced and isolated at the same time.

17 Claims, 47 Drawing Sheets

FIG. 1B

BUDAPEST TREATY ON THE INTERNATIONAL RECOGNITION OF THE DEPOSIT
OF MICROORGANISMS FOR THE PURPOSE OF PATENT PROCEDURE

INTERNATIONAL FORM

RECEIPT IN THE CASE OF AN ORIGINAL DEPOSIT
issued pursuant to Rule 7.1

TO : WOO, Han Min
Korea Institute of Science and Technology
5 Hwarang-ro, 14-gil, Seongbuk-gu, Seoul 136-791
Republic of Korea

| I. IDENTIFICATION OF THE MICROORGANISM ||
|---|---|
| Identification reference given by the DEPOSITOR:<br><br>*Escherichia coli* Ec-pM2/pM(Qi) | Accession number given by the INTERNATIONAL DEPOSITARY AUTHORITY:<br><br>KCTC 12851BP |

| II. SCIENTIFIC DESCRIPTION AND/OR PROPOSED TAXONOMIC DESIGNATION |
|---|
| The microorganism identified under I above was accompanied by:<br>[ x ] a scientific description<br>[   ] a proposed taxonomic designation<br>(Mark with a cross where applicable) |

| III. RECEIPT AND ACCEPTANCE |
|---|
| This International Depositary Authority accepts the microorganism identified under I above, which was received by it on June 23, 2015. |

| IV. RECEIPT OF REQUEST FOR CONVERSION |
|---|
| The microorganism identified under I above was received by this International Depositary Authority on            and a request to convert the original deposit to a deposit under the Budapest Treaty was received by it on |

| V. INTERNATIONAL DEPOSITARY AUTHORITY ||
|---|---|
| Name: Korean Collection for Type Cultures<br><br>Address: Korea Research Institute of Bioscience and Biotechnology (KRIBB)<br>125 Gwahak-ro, Yuseong-gu,<br>Daejeon 305-806<br>Republic of Korea | Signature(s) of person(s) having the power to represent the International Depositary Authority of authorized official(s):<br><br>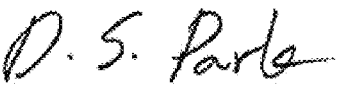<br><br>PARK, Doo Sang, Director<br>Date: June 24 2015 |

FIG. 9

```
atgaagaactgtgtgattgtttctgcggtccgcacggcgatcggcagctttaacggctctttagcgagcacctct
gcaatcgatctgggtgcgacggtcattaaggccgccattgaacgcgccaaaatcgacagccagcacgttgatgag
gtgatcatgggcaatgtgttacaagccggcctgggtcaaaaccagcgcgtcaagcactgttaaaatctggtctg
gcgagaccgtgtgtggcttcaccgtcaataaggtttgcggctctggcctgaagagcgtggccctggcagcacaa
gcgattcaagccggtcaggcacaaagcatcgttgcgggtggcatggagaacatgtctctggcgccgtacttatta
gatgccaaagcccgcagcggttatcgcctgggcgatggtcaggtgtacgacgtcatcttacgcgatggcttaatg
tgcgcgacccacggttaccacatgggtattacggccgaaaacgtggcgaaagaatacggcattacgcgcgagatg
caggatgaattagcactgcactctcagcgcaaagcagcagccgcgatcgagtctggtcgtttacggcggaaatc
gtgccagttaacgtggtcacgcgcaagaagacgttcgttttcagccaggacgagttcccgaaggcaaacagcacc
gcggaggccttaggtgccttacgcccagcctttgacaaagcgggcacggtcacgcgcggtaatgcgagcggcatc
aatgatggtgcagcggcactggtcatcatggaagagagcgccgcattagcagcgggtctgacccccattagcgcgc
attaaatcttatgccagcggcggcgtcccaccagccctgatgggcatgggtccggtcccagccacgcaaaaagcc
ctgcaattagcgggcctgcaactggccgacattgatctgatcgaggcgaacgaggcgtttgcagcgcagttcctg
gcggtgggtaagaatctgggcttcgacagcgagaaagtcaatgtgaacggtggcgcgattgcgttaggccatccg
attggtgcaagcggcgcacgcatcttagtgacgttactgcacgccatgcaggcacgcgacaagaccttaggcctg
gcgaccttatgtattggtggcggtcaaggtatcgccatggtgatcgaacgcctgaactga
```

FIG. 10

```
atgaaactgagcaccaagctgtgctggtgtggcatcaagggtcgcctgcgcccacaaaagcagcaacagctgcac
aacacgaacctgcaaatgaccgagctgaaaaagcagaagacggccgagcaaaagacccgcccgcagaacgttggc
atcaagggcatccagatttatatcccgacgcagtgtgtcaaccaatctgagctggagaaattcgatggcgtcagc
cagggtaagtacaccatcggcctgggccagaccaacatgagcttcgtgaacgaccgtgaggacatctattctatg
agcctgacggtgctgtctaagctgatcaagagctacaacatcgacacgaataagatcggtcgtctggaggtgggt
acggagacgctgattgacaagagcaaaagcgtgaagtctgtcttaatgcagctgttcggcgagaacacggatgtc
gagggtatcgacacccctgaacgcgtgttacggcggcaccaacgcactgttcaatagcctgaactggattgagagc
aacgcctgggatggccgcgatgcgatcgtcgtgtgcggcgatatcgccatctatgacaagggtgcggcacgtccg
accggcggtgcaggcaccgttgcgatgtggattggcccggacgcaccaattgtcttcgattctgtccgcgcgtct
tacatggagcacgcctacgacttttacaagccggacttcacgagcgaataccgtacgtggacggccacttctct
ctgacctgctatgtgaaggcgctggaccaggtttataagtcttatagcaaaaaggcgatttctaagggcctggtc
agcgaccggcaggcagcgacgccctgaacgtgctgaagtatttcgactacaacgtgttccatgtcccgacctgc
aaattagtgaccaaatcttatggccgctgttatataatgatttccgtgccaaccgcagctgttccggaggtt
gacgccgagctggcgacgcgtgattacgacgagagcctgaccgacaagaacatcgagaagaccttcgtcaacgtc
gcgaagccgttccacaaagagcgtgtggcccaaagcctgatcgtccgaccaacacgggcaacatgtataccgcg
tctgtctacgcggcattcgcgagcctgctgaattacgtcggttctgacgacctgcagggcaagcgcgttggcctg
ttcagctacggtagcggcttagcggccagcctgtatagctgcaaaattgtcggcgacgtccagcacatcatcaag
gagctggacatcaccaacaagctggcgaagcgcatcaccgagacgccgaaagattacgaggcagcgatcgagtta
cgcgagaatgcgcatctgaagaagaacttcaagccgcaaggtagcatcgagcacctgcagagcggcgtctactac
ctgacgaacattgacgacaagttccgccgttcttatgacgtcaaaaagtaa
```

FIG. 11

```
atggtgctgacgaacaaaaccgtcattagcggcagcaaggtgaagtctctgagcagcgcccaaagctctagcagc
ggcccgtctagcagcagcgaggaggacgacagccgtgacattgagtctctggacaagaagatccgcccgctggag
gagttagaggccctgctgagcagcggcaacaccaagcagctgaagaacaaggaagttgcagcgctggtgatccac
ggtaagctgccactgtatgcgctggaaaagaaactgggcgatacgacgcgtgcggtcgcggtgcgtcgcaaagcc
ttaagcatcttagcggaggcccggtgttagccagcgaccgcctgccgtacaagaactacgactacgaccgcgtg
tttggcgcgtgctgcgagaatgtcattggctacatgccgttaccggttggtgtgatcggccgctggtcattgat
ggcacgagctatcacattccaatggcgaccacggaaggttgcttagtcgccagcgccatgcgtggctgtaaggcg
attaacgccggcggtggcgcgacgaccgtgttaaccaaggatggtatgacgcgcggtccggtcgtccgcttcca
acgctgaagcgcagcggcgcgtgtaagatttggctggattctgaggagggccaaaacgcgatcaagaaagccttc
aactctacgagccgtttcgcgcgtttacagcatatccagacctgcctggccggcgacctgctgttcatgcgcttc
cgcaccaccacgggcgatgcgatgggcatgaacatgatcagcaagggcgtcgaatatagcctgaaacaaatggtg
gaagaatatggctgggaggacatggaggttgtctctgtgagcggcaactattgcaccgacaagaagccggcagcc
attaactggattgagggtcgcggcaaaagcgtcgtggcagaagcgaccatcccaggcgacgtggtccgtaaggtt
ctgaagagcgacgtcagcgccctggttgagttaaatatcgcgaaaaacctggtcggcagcgcgatggcgggcagc
gtgggtggctttaacgcacatgcagcgaatctggttacggcggttttcttagccttaggtcaggacccagcccaa
aatgtcgagagcagcaactgcattaccttaatgaaagaggttgacggtgacctgcgcatcagcgtttctatgccg
tctatcgaggtcggcacgatcggcggcggcaccgttttagaaccgcaaggtgcgatgctggatctgctgggcgtg
cgcggcccacatgcaacggcccaggcaccaatgcccgccaactggcccgtatcgtggcctgcgcggttctggcg
ggtgagctgagcctgtgcgccgcattagccgcgggccatttagttcaatctcacatgacccacaaccgcaagccg
gcagaaccaaccaagccaaataacctggacgcaaccgacattaaccgtctgaaggatggcagcgtcacgtgcatt
aaaagctga
```

FIG. 12

```
atgtctctgccattcctgacgtctgcgccaggtaaggtgatcatcttcggcgagcactctgcggtgtacaataag
ccggccgtcgccgcctctgtgtctgcgttacgcacctacctgctgatcagcgaatcttctgcaccggacacgatc
gagctggactttccggacatcagcttcaaccacaagtggagcatcaacgacttcaacgcgatcacggaggaccag
gtgaacagccaaaagctggccaaagcccagcaagcaacgacggtctgtctcaggagctggtgtctctgctggac
ccgctgttagcgcagttaagcgagagcttccattaccacgccgcgttctgcttcctgtacatgttcgtttgcctg
tgcccgcacgcaaagaacatcaagttcagcctgaagagcacgctgccgattggcgcaggcttaggctctagcgca
tctatcagcgtgagcctggcgctggcgatggcctatctgggtggcctgattggcagcaacgacctggagaaactg
agcgaaaacgacaagcacatcgtgaaccagtgggcctttatcggcgagaagtgcattcatggcacccgagcggc
attgacaacgcagttgccacgtatggcaacgccctgctgttcgagaaagacagccacaacggcacgatcaacacg
aacaacttcaagttcctggacgacttcccggcgatcccgatgattctgacctacacccgtatcccacgcagcacc
aaggatttagtcgcccgcgtgcgtgttttagtcaccgaaaagttcccggaggtgatgaagccgatcctggacgcg
atgggcgagtgcgcgctgcaggtctggagatcatgaccaagctgagcaagtgcaagggcaccgacgatgaggcg
gtggagaccaacaatgagctgtacgagcagctgctggagctgatccgtatcaatcacggcctgctggtctctatc
ggtgtgtctcaccccgggcctggaactgatcaaaaacctgagcgacgacctgcgcattggctctacgaaattaacg
ggtgcaggtggcggtggctgctctttaacgctgctgcgccgtgacattacgcaggagcaaatcgacagcttcaag
aagaagctgcaggacgacttcagctacgagacgttcgagacggacctgggcggcacgggctgttgcctgctgagc
gccaaaaatctgaacaaggacctgaagatcaaagcctggtgttccagctgttcgaaaacaagacgaccacgaag
cagcagatcgacgacctgttactgccgggtaacaccaatctgccgtggacgtcttaa
```

FIG. 13

```
atgagcgaattacgtgcattcagcgcgccaggtaaggcactgctggccggtggctacctggtgttagacaccaag
tacgaggcgttcgtcgtcggcttatctgcccgtatgcatgcagttgcccaccgtatggtagcctgcaggctct
gacaagttcgaagtgcgtgtgaagagcaagcagttcaaggacggcgagtggctgtaccacattagcccaaagagc
ggcttcatcccggttagcattggtggcagcaagaacccatttatcgagaaggtcattgccaacgtcttcagctac
ttcaagccgaatatggacgattactgcaaccgcaacctgttcgtcatcgacattttcagcgacgacgcgtaccac
agccaagaggactctgttacggagcatcgtggtaaccgcgcctgagcttccacagccatcgcattgaggaggtg
ccgaagacgggtctggttctagcgccggtttagttaccgtcttaacgacggcgttagcgagcttcttcgtgagc
gacctggagaacaacgtggacaagtaccgcgaagtgattcataacctggcgcaggtggcacattgtcaggccaa
ggtaagattggctctggttttgatgtggcagcggccgcctatggctctatccgctatcgccgcttccgccggcc
ctgatcagcaatctgccggacatcggctctgcgacgtatggtagcaaactggcgcatctggtggacgaagaagac
tggaacatcaccattaagtctaatcacctgccgagcggcttaacgttatggatgggcgatatcaagaacggcagc
gaaacggttaagctggtgcagaaagtgaaaaactggtacgacagccacatgccggaaagcctgaagatttacacg
gagctggaccacgccaatagccgtttcatggatggtctgagcaagctggaccgcctgcacgaaacccacgacgac
tacagcgaccaaatcttcgagagcctggagcgcaatgactgcacctgccagaagtaccggagatcacggaggtc
ccgcgatgccgtggcaacgattcgccgtagcttccgcaaaattacgaaggagagcggcgcggatatcgaaccaccg
gtccagacgtctctgctggacgactgtcaaaccttaaagggcgtgttaacgtgcctgattccgggcgcgggtggt
tacgacgccattgccgtcatcacgaaacaggacgtcgatctgcgcgcacaaacggcaacgacaaacgtttcagc
aaagtccaatggctggatgttacgcaggccgactggggtgttcgcaaggagaaggacccggaaacgtatctggat
aagtga
```

FIG. 14

```
atgaccgtttacacagcatccgttaccgcacccgtcaacatcgcaacccttaagtattgggggaaaagggacacg
aagttgaatctgcccaccaattcgtccatatcagtgactttatcgcaagatgacctcagaacgttgacctctgcg
gctactgcacctgagtttgaacgcgacactttgtggttaaatggagaaccacacagcatcgacaatgaaagaact
caaaattgtctgcgcgacctacgccaattaagaaaggaaatggaatcgaaggacgcctcattgcccacattatct
caatggaaactccacattgtctccgaaaataactttcctacagcagctggtttagcttcctccgctgctggcttt
gctgcattggtctctgcaattgctaagttataccaattaccacagtcaacttcagaaatatctagaatagcaaga
aagggtctggttcagcttgtagatcgttgtttggcggatacgtggcctgggaaatgggaaaagctgaagatggt
catgattccatggcagtacaaatcgcagacagctctgactggcctcagatgaaagcttgtgtcctagttgtcagc
gatattaaaaaggatgtgagttccactcagggtatgcaattgaccgtggcaacctccgaactatttaaagaaaga
attgaacatgtcgtaccaaagagatttgaagtcatgcgtaaagccattgttgaaaaagatttcgccaccttgca
aaggaaacaatgatggattccaactctttccatgccacatgtttggactcttcctccaatattctacatgaat
gacacttccaagcgtatcatcagttggtgccacaccattaatcagttttacggagaaacaatcgttgcatacacg
tttgatgcaggtccaaatgctgtgttgtactacttagctgaaaatgagtcgaaactctttgcatttatctataaa
ttgtttggctctgttcctggatgggacaagaaatttactactgagcagcttgaggctttcaaccatcaatttgaa
tcatctaacttttactgcacgtgaattggatcttgagttgcaaaaggatgttgccagagtgattttaactcaagtc
ggttcaggcccacaagaaacaaacgaatctttgattgacgcaaagactggtctaccaaaggaataa
```

FIG. 15

```
atgcaaacggaacacgtcattttattgaatgcacagggagttcccacgggtacgctggaaaagtatgccgcacac
acggcagacacccgcttacatctcgcgttctccagttggctgtttaatgccaaaggacaattattagttacccgc
cgcgcactgagcaaaaagcatggcctggcgtgtggactaactcggtttgtgggcacccacaactgggagaaagc
aacgaagacgcagtgatccgccgttgccgttatgagcttggcgtggaaattacgcctcctgaatctatctatcct
gactttcgctaccgcgccaccgatccgagtggcattgtggaaaatgaagtgtgtccggtatttgccgcacgcacc
actagtgcgttacagatcaatgatgatgaagtgatggattatcaatggtgtgatttagcagatgtattacacggt
attgatgccacgccgtgggcgttcagtccgtggatggtgatgcaggcgacaaatcgcgaagccagaaaacgatta
tctgcatttacccagcttaaataa
```

FIG. 16

```
ATGGTGGAATTTGATTTTAACAAATATATGGATAGCAAAGCGATGACCGTGAACGAAGCGCTGAACAAAGCGATT
CCGCTGCGCTATCCGCAGAAAATTTATGAAAGCATGCGCTATAGCCTGCTGGCGGGCGGCAAACGCGTGCGCCCG
GTGCTGTGCATTGCGGCGTGCGAACTGGTGGGCGGCACCGAAGAACTGGCGATTCCGACCGCGTGCGCGATTGAA
ATGATTCATACCATGAGCCTGATGCATGATGATCTGCCGTGCATTGATAACGATGATCTGCGCCGCGGCAAACCG
ACCAACCATAAAATTTTTGGCGAAGATACCGCGGTGACCGCGGGCAACGCGCTGCATAGCTATGCGTTTGAACAT
ATTGCGGTGAGCACCAGCAAAACCGTGGGCGCGGATCGCATTCTGCGCATGGTGAGCGAACTGGGCCGCGCGACC
GGCAGCGAAGGCGTGATGGGCGGCCAGATGGTGGATATTGCGAGCGAAGGCGATCCGAGCATTGATCTGCAGACC
CTGGAATGGATTCATATTCATAAAACCGCGATGCTGCTGGAATGCAGCGTGGTGTGCGGCGCGATTATTGGCGGC
GCGAGCGAAATTGTGATTGAACGCGCGCGCCGCTATGCGCGCTGCGTGGGCCTGCTGTTTCAGGTGGTGGATGAT
ATTCTGGATGTGACCAAAAGCAGCGATGAACTGGGCAAAACCGCGGGCAAAGATTTAATTAGCGATAAAGCGACC
TATCCGAAACTGATGGGCCTGGAAAAAGCGAAAGAATTTAGCGATGAACTGCTGAACCGCGCGAAAGGCGAACTG
AGCTGCTTTGATCCGGTGAAAGCGGCGCCGCTGCTGGGCCTGGCGGATTATGTGGCGTTTCGCCAGAACTAA
```

FIG. 17

```
ATGCGTCGTAGCGCAAATTATCAGCCGAGCATTTGGAATCATGATTATATTGAAAGCCTGCGTATTGAATATGTT
GGTGAAACCTGTACCCGTCAGATTAATGTTCTGAAAGAACAGGTTCGTATGATGCTGCATAAAGTTGTTAATCCG
CTGGAACAGCTGGAACTGATTGAAATTCTGCAGCGTCTGGGTCTGAGCTATCATTTTGAAGAAGAAATTAAACGT
ATTCTGGATGGTGTTTATAATAATGATCATGGTGGTGATACCTGGAAAGCAGAAAATCTGTATGCAACCGCACTG
AAATTCGTCTGCTGCGTCAGCATGGTTATAGCGTTAGCCAGGAAGTTTTTAATAGCTTTAAAGATGAACGTGGT
AGCTTTAAAGCATGTCTGTGTGAAGATACCAAAGGTATGCTGAGCCTGTATGAAGCAAGCTTTTTTCTGATTGAA
GGTGAAAATATTCTGGAAGAAGCACGTGATTTTAGCACCAAACATCTGGAAGAATATGTTAAACAGAATAAAGAA
AAAAATCTGGCAACCCTGGTTAATCATAGCCTGGAATTTCCGCTGCATTGGCGTATGCCGCGTCTGGAAGCACGT
TGGTTTATTAATATTTATCGTCATAATCAGGATGTTAATCCGATTCTGCTGGAATTTGCAGAACTGGATTTTAAT
ATTGTTCAGGCAGCACATCAGGCAGATTTAAAACAGGTTAGCACCTGGTGGAAAAGCACCGGTCTGGTTGAAAAT
CTGAGCTTTGCACGTGATCGTCCGGTTGAAAATTTTTTTTGGACCGTTGGTCTGATTTTTCAGCCGCAGTTTGGT
TATTGTCGTCGTATGTTTACCAAAGTTTTTGCACTGATTACCACCATTGATGATGTTTATGATGTTTATGGTACC
CTGGATGAACTGGAACTGTTTACCGATGTTGTTGAACGTTGGGATATTAATGCAATGGATCAGCTGCCGGATTAT
ATGAAAATTTGTTTTCTGACCCTGCATAATAGCGTTAATGAAATGGCACTGGATACCATGAAAGAACAGCGTTTT
CATATTATTAAATATCTGAAAAAAGCATGGGTTGATCTGTGTCGTTATTATCTGGTTGAAGCAAAATGGTATAGC
AATAAATATCGTCCGAGCCTGCAGGAATATATTGAAAATGCATGGATTAGCATTGGTGCACCGACCATTCTGGTT
CATGCATATTTTTTTGTTACCAATCCGATTACCAAAGAAGCACTGGATTGTCTGGAAGAATATCCGAATATTATT
CGTTGGAGCAGCATTATTGCACGTCTGGCAGATGATCTGGGTACCAGCACCGATGAACTGAAACGTGGTGATGTT
CCGAAAGCAATTCAGTGTTATATGAATGAAACCGGTGCAAGCGAAGAAGGTGCACGTGAATATATTAAATATCTG
ATTAGCGCAACCTGGAAAAAAATGAATAAAGATCGTGCAGCAAGCAGCCCGTTTAGCCATATTTTTATTGAAATT
GCACTGAATCTGGCACGTATGGCACAGTGTCTGTATCAGCATGGTGATGGTCATGGTCTGGGTAATCGTGAAACC
AAAGATCGTATTCTGAGCCTGCTGATTCAGCCGATTCCGCTGAATAAAGATTAA
```

FIG. 18A gacgtcggtgcctaatgagtgagctaacttacattaattgcgttgcgctcactgcccgctttccagtcgggaaac
ctgtcgtgccagctgcattaatgaatcggccaacgcgcggggagaggcggtttgcgtattgggcgccagggtggt
ttttcttttcaccagtgagacgggcaacagctgattgcccttcaccgcctggccctgagagagttgcagcaagcg
gtccacgctggtttgccccagcaggcgaaaatcctgtttgatggtggttaacggcgggatataacatgagctgtc
tcggtatcgtcgtatcccactaccgagatgtcgcaccaacgcgcagcccggactcggtaatggcgcgcattgc
gcccagcgccatctgatcgttggcaaccagcatcgcagtgggaacgatgccctcattcagcatttgcatggtttg
ttgaaaaccggacatggcactccagtcgccttccgttccgctatcggctgaatttgattgcgagtgagatattt
atgccagccagccagacgcagacgcgccgagacagaacttaatgggcccgctaacagcgcgatttgctggtgacc
caatgcgaccagatgctccacgcccagtcgcgtaccgtcttcatgggagaaaataatactgttgatgggtgtctg
gtcagagacatcaagaaataacgccggaacattagtgcaggcagcttccacagcaatggcatcctggtcatccag
cggatagttaatgatcagcccactgacgcgttgcgcgagaagattgtgcaccgccgctttacaggcttcgacgcc
gcttcgttctaccatcgacaccaccacgctggcacccagttgatcggcgcgagatttaatcgccgcgacaatttg
cgacggcgcgtgcagggccagactggaggtggcaacgccaatcagcaacgactgtttgcccgccagttgttgtgc
cacgcggtgggaatgtaattcagctccgccatcgccgcttccactttttcccgcgttttcgcagaaacgtggct
ggcctggttcaccacgcgggaaacggtctgataagagacaccggcatactctgcgacatcgtataacgttactgg
tttcacattcaccacccctgaattgactctcttccgggcgctatcatgccataccgcgaaaggttttgcgccattc
gatggtgtccgggatctcgacgctctcccttatgcgactcctgcattaggaagcagcccagtagtaggttgaggc
cgttgagcaccgccgccgcaaggaatggtgcatgcaaggagatggcgccaacagtcccccggccacgggcctg
ccaccataccacgccgaaacaagcgctcatgagcccgaagtggcgagcccgatcttccccatcggtgatgtcgg
cgatataggcgcagcaaccgcacctgtggcgccggtgatgccggccacgatgcgtccggcgtagaggatcgaga
tcgtttaggcacccaggctttacactttatgcttccggctcgtataatgtgtggaattgtgagcggataacaat
ttcagaattcaaaagatctaaaggaggccatcctggccatgaagaactgtgtgattgtttctgcggtccgcacgg
cgatcggcagctttaacgctctttagcgagcacctctgcaatcgatctgggtgcgacggtcattaaggccgcca
ttgaacgcgccaaaatcgacagccagcacgttgatgaggtgatcatgggcaatgtgttacaagccggcctgggtc
aaaacccagcgcgtcaagcactgttaaaatctggtctggccgagaccgtgtgtggcttcaccgtcaataaggttt
gcggctctggcctgaagagcgtggccctggcagcacaagcgattcaagccggtcaggcacaaagcatcgttgcgg
gtggcatggagaacatgtctctggcgccgtacttattagatgccaaagcccgcagcggttatcgcctgggcgatg
gtcaggtgtacgacgtcatcttacgcgatggcttaatgtgcgcgacccacggttaccacatgggtattacggcg
aaaacgtggcgaaagaatacggcattacgcgcgagatgcaggatgaattagcactgcactctcagcgcaaagcag
cagccgcgatcgagtctggtgcgtttacggcgaaatcgtgccagttaacgtggtcacgcgcaagaagacgttcg
ttttcagccaggacgagttcccgaaggcaaacagcaccgcggaggccttaggtgccttacgccagcctttgaca
aagcgggcacggtcaccgccggtaatgcgagcggcatcaatgatggtgcagcggcactggtcatcatggaagaga
gcgccgcattagcagcgggtctgaccccattagcgcgcattaaatcttatgccagcggcggcgtcccaccagccc
tgatgggcatgggtccggtccagccacgcaaaaagccctgcaattagcgggcctgcaactggccgacattgatc
tgatcgaggcgaacgaggcgtttgcagcgcagttcctggcggtgggtaagaatctgggcttcgacagcgagaaag

FIG. 18B

```
tcaatgtgaacggtggcgcgattgcgttaggccatccgattggtgcaagcggcgcacgcatcttagtgacgttac
tgcacgccatgcaggcacgcgacaagaccttaggcctggcgacccttatgtattggtggcggtcaaggtatcgcca
tggtgatcgaacgcctgaactgatgaaggaggaaagcaaaatgaaactgagcaccaagctgtgctggtgtggcat
caagggtcgcctgcgcccacaaaagcagcaacagctgcacaacacgaacctgcaaatgaccgagctgaaaagca
gaagacggccgagcaaaagaccgccgcagaacgttggcatcaagggcatccagatttatatcccgacgcagtg
tgtcaaccaatctgagctggagaaattcgatggcgtcagccagggtaagtacaccatcggcctgggccagaccaa
catgagcttcgtgaacgacgtgaggacatctattctatgagcctgacggtgctgtctaagctgatcaagagcta
caacatcgacacgaataagatcggtcgtctggaggtgggtacggagacgctgattgacaagagcaaaagcgtgaa
gtctgtcttaatgcagctgttcggcgagaacacggatgtcgagggtatcgacaccctgaacgcgtgttacggcgg
caccaacgcactgttcaatagcctgaactggattgagagcaacgcctgggatggccgcgatgcgatcgtcgtgtg
cggcgatatcgccatctatgacaagggtgcggcacgtccgaccggcggtgcaggcaccgttgcgatgtggattgg
cccggacgcaccaattgtcttcgattctgtccgcgcgtcttacatggagcacgcctacgacttttacaagccgga
cttcacgagcgaataccgtacgtggacggccacttctctctgacctgctatgtgaaggcgctggaccaggttta
taagtcttatagcaaaaaggcgatttctaagggcctggtcagcgaccggcaggcagcgacgccctgaacgtgct
gaagtatttcgactacaacgtgttccatgtcccgacctgcaaattagtgaccaaatcttatggccgcctgttata
taatgatttccgtgccaaccgcagctgttcccggaggttgacgccgagctggcgacgcgtgattacgacgagag
cctgaccgacaagaacatcgagaagaccttcgtcaacgtcgcgaagccgttccacaaagagcgtgtggcccaaag
cctgatcgtcccgaccaacacgggcaacatgtatacgcgtctgtctacgcggcattcgcgagcctgctgaatta
cgtcggttctgacgacctgcagggcaagcgcgttggcctgttcagctacggtagcggcttagcggccagcctgta
tagctgcaaaattgtcggcgacgtccagcacatcatcaaggagctggacatcaccaacaagctggcgaagcgcat
caccgagacgccgaaagattacgaggcagcgatcgagttacgcgagaatgcgcatctgaagaagaacttcaagcc
gcaaggtagcatcgagcacctgcagagcggcgtctactacctgacgaacattgacgacaagttccgccgttctta
tgacgtcaaaaagtaactagtaggaggaaaacatcatggtgctgacgaacaaaaaccgtcattagcggcagcaagg
tgaagtctctgagcagcgcccaaagctctagcagcggcccgtctagcagcagcgaggaggacgacagccgtgaca
ttgagtctctggacaagaagatccgccgctggaggagttagaggccctgctgagcagcggcaacaccaagcagc
tgaagaacaaggaagttgcagcgctggtgatccacggtaagctgccactgtatgcgctggaaaagaaactgggcg
atacgacgcgtcggtcgcggtgcgtcgcaaagccttaagcatcttagcggaggcccggtgttagccagcgacc
gcctgcgtacaagaactacgactacgaccgcgtgtttggcgcgtgctgcgagaatgtcattggctacatgccgt
taccggttggtgtgatcggcccgctggtcattgatgcacgagctatcacattccaatggcgaccacggaaggtt
gcttagtcgccagcgccatgcgtggctgtaaggcgattaacgccggcggtggcgcgacgaccgtgttaaccaagg
atggtatgacgcgcggtccggtcgtccgcttcccaacgctgaagcgcagcggcgcgtgtaagatttggctggatt
ctgaggagggccaaaacgcgatcaagaaagccttcaactctacgagccgtttcgcgcgtttacagcatatccaga
cctgcctggccggcgacctgctgttcatgcgcttccgcaccaccacgggcgatgcgatgggcatgaacatgatca
gcaagggcgtcgaatatagcctgaaacaaatggtggaagaatatggctgggaggacatggaggttgtctctgtga
gcggcaactattgcaccgacaagaagccggcagccattaactggattgagggtcgcggcaaaagcgtcgtggcag
aagcgaccatcccaggcgacgtggtccgtaaggttctgaagagcgacgtcagcgccctgttgagttaaatatcg
cgaaaaacctggtcggcagcgcgatggcgggcagcgtgggtggctttaacgcacatgcagcgaatctggttacgg
cggttttcttagccttaggtcaggacccagcccaaaatgtcgagagcagcaactgcattaccttaatgaaagagg
```

FIG. 18C

```
ttgacggtgacctgcgcatcagcgtttctatgccgtctatcgaggtcggcacgatcggcggcggcaccgttttag
aaccgcaaggtgcgatgctggatctgctgggcgtgcgcggccacatgcaacggccccaggcaccaatgcccgcc
aactggcccgtatcgtggcctgcgcggttctggcgggtgagctgagcctgtgcgccgcattagccgcgggccatt
tagttcaatctcacatgacccacaaccgcaagccggcagaaccaaccaagccaaataacctggacgcaaccgaca
ttaaccgtctgaaggatggcagcgtcacgtgcattaaaagctgaggatctaggaggaaataaccatgtctctgcc
attcctgacgtctgcgccaggtaaggtgatcatcttcggcgagcactctgcggtgtacaataagccggccgtcgc
cgcctctgtgtctgcgttacgcacctacctgctgatcagcgaatcttctgcaccggacacgatcgagctggactt
tccggacatcagcttcaaccacaagtggagcatcaacgacttcaacgcgatcacggaggaccaggtgaacagcca
aaagctggccaaagccagcaagcaaccgacggtctgtctcaggagctggtgtctctgctggacccgctgttagc
gcagttaagcgagagcttccattaccacgccgcgttctgcttcctgtacatgttcgtttgcctgtgccccgcacgc
aaagaacatcaagttcagcctgaagagcacgctgccgattggcgcaggcttaggctctagcgcatctatcagcgt
gagcctggcgctggcgatggcctatctgggtggcctgattggcagcaacgacctggagaaactgagcgaaaacga
caagcacatcgtgaaccagtgggcctttatcggcgagaagtgcattcatggcaccccgagcggcattgacaacgc
agttgccacgtatggcaacgccctgctgttcgagaaagacagccacaacggcacgatcaacacgaacaacttcaa
gttcctggacgacttcccggcgatcccgatgattctgacctacacccgtatcccacgcagcaccaaggatttagt
cgcccgcgtgcgtgttttagtcaccgaaaagttcccggaggtgatgaagccgatcctggacgcgatgggcgagtg
cgcgctgcagggtctggagatcatgaccaagctgagcaagtgcaagggcaccgacgatgaggcggtggagaccaa
caatgagctgtacgagcagctgctggagctgatccgtatcaatcacggcctgctggtctctatcggtgtgtctca
cccggggcctggaactgatcaaaaacctgagcgacgacctgcgcattggctctacgaaattaacgggtgcaggtgg
cggtggctgctctttaacgctgctgcgccgtgacattacgcaggagcaaatcgacagcttcaagaagaagctgca
ggacgacttcagctacgagacgttcgagacggacctgggcggcacgggctgttgcctgctgagcgccaaaaatct
gaacaaggacctgaagatcaaaagcctggtgttccagctgttcgaaaacaagacgaccacgaagcagcagatcga
cgacctgttactgccgggtaacaccaatctgccgtggacgtcttaaggatctaggagggagatcatatgagcgaa
ttacgtgcattcagcgcgccaggtaaggcactgctggccggtggctacctggtgttagacaccaagtacgaggcg
ttcgtcgtcggcttatctgcccgtatgcatgcagttgcccacccgtatggtagcctgcagggctctgacaagttc
gaagtgcgtgtgaagagcaagcagttcaaggacggcgagtggctgtaccacattagcccaaagagcggcttcatc
ccggttagcattggtggcagcaagaacccatttatcgagaaggtcattgccaacgtcttcagctacttcaagccg
aatatggacgattactgcaaccgcaacctgttcgtcatcgacattttcagcgacgacgcgtaccacagccaagag
gactctgttacggagcatcgtggtaaccgccgcctgagcttccacagccatcgcattgaggaggtgccgaagacg
ggtctgggttctagcgccggtttagttacgtcttaacgacggcgttagcgagcttcttcgtgagcgacctggag
aacaacgtggacaagtaccgcgaagtgattcataacctggcgcaggtggcacattgtcaggcccaaggtaagatt
ggctctggttttgatgtggcagcggccgcctatggctctatccgctatcgccgctttccgccggccctgatcagc
aatctgccggacatcggctctgcgacgtatggtagcaaactggcgcatctggtggacgaagaagactggaacatc
accattaagtctaatcacctgccgagcggcttaacgttatggatgggcgatatcaagaacggcagcgaaacggtt
aagctggtgcagaaagtgaaaaactggtacgacagccacatgccggaaagcctgaagatttacacggagctggac
cacgccaatagccgtttcatggatggtctgagcaagctggaccgcctgcacgaaacccacgacgactacagcgac
caaatcttcgagagcctggagcgcaatgactgcacctgccagaagtacccggagatcacggaggtccgcgatgcc
gtggcaacgattcgccgtagcttccgcaaaattacgaaggagagcggcgcggatatcgaaccaccggtccagacg
```

FIG. 18D

```
tctctgctggacgactgtcaaaccttaaagggcgtgttaacgtgcctgattccgggcgcgggtggttacgacgcc
attgccgtcatcacgaaacaggacgtcgatctgcgcgcacaaacggccaacgacaaacgtttcagcaaagtccaa
tggctggatgttacgcaggccgactggggtgttcgcaaggagaaggacccggaaacgtatctggataagtgagga
tctaggaggattatgagatgaccgtttacacagcatccgttaccgcaccgtcaacatcgcaacccttaagtatt
gggggaaaagggacacgaagttgaatctgcccaccaattcgtccatatcagtgactttatcgcaagatgacctca
gaacgttgacctctgcggctactgcacctgagtttgaacgcgacactttgtggttaaatggagaaccacacagca
tcgacaatgaaagaactcaaaattgtctgcgcgacctacgccaattaagaaaggaaatggaatcgaaggacgcct
cattgcccacattatctcaatggaaactccacattgtctccgaaaataactttcctacagcagctggtttagctt
cctccgctgctggctttgctgcattggtctctgcaattgctaagttataccaattaccacagtcaacttcagaaa
tatctagaatagcaagaaaggggtctggttcagcttgtagatcgttgtttggcggatacgtggcctgggaaatgg
gaaagctgaagatggtcatgattccatggcagtacaaatcgcagacagctctgactggcctcagatgaaagctt
gtgtcctagttgtcagcgatattaaaaaggatgtgagttccactcagggtatgcaattgaccgtggcaacctccg
aactatttaaagaaagaattgaacatgtcgtaccaagagatttgaagtcatgcgtaaagccattgttgaaaaag
atttcgccacctttgcaaaggaaacaatgatggattccaactctttccatgccacatgtttggactctttccctc
caatattctacatgaatgacacttccaagcgtatcatcagttggtgccacaccattaatcagttttacggagaaa
caatcgttgcatacacgtttgatgcaggtccaaatgctgtgttgtactacttagctgaaaatgagtcgaaactct
ttgcatttatctataaaattgtttggctctgttcctggatgggacaagaaatttactactgagcagcttgaggctt
tcaaccatcaatttgaatcatctaactttactgcacgtgaattggatcttgagttgcaaaaggatgttgccagag
tgatttttaactcaagtcggttcaggcccacaagaaacaaacgaatctttgattgacgcaaagactggtctaccaa
aggaataaggatctaggaggtaatgataatgcaaacggaacacgtcattttattgaatgcacagggagttcccac
gggtacgctggaaaagtatgccgcacacacggcagacacccgcttacatctcgcgttctccagttggctgtttaa
tgccaaaggacaattattagttaccgccgcgcactgagcaaaaaagcatggcctggcgtgtggactaactcggt
ttgtgggcacccacaactgggagaaagcaacgaagacgcagtgatccgccgttgccgttatgagcttggcgtgga
aattacgcctcctgaatctatctatcctgactttcgctaccgcgccaccgatccgagtggcattgtggaaaatga
agtgtgtccggtatttgccgcacgcaccactagtgcgttacagatcaatgatgatgaagtgatggattatcaatg
gtgtgatttagcagatgtattacacggtattgatgccacgccgtgggcgttcagtccgtggatggtgatgcaggc
gacaaatcgcgaagccagaaaacgattatctgcatttacccagcttaaataaggatccaaactcgagtaaggatc
tccaggcatcaaataaaacgaaaggctcagtcgaaagactgggcctttcgttttatctgttgtttgtcggtgaac
gctctctactagagtcacactggctcaccttcgggtgggcctttctgcgtttatacctagggatatattccgctt
cctgctcactgactcgctacgctcggtcgttcgactgcggcgagcggaaatggcttacgaacggggcggagatt
tcctggaagatgccaggaagatacttaacagggaagtgagagggccgcggcaaagccgttttccataggctccg
ccccctgacaagcatcacgaaatctgacgctcaaatcagtggtggcgaaacccgacaggactataaagatacca
ggcgtttccccctggcggctccctcgtgcgctctcctgttcctgcctttcggtttaccggtgtcattccgctgtt
atggccgcgtttgtctcattccacgcctgacactcagttccgggtaggcagttcgctccaagctggactgtatgc
acgaaccccccgttcagtccgaccgctgcgccttatccggtaactatcgtcttgagtccaacccgaaagacatg
caaaagcaccactggcagcagccactggtaattgatttagaggagttagtcttgaagtcatgcgccggttaaggc
taaactgaaaggacaagttttggtgactgcgctcctccaagccagttacctcggttcaaagagttggtagctcag
agaaccttcgaaaaaccgccctgcaaggcggttttttcgttttcagagcaagagattacgcgcagaccaaaacga
```

FIG. 18E

```
tctcaagaagatcatcttattaatcagataaaatatttctagatttcagtgcaatttatctcttcaaatgtagca
cctgaagtcagccccatacgatataagttgttactagtgcttggattctcaccaataaaaaacgcccggcggcaa
ccgagcgttctgaacaaatccagatggagttctgaggtcattactggatctatcaacaggagtccaagcgagctc
gatatcaaattacgccccgccctgccactcatcgcagtactgttgtaattcattaagcattctgccgacatggaa
gccatcacaaacggcatgatgaacctgaatcgccagcggcatcagcaccttgtcgccttgcgtataatatttgcc
catggtgaaaacgggggcgaagaagttgtccatattggccacgtttaaatcaaaactggtgaaactcacccaggg
attggctgagacgaaaaacatattctcaataaacccctttagggaaataggccaggttttcaccgtaacacgccac
atcttgcgaatatatgtgtagaaactgccggaaatcgtcgtggtattcactccagagcgatgaaaacgtttcagt
ttgctcatggaaaacggtgtaacaagggtgaacactatcccatatcaccagctcaccgtctttcattgccatacg
aaattccggatgagcattcatcaggcgggcaagaatgtgaataaaggccggataaaacttgtgcttattttttctt
tacggtctttaaaaaggccgtaatatccagctgaacggtctggttataggtacattgagcaactgactgaaatgc
ctcaaaatgttctttacgatgccattgggatatatcaacggtggtatatccagtgatttttttctccattttagc
ttccttagctcctgaaaatctcgataactcaaaaaatacgcccggtagtgatcttatttcattatggtgaaagtt
ggaacctcttacgtgccgatcaacgtctcattttcgccagatatc
```

FIG. 19A

```
gacgtcggtgcctaatgagtgagctaacttacattaattgcgttgcgctcactgcccgctttccagtcgggaaac
ctgtcgtgccagctgcattaatgaatcggccaacgcgcggggagaggcggtttgcgtattgggcgccagggtggt
ttttcttttcaccagtgagacgggcaacagctgattgcccttcaccgcctggccctgagagagttgcagcaagcg
gtccacgctggtttgccccagcaggcgaaaatcctgtttgatggtggttaacgcgggatataacatgagctgtc
tteggtatcgtcgtatcccactaccgagatgtccgcaccaacgcgcagcccggactcggtaatggcgcgcattgc
gcccagcgccatctgatcgttggcaaccagcatcgcagtgggaacgatgccctcattcagcatttgcatggtttg
ttgaaaaccggacatggcactccagtcgccttcccgttccgctatcggctgaatttgattgcgagtgagatattt
atgccagccagccagacgcagacgcgccgagacagaacttaatgggcccgctaacagcgcgatttgctggtgacc
caatgcgaccagatgctccacgcccagtcgcgtaccgtcttcatgggagaaaataatactgttgatgggtgtctg
gtcagagacatcaagaaataacgccggaacattagtgcaggcagcttccacagcaatggcatcctggtcatccag
cggatagttaatgatcagccactgacgcgttgcgcgagaagattgtgcaccgccgctttacaggcttcgacgcc
gcttcgttctaccatcgacaccaccacgctggcacccagttgatcggcgcgagatttaatcgcgcgacaatttg
cgacggcgcgtgcagggccagactggaggtggcaacgccaatcagcaacgactgtttgcccgccagttgttgtgc
cacgcggttgggaatgtaattcagctccgccatcgcgcttccacttttttcccgcgtttttcgcagaaacgtggct
ggcctggttcaccacgcgggaaacggtctgataagagacacggcatactctgcgacatcgtataacgttactgg
tttcacattcaccaccctgaattgactctcttccgggcgctatcatgccataccgcgaaaggttttgcgccattc
gatggtgtccgggatctcgacgctctcccttatgcgactcctgcattaggaagcagccagtagtaggttgaggc
cgttgagcaccgccgccgcaaggaatggtgcatgcaaggagatggcgcccaacagtccccggccacgggcctg
ccaccatacccacgccgaaacaagcgctcatgagccgaagtgcgagccgatcttcccatcggtgatgtcgg
cgatataggcgccagcaacgcacctgtggcgccggtgatgccggccacgatgcgtccggcgtagaggatcgaga
tcgtttaggcacccaggctttacactttatgcttccggctcgtataatgtgtggaattgtgagcggataacaat
ttcagaattcaaaagatctaaaggaggccatcctggccatgaagaactgtgtgattgtttctgcggtccgcacgg
cgatcggcagctttaacggctctttagcgagcaccctctgcaatcgatctgggtgcgacggtcattaaggccgcca
ttgaacgcgccaaaatcgacagccagcacgttgatgaggtgatcatgggcaatgtgttacaagccggcctgggtc
aaaacccagcgcgtcaagcactgttaaaatctggtctggccgagacgtgtgtggcttcaccgtcaataaggttt
gaggctctggcctgaagagcgtggccctggcagcacaagcgattcaagccggtcaggcacaaagcatcgttgcgg
gtggcatggagaacatgtctctggcgccgtacttattagatgccaaagcccgcagcggttatcgcctgggcgatg
gtcaggtgtacgacgtcatcttacgcgatggcttaatgtgcgcgacccacggttaccacatgggtattacggccg
aaaacgtggcgaaagaatacggcattacgcgcgagatgcaggatgaattagcactgcactctcagcgcaaagcag
cagccgcgatcgagtctggtgcgtttacggcggaaatcgtgccagttaacgtggtcacgcgcaagaagacgttcg
ttttcagccaggacgagttcccgaaggcaaacagcacgcggaggccttaggtgccttacgccagcctttgaca
aagcgggcacggtcaccgccggtaatgcgagcggcatcaatgatggtgcagcggcactggtcatcatggaagaga
gcgccgcattagcagcgggtctgacccattagcgcgcattaaatcttatgccagcggcggcgtcccaccagccc
tgatgggcatgggtccggtccagccacgcaaaaagccctgcaattagcggcctgcaactggccgacattgatc
tgatcgaggcgaacgaggcgtttgcagcgcagttcctggcggtgggtaagaatctgggcttcgacagcgagaaag
tcaatgtgaacggtggcgcgattgcgttaggccatccgattggtgcaagcggcgcacgcatcttagtgacgttac
tgcacgccatgcaggcacgcgacaagaccttaggcctggcgacctttatgtattggtggcggtcaaggtatcgcca
tggtgatcgaacgcctgaactgatgaaggaggaaagcaaaatgaaactgagcaccaagctgtgctggtgtggcat
```

FIG. 19B

```
caagggtcgcctgcgcccacaaaagcagcaacagctgcacaacacgaacctgcaaatgaccgagctgaaaagca
gaagacggccgagcaaaagaccgcccgcagaacgttggcatcaagggcatccagatttatatcccgacgcagtg
tgtcaaccaatctgagctggagaaattcgatggcgtcagccagggtaagtacaccatcggcctgggccagaccaa
catgagcttcgtgaacgaccgtgaggacatctattctatgagcctgacggtgctgtctaagctgatcaagagcta
caacatcgacacgaataagatcggtcgtctggaggtgggtacggagacgctgattgacaagagcaaaagcgtgaa
gtctgtcttaatgcagctgttcggcgagaacacggatgtcgagggtatcgacaccctgaacgcgtgttacggcgg
caccaacgcactgttcaatagcctgaactggattgagagcaacgcctgggatggccgcgatgcgatcgtcgtgtg
cggcgatatcgccatctatgacaaggtgcggcacgtccgaccggcgtgcaggcaccgttgcgatgtggattgg
cccggacgcaccaattgtcttcgattctgtccgcgcgtcttacatggagcacgcctacgacttttacaagccgga
cttcacgagcgaataccgtacgtggacggccacttctctctgacctgctatgtgaaggcgctggaccaggttta
taagtcttatagcaaaaaggcgatttctaagggcctggtcagcgacccggcaggcagcgacgccctgaacgtgct
gaagtatttcgactacaacgtgttccatgtcccgacctgcaaattagtgaccaaatcttatggccgcctgttata
taatgatttccgtgccaaccgcagctgttccggaggttgacgccgagctggcgacgcgtgattacgacgagag
cctgaccgacaagaacatcgagaagaccttcgtcaacgtcgcgaagccgttccacaaagagcgtgtggcccaaag
cctgatcgtcccgaccaacacgggcaacatgtataccgcgtctgtctacgcggcattcgcgagcctgctgaatta
cgtcggttctgacgacctgcagggcaagcgcgttggcctgttcagctacggtagcggcttagcggccagcctgta
tagctgcaaaattgtcggcgacgtccagcacatcatcaaggagctggacatcaccaacaagctggcgaagcgcat
caccgagacgccgaaagattacgaggcagcgatcgagttacgcgagaatgcgcatctgaagaagaacttcaagcc
gcaaggtagcatcgagcacctgcagagcggcgtctactacctgacgaacattgacgacaagttccgccgttctta
tgacgtcaaaaagtaactagtaggaggaaaacatcatggtgctgacgaacaaaaccgtcattagcggcagcaagg
tgaagtctctgagcagcgcccaaagctctagcagcggcccgtctagcagcagcgaggaggacgacagccgtgaca
ttgagtctctggacaagaagatccgcccgctggaggagttagaggccctgctgagcagcggcaacaccaagcagc
tgaagaacaaggaagttgcagcgctggtgatccaacgtaagctgccactgtatgcgctgaaaagaaactgggcg
atacgacgcgtgcggtcgcggtgcgtcgcaaagccttaagcatcttagcggaggcccggtgttagccagcgacc
gcctgccgtacaagaactacgactacgaccgcgtgtttggcgcgtgctgcgagaatgtcattggctacatgccgt
taccggttggtgtgatcggcccgctggtcattgatggcacgagctatcacattccaatggcgaccacggaaggtt
gcttagtcgccagcgccatgcgtggctgtaaggcgattaacgccggcggtggcgcgacgaccgtgttaaccaagg
atggtatgacgcgcggtccggtcgtccgcttcccaacgctgaagcgcagcggcgcgtgtaagatttggctggatt
ctgaggagggccaaaacgcgatcaagaaagccttcaactctacgagccgtttcgcgcgtttacagcatatccaga
cctgcctggccggcgacctgctgttcatgcgcttccgcaccaccacgggcgatgcgatgggcatgaacatgatca
gcaagggcgtcgaatatagcctgaaacaaatggtggaagaatatggctgggaggacatggaggttgtctctgtga
gcggcaactattgcaccgacaagaagccggcagccattaactggattgagggtcgcgcggcaaaagcgtcgtggcag
aagcgaccatcccaggcgacgtggtccgtaaggttctgaagagcgacgtcagcgccctggttgagttaaatatcg
cgaaaacctggtcggcagcgcgatgcgggcagcgtgggtggctttaacgcacatgcagcgaatctggttacgg
cggttttcttagccttaggtcaggacccagcccaaaatgtcgagagcagcaactgcattaccttaatgaaagagg
ttgacggtgacctgcgcatcagcgtttctatgccgtctatcgaggtcggcacgatcggcggcggcaccgttttag
aaccgcaaggtgcgatgctggatctgctggcgtgcgcggccacatgcaacggcccaggcaccaatgccgcc
aactggcccgtatcgtggcctgcgcggttctggcgggtgagctgagcctgtgcgccgcattagccgcgggccatt
```

FIG. 19C

```
tagttcaatctcacatgacccacaaccgcaagccggcagaaccaaccaagccaaataacctggacgcaaccgaca
ttaaccgtctgaaggatggcagcgtcacgtgcattaaaagctgaggatctaggaggaaataaccatgtctctgcc
attcctgacgtctgcgccaggtaaggtgatcatcttcggcgagcactctgcggtgtacaataagccggccgtcgc
cgcctctgtgtctgcgttacgcacctacctgctgatcagcgaatcttctgcaccggacacgatcgagctggactt
tccggacatcagcttcaaccacaagtggagcatcaacgacttcaacgcgatcacggaggaccaggtgaacagcca
aaagctggccaaagcccagcaagcaaccgacggtctgtctcaggagctggtgtctctgctggaccccgctgttagc
gcagttaagcgagagcttccattaccacgcgcgttctgcttcctgtacatgttcgtttgcctgtgcccgcacgc
aaagaacatcaagttcagcctgaagagcacgctgccgattggcgcaggcttaggctctagcgcatctatcagcgt
gagcctggcgctggcgatggcctatctgggtggcctgattggcagcaacgacctggagaaactgagcgaaaacga
caagcacatcgtgaaccagtgggcctttatcggcgagaagtgcattcatggcaccccgagcggcattgacaacgc
agttgccacgtatggcaacgccctgctgttcgagaaagacagccacaacggcacgatcaacacgaacaacttcaa
gttcctggacgacttccccggcgatcccgatgattctgacctacaccgtatcccacgcagcaccaaggatttagt
cgcccgcgtgcgtgttttagtcaccgaaaagttcccggaggtgatgaagccgatcctggacgcgatgggcgagtg
cgcgctgcagggtctggagatcatgaccaagctgagcaagtgcaagggcaccgacgatgaggcggtggagaccaa
caatgagctgtacgagcagctgctggagctgatccgtatcaatcacggcctgctggtctctatcggtgtgtctca
cccgggcctggaactgatcaaaaacctgagcgacgacctgcgcattggctctacgaaattaacgggtgcaggtgg
cggtggctgctctttaacgctgctgcgccgtgacattacgcaggagcaaatcgacagcttcaagaagaagctgca
ggacgacttcagctacgagacgttcgagacggacctgggcggcacgggctgttgcctgctgagcgccaaaaatct
gaacaaggacctgaagatcaaaagcctggtgttccagctgttcgaaaacaagacgaccacgaagcagcagatcga
cgacctgttactgccgggtaacaccaatctgccgtggacgtcttaaggatctaggaggagatcatatgagcgaa
ttacgtgcattcagcgcgccaggtaaggcactgctggccggtggctacctggtgttagacaccaagtacgaggcg
ttcgtcgtcggcttatctgcccgtatgcatgcagttgcccaccgtatggtagcctgcagggctctgacaagttc
gaagtgcgtgtgaagagcaagcagttcaaggacggcgagtggctgtaccacattagcccaaagagcggcttcatc
ccggttagcattggtggcagcaagaacccatttatcgagaaggtcattgccaacgtcttcagctacttcaagccg
aatatggacgattactgcaaccgcaacctgttcgtcatcgacattttcagcgacgacgcgtaccacagccaagag
gactctgttacggagcatcgtggtaaccgccgcctgagcttccacagccatcgcattgaggaggtgccgaagacg
ggtctgggttctagcgccggtttagttaccgtcttaacgacggcgttagcgagcttcttcgtgagcgacctggag
aacaacgtggacaagtaccgcgaagtgattcataacctggcgcaggtggcacattgtcaggcccaaggtaagatt
ggctctggttttgatgtggcagcggcgcctatggctctatccgctatcgccgctttccgccggccctgatcagc
aatctgccggacatcggctctgcgacgtatggtagcaaactggcgcatctggtggacgaagaagactggaacatc
accattaagtctaatcacctgcgagcggcttaacgttatggatggcgatatcaagaacggcagcgaaacggtt
aagctggtgcagaaagtgaaaaactggtacgacagccacatgccggaaagcctgaagatttacacggagctggac
cacgccaatagccgtttcatggatggtctgagcaagctggaccgcctgcacgaaacccacgacgactacagcgac
caaatcttcgagagcctggagcgcaatgactgcacctgccagaagtacccggagatcacggaggtccgcgatgcc
gtggcaacgattcgccgtagcttccgcaaaattacgaaggagagcggcgcggatatcgaaccaccggtccagacg
tctctgctggacgactgtcaaaaccttaaaggcgtgttaacgtgcctgattccgggcgcgggtggttacgacgcc
attgccgtcatcacgaaacaggacgtcgatctgcgcgcacaaacggccaacgacaaacgtttcagcaaagtccaa
tggctggatgttacgcaggccgactgggggtgttcgcaaggagaaggacccggaaacgtatctggataagtgagga
```

FIG. 19D

```
tctaggaggattatgagatgaccgtttacacagcatccgttaccgcacccgtcaacatcgcaaccct taagtatt
ggggggaaaagggacacgaagttgaatctgcccaccaattcgtccatatcagtgactttatcgcaagatgacctca
gaacgttgacctctgcggctactgcacctgagtttgaacgcgacactttgtggttaaatggagaaccacacagca
tcgacaatgaaagaactcaaaattgtctgcgcgacctacgccaattaagaaaggaaatggaatcgaaggacgcct
cattgcccacattatctcaatggaaactccacattgtctccgaaaataactttcctacagcagctggtttagctt
cctccgctgctggctttgctgcattggtctctgcaattgctaagttataccaattaccacagtcaacttcagaaa
tatctagaatagcaagaaagggtctggttcagcttgtagatcgttgtttggcggatacgtggcctgggaaatgg
gaaaagctgaagatggtcatgattccatggcagtacaaatcgcagacagctctgactggcctcagatgaaagctt
gtgtcctagttgtcagcgatattaaaaaggatgtgagttccactcagggtatgcaattgaccgtggcaacctccg
aactatttaaagaaagaattgaacatgtcgtaccaaagagatttgaagtcatgcgtaaagccattgttgaaaaag
atttcgccacctttgcaaaggaaacaatgatggattccaactctttccatgccacatgtttggactcttteccte
caatattctacatgaatgacacttccaagcgtatcatcagttggtgccacaccattaatcagtttacggagaaa
caatcgttgcatacacgtttgatgcaggtccaaatgctgtgttgtactacttagctgaaaatgagtcgaaactct
ttgcatttatctataaattgtttggctctgttcctggatgggacaagaaatttactactgagcagcttgaggctt
tcaaccatcaatttgaatcatctaacttactgcacgtgaattggatcttgagttgcaaaaggatgttgccagag
tgattttaactcaagtcggttcaggcccacaagaaacaaacgaatcttttgattgacgcaaagactggtctaccaa
aggaataaggatctaggaggtaatgataatgcaaacggaacacgtcattttattgaatgcacaggagttcccac
gggtacgctggaaaagtatgccgcacacacggcagacacccgcttacatctcgcgttctccagttggctgtttaa
tgccaaaggacaattattagttaccgccgcgcactgagcaaaaagcatggcctggcgtgtggactaactcggt
ttgtgggcacccacaactgggagaaagcaacgaagacgcagtgatccgccgttgccgttatgagcttggcgtgga
aattacgcctcctgaatctatctatcctgactttcgctaccgcgccaccgatccgagtggcattgtggaaaatga
agtgtgtccggtatttgccgcacgcaccactagtgcgttacagatcaatgatgatgaagtgatggattatcaatg
gtgtgatttagcagatgtattacacggtattgatgccacgccgtgggcgttcagtccgtggatggtgatgcaggc
gacaaatcgcgaagccagaaaacgattatctgcatttacccagcttaaataagGAtctttaagaaggagatata
catATGGTGGAATTTGATTTTAACAAATATATGGATAGCAAAGCGATGACCGTGAACGAAGCGCTGAACAAAGCG
ATTCCGCTGCGCTATCCGCAGAAAATTTATGAAAGCATGCGCTATAGCCTGCTGGCGGGCGGCAAACGCGTGCGC
CCGGTGCTGTGCATTGCGGCGTGCGAACTGGTGGGCGGCACCGAAGAACTGGCGATTCCGACCGCGTGCGCGATT
GAAATGATTCATACCATGAGCCTGATGCATGATGATCTGCCGTGCATTGATAACGATGATCTGCGCCGCGGCAAA
CCGACCAACCATAAAATTTTTGGCGAAGATACCGCGGTGACCGCGGGCAACGCGCTGCATAGCTATGCGTTTGAA
CATATTGCGGTGAGCACCAGCAAAACCGTGGGCGCGGATCGCATTCTGCGCATGGTGAGCGAACTGGGCCGCGCG
ACCGGCAGCGAAGGCGTGATGGGCGGCCAGATGGTGGATATTGCGAGCGAAGGCGATCCGAGCATTGATCTGCAG
ACCCTGGAATGGATTCATATTCATAAAACCGCGATGCTGCTGGAATGCAGCGTGGTGTGCGGCGCGATTATTGGC
GGCGCGAGCGAAATTGTGATTGAACGCGCGCGCCGCTATGCGCGCTGCGTGGGCCTGCTGTTTCAGGTGGTGGAT
GATATTCTGGATGTGACCAAAAGCAGCGATGAACTGGGCAAAACCGCGGGCAAAGATTTAATTAGCGATAAAGCG
ACCTATCCGAAACTGATGGGCCTGGAAAAAGCGAAAGAATTTAGCGATGAACTGCTGAACCGCGCGAAAGGCGAA
CTGAGCTGCTTTGATCCGGTGAAAGCGGCGCCGCTGCTGGGCCTGGCGGATTATGTGGCGTTTCGCCAGAACTAA
GGATCCaaactcgagtaaggatctccaggcatcaaataaaacgaaaggctcagtcgaaagactgggcctttcgtt
ttatctgttgtttgtcggtgaacgctctctactagagtcacactggctcacctcgggtgggcctttctgcgttt
```

FIG. 19E

```
atacctagggatatattccgcttcctcgctcactgactcgctacgctcggtcgttcgactgcggcgagcggaaat
ggcttacgaacggggcggagatttcctggaagatgccaggaagatacttaacagggaagtgagagggccgcggca
aagccgttttttccataggctccgccccctgacaagcatcacgaaatctgacgctcaaatcagtggtggcgaaac
ccgacaggactataaagataccaggcgtttccccctggcggctccctcgtgcgctctcctgttcctgcctttcgg
tttaccggtgtcattccgctgttatggccgcgtttgtctcattccacgcctgacactcagttccgggtaggcagt
tcgctccaagctggactgtatgcacgaaccccccgttcagtccgaccgctgcgccttatccggtaactatcgtct
tgagtccaacccggaaagacatgcaaaagcaccactggcagcagccactggtaattgatttagaggagttagtct
tgaagtcatgcgccggttaaggctaaactgaaaggacaagttttggtgactgcgctcctccaagccagttacctc
ggttcaaagagttggtagctcagagaaccttcgaaaaccgccctgcaaggcggtttttcgttttcagagcaag
agattacgcgcagaccaaaacgatctcaagaagatcatcttattaatcagataaaatatttctagatttcagtgc
aatttatctcttcaaatgtagcacctgaagtcagccccatacgatataagttgttactagtgcttggattctcac
caataaaaaacgcccggcggcaaccgagcgttctgaacaaatccagatggagttctgaggtcattactggatcta
tcaacaggagtccaagcgagctcgatatcaaattacgccccgccctgccactcatcgcagtactgttgtaattca
ttaagcattctgccgacatggaagccatcacaaacggcatgatgaacctgaatcgccagcggcatcagcaccttg
tcgccttgcgtataatatttgccatggtgaaaacgggggcgaagaagttgtccatattggccacgtttaaatca
aaactggtgaaactcacccagggattggctgagacgaaaaacatattctcaataaacccttagggaaataggcc
aggttttcaccgtaacacgccacatcttgcgaatatatgtgtagaaactgccggaaatcgtcgtggtattcactc
cagagcgatgaaaacgtttcagtttgctcatggaaaacggtgtaacaagggtgaacactatcccatatcaccagc
tcaccgtctttcattgccatacgaaattccggatgagcattcatcaggcgggcaagaatgtgaataaaggccgga
taaaacttgtgcttattttctttacggtctttaaaaggccgtaatatccagctgaacggtctggttataggta
cattgagcaactgactgaaatgcctcaaaatgttctttacgatgccattgggatatatcaacggtggtatatcca
gtgatttttttctccattttagcttccttagctcctgaaatctcgataactcaaaaaatacgcccggtagtgat
cttatttcattatggtgaaagttggaacctcttacgtgccgatcaacgtctcatttcgccagatatc
```

FIG. 20A

```
gacgtcggtgcctaatgagtgagctaacttacattaattgcgttgcgctcactgcccgctttccagtcgggaaac
ctgtcgtgccagctgcattaatgaatcggccaacgcgcggggagaggcggtttgcgtattgggcgccagggtggt
ttttcttttcaccagtgagacgggcaacagctgattgcccttcaccgcctggccctgagagagttgcagcaagcg
gtccacgctggtttgccccagcaggcgaaaatcctgtttgatggtggttaacggcgggatataacatgagctgtc
ttcggtatcgtcgtatcccactaccgagatgtccgcaccaacgcgcagcccggactcggtaatggcgcgcattgc
gcccagcgccatctgatcgttggcaaccagcatcgcagtgggaacgatgccctcattcagcatttgcatggtttg
ttgaaaaccggacatggcactccagtcgcctttcccgttccgctatcggctgaatttgattgcgagtgagatattt
atgccagccagccagacgcagacgcgccgagacagaacttaatgggcccgctaacagcgcgatttgctggtgacc
caatgcgaccagatgctccacgccagtcgcgtaccgtcttcatgggagaaaataatactgttgatgggtgtctg
gtcagagacatcaagaaataacgccggaacattagtgcaggcagcttccacagcaatggcatcctggtcatccag
cggatagttaatgatcagcccactgacgcgttgcgcgagaagattgtgcaccgccgctttacaggcttcgacgcc
gcttcgttctaccatcgacaccaccacgctggcacccagttgatcggcgcgagatttaatcgccgcgacaatttg
cgacggcgcgtgcagggccagactggaggtggcaacgccaatcagcaacgactgtttgcccgccagttgttgtgc
cacgcggttgggaatgtaattcagctccgccatcgccgcttccacttttttcccgcgttttcgcagaaacgtggct
ggcctggttcaccacgcgggaaacggtctgataagagacaccggcatactctgcgacatcgtataacgttactgg
tttcacattcaccaccctgaattgactctcttccgggcgctatcatgccataccgcgaaaggttttgcgccattc
gatggtgtccgggatctcgacgctctcccttatgcgactcctgcattaggaagcagcccagtagtaggttgaggc
cgttgagcaccgccgccgcaaggaatggtgcatgcaaggagatggcgcccaacagtcccccggccacggggcctg
ccaccatacccacgccgaaacaagcgctcatgagcccgaagtggcgagcccgatcttccccatcggtgatgtcgg
cgatataggcgccagcaaccgcacctgtggcgccggtgatgccggccacgatgcgtccggcgtagaggatcgaga
tcgtttaggcaccccaggctttacactttatgcttccggctcgtataatgtgtggaattgtgagcggataacaat
ttcagaattcaaaagatctaaaggaggccatcctggccatgaagaactgtgtgattgtttctgcggtccgcacgg
cgatcggcagctttaacggctctttagcgagcacctctgcaatcgatctggtgcgacggtcattaaggccgcca
ttgaacgcgccaaaatcgacagccagcacgttgatgaggtgatcatgggcaatgtgttacaagccggcctgggtc
aaaacccagcgcgtcaagcactgttaaaatctggtctggccgagaccgtgtgtggcttcaccgtcaataaggttt
gcggctctggcctgaagagcgtggccctggcagcacaagcgattcaagccggtcaggcacaaagcatcgttgcgg
gtggcatggagaacatgtctctggcgccgtacttattagatgccaaagcccgcagcggttatcgcctgggcgatg
gtcaggtgtacgacgtcatcttacgcgatggcttaatgtgcgcgacccacggttaccacatgggtattacggccg
aaaacgtggcgaaagaatacggcattacgcgcgagatgcaggatgaattagcactgcactctcagcgcaaagcag
cagccgcgatcgagtctggtgcgtttacggcgaaatcgtgccagttaacgtggtcacgcgcaagaagacgttcg
ttttcagccaggacgagttcccgaaggcaaacagcacgcggaggccttaggtgccttacgcccagcctttgaca
aagcgggcacggtcaccgccggtaatgcgagcggcatcaatgatggtgcagcggcactggtcatcatggaagaga
gcgccgcattagcagcgggtctgaccccattagcgcgcattaaatcttatgccagcggcggcgtcccaccagccc
tgatgggcatgggtccggtcccagccacgcaaaaagccctgcaattagcgggcctgcaactggccgacattgatc
```

FIG. 20B

```
tgatcgaggcgaacgaggcgtttgcagcgcagttcctggcggtgggtaagaatctgggcttcgacagcgagaaag
tcaatgtgaacggtggcgcgattgcgttaggccatccgattggtgcaagcggcgcacgcatcttagtgacgttac
tgcacgccatgcaggcacgcgacaagaccttaggcctggcgaccttatgtattggtggcggtcaaggtatcgcca
tggtgatcgaacgcctgaactgatgaaggaggaaagcaaaatgaaactgagcaccaagctgtgctggtgtggcat
caagggtcgcctgcgcccacaaaagcagcaacagctgcacaacacgaacctgcaaatgaccgagctgaaaagca
gaagacggccgagcaaaagaccgcccgcagaacgttggcatcaagggcatccagatttatatcccgacgcagtg
tgtcaaccaatctgagctggagaaattcgatggcgtcagccagggtaagtacaccatcggcctgggccagaccaa
catgagcttcgtgaacgaccgtgaggacatctattctatgagcctgacggtgctgtctaagctgatcaagagcta
caacatcgacacgaataagatcggtcgtctggaggtgggtacggagacgctgattgacaagagcaaaagcgtgaa
gtctgtcttaatgcagctgttcggcgagaacacggatgtcgagggtatcgacaccctgaacgcgtgttacggcgg
caccaacgcactgttcaatagcctgaactggattgagagcaacgcctgggatggccgcgatgcgatcgtcgtgtg
cggcgatatcgccatctatgacaagggtgcggcacgtccgaccggcggtgcaggcaccgttgcgatgtggattgg
cccggacgcaccaattgtcttcgattctgtccgcgcgtcttacatggagcacgcctacgacttttacaagccgga
cttcacgagcgaatacccgtacgtggacggccactctctctgacctgctatgtgaaggcgctggaccaggttta
taagtcttatagcaaaaaggcgatttctaagggcctggtcagcgacccggcaggcagcgacgccctgaacgtgct
gaagtatttcgactacaacgtgttccatgtcccgacctgcaaattagtgaccaaatcttatggcgcctgttata
taatgatttccgtgccaaccgcagctgttcccggaggttgacgccgagctggcgacgcgtgattacgacgagag
cctgaccgacaagaacatcgagaagaccttcgtcaacgtcgcgaagccgttccacaaagagcgtgtggcccaaag
cctgatcgtcccgaccaacacgggcaacatgtataccgcgtctgtctacgcggcattcgcgagcctgctgaatta
cgtcggttctgacgacctgcagggcaagcgcgttggcctgttcagctacggtagcggcttagcggccagcctgta
tagctgcaaaattgtcggcgacgtccagcacatcatcaaggagctggacatcaccaacaagctggcgaagcgcat
caccgagacgccgaaagattacgaggcagcgatcgagttacgcgagaatgcgcatctgaagaagaacttcaagcc
gcaaggtagcatcgagcacctgcagagcggcgtctactacctgacgaacattgacgacaagttccgccgttctta
tgacgtcaaaaagtaactagtaggaggaaaacatcatggtgctgacgaacaaaaccgtcattagcggcagcaagg
tgaagtctctgagcagcgcccaaagctctagcagcggcccgtctagcagcagcgaggaggacgacagccgtgaca
ttgagtctctggacaagaagatccgcccgctggaggagttagaggccctgctgagcagcggcaacaccaagcagc
tgaagaacaaggaagttgcagcgctggtgatccacggtaagctgccactgtatgcgctggaaaagaaactgggcg
atacgacgcgtgcggtcgcggtgcgtcgcaaagccttaagcatcttagcggaggccccggtgttagccagcgacc
gcctgccgtacaagaactacgactacgaccgcgtgtttggcgcgtgctgcgagaatgtcattggctacatgccgt
taccggttggtgtgatcggcccgctggtcattgatggcacgagctatcacattccaatggcgaccacggaaggtt
gcttagtcgccagcgccatgcgtggctgtaaggcgattaacgccggcggtgcgcgacgacgtgttaaccaagg
atggtatgacgcgcggtccggtcgtccgcttcccaacgctgaagcgcagcggcgcgtgtaagatttggctggatt
ctgaggagggcaaaacgcgatcaagaaagccttcaactctacgagccgtttcgcgcgtttacagcatatccaga
cctgcctggccggcgacctgctgttcatgcgcttccgcaccaccacgggcgatgcgatgggcatgaacatgatca
gcaagggcgtcgaatatagcctgaaacaaatggtggaagaatatggctgggaggacatggaggttgtctctgtga
gcggcaactattgcaccgacaagaagccggcagccattaactggattgagggtcgcggcaaaagcgtcgtggcag
```

FIG. 20C

```
aagcgaccatcccaggcgacgtggtccgtaaggttctgaagagcgacgtcagcgccctggttgagttaaatatcg
cgaaaaacctggtcggcagcgcgatggcgggcagcgtgggtggctttaacgcacatgcagcgaatctggttacgg
cggttttcttagcct taggtcaggacccagcccaaaatgtcgagagcagcaactgcattaccttaatgaaagagg
ttgacggtgacctgcgcatcagcgtttctatgccgtctatcgaggtcggcacgatcggcggcggcaccgtttag
aaccgcaaggtgcgatgctggatctgctgggcgtgcgcggccacatgcaacggcccaggcaccaatgcccgcc
aactggcccgtatcgtggcctgcgcggttctggcgggtgagctgagcctgtgcgccgcattagccgcgggccatt
tagttcaatctcacatgacccacaaccgcaagccggcagaaccaaccaagccaaataacctggacgcaaccgaca
ttaaccgtctgaaggatggcagcgtcacgtgcattaaaagctgaggatctccaggcatcaaataaaacgaaaggc
tcagtcgaaagactgggcctttcgttttatctgttgtttgtcggtgaacgctctctactagagtcacactggctc
accttcgggtgggcctttctgcgtttatagcgaattgatctggtttgacagcttatcatcgactgcacggtgcac
caatgcttctggcgtcaggcagccatcggaagctgtggtatggctgtgcaggtcgtaaatcactgcataattcgt
gtcgctcaaggcgcactcccgttctggataatgttttttgcgccgacatcataacggttctggcaaatattctga
aatgagctgttgacaattaatcatccggctcgtataatgtgtggaattgtgagcggataacaatttcaggatcta
ggaggaaataaccatgtctctgccattcctgacgtctgcgccaggtaaggtgatcatcttcggcgagcactctgc
ggtgtacaataagccggccgtcgccgctctgtctgcgttacgcacctacctgctgatcagcgaatcttctgc
accggacacgatcgagctggactttccggacatcagcttcaaccacaagtggagcatcaacgacttcaacgcgat
cacggaggaccaggtgaacagccaaaagctggccaaagcccagcaagcaaccgacggtctgtctcaggagctggt
gtctctgctggacccgctgttagcgcagttaagcgagagcttccattaccacgccgcgttctgcttcctgtacat
gttcgtttgcctgtgcccgcacgcaaagaacatcaagttcagcctgaagagcacgctgccgattggcgcaggctt
aggctctagcgcatctatcagcgtgagcctggcgctggcgatggcctatctgggtggcctgattggcagcaacga
cctggagaaactgagcgaaaacgacaagcacatcgtgaaccagtgggcctttatcggcgagaagtgcattcatgg
caccccgagcggcattgacaacgcagttgccacgtatggcaacgccctgctgttcgagaaagacagccacaacgg
cacgatcaacacgaacaacttcaagttcctggacgacttcccggcgatcccgatgattctgacctacacccgtat
cccacgcagcaccaaggatttagtcgcccgcgtgcgtgttttagtcaccgaaaagttcccggaggtgatgaagcc
gatcctggacgcgatgggcgagtgcgcgctgcagggtctggagatcatgaccaagctgagcaagtgcaagggcac
cgacgatgaggcggtggagaccaacaatgagctgtacgagcagctgctggagctgatccgtatcaatcacggcct
gctggtctctatcggtgtgtctcacccgggcctggaactgatcaaaaacctgagcgacgacctgcgcattggctc
tacgaaattaacgggtgcaggtggcggtggctgctcttttaacgctgctgcgccgtgacattacgcaggagcaaat
cgacagcttcaagaagaagctgcaggacgacttcagctacgagacgttcgagacggacctgggcggcacgggctg
ttgcctgctgagcgccaaaaatctgaacaaggacctgaagatcaaaagcctggtgttccagctgttcgaaaacaa
gacgaccacgaagcagcagatcgacgacctgttactgccgggtaacaccaatctgccgtggacgtcttaaggatc
taggagggagatcatatgagcgaattacgtgcattcagcgcgccaggtaaggcactgctggccggtggctacctg
gtgttagacaccaagtacgaggcgttcgtcgtggcttatctgccccgtatgcatgcagttgcccacccgtatggt
agcctgcagggtctgacaagttcgaagtgcgtgtgaagagcaagcagttcaaggacggcgagtggctgtaccac
attagcccaaagagcggcttcatcccggttagcattggtggcagcaagaacccatttatcgagaaggtcattgcc
aacgtcttcagctacttcaagccgaatatggacgattactgcaaccgcaacctgttcgtcatcgacatttcagc
```

FIG. 20D

```
gacgacgcgtaccacagccaagaggactctgttacggagcatcgtggtaaccgccgcctgagcttccacagccat
cgcattgaggaggtgccgaagacgggtctgggttctagcgccggtttagttaccgtcttaacgacggcgttagcg
agcttcttcgtgagcgacctggagaacaacgtggacaagtaccgcgaagtgattcataacctggcgcaggtggca
cattgtcaggcccaaggtaagattggctctggttttgatgtggcagcggccgcctatggctctatccgctatcgc
cgctttccgccggccctgatcagcaatctgccggacatcggctctgcgacgtatggtagcaaactggcgcatctg
gtggacgaagaagactggaacatcaccattaagtctaatcacctgccgagcggcttaacgttatggatgggcgat
atcaagaacggcagcgaaacggttaagctggtgcagaaagtgaaaaactggtacgacagccacatgccggaaagc
ctgaagatttacacggagctggaccacgccaatagccgtttcatggatggtctgagcaagctggaccgcctgcac
gaaacccacgacgactacagcgaccaaatcttcgagagcctggagcgcaatgactgcacctgccagaagtacccg
gagatcacggaggtccgcgatgccgtggcaacgattcgccgtagcttccgcaaaattacgaaggagagcggcgcg
gatatcgaaccaccggtccagacgtctctgctggacgactgtcaaaccttaaaggggcgtgttaacgtgcctgatt
ccgggcgcgggtggttacgacgccattgccgtcatcacgaaacaggacgtcgatctgcgcgcacaaacggccaac
gacaaacgtttcagcaaagtccaatggctggatgttacgcaggccgactgggtgttcgcaaggagaaggacccg
gaaacgtatctggataagtgaggatctaggaggattatgagatgaccgtttacacagcatccgttaccgcacccg
tcaacatcgcaacccttaagtattgggggaaaagggacacgaagttgaatctgcccaccaattcgtccatatcag
tgactttatcgcaagatgacctcagaacgttgacctctgcggctactgcacctgagtttgaacgcgacactttgt
ggttaaatggagaaccacacagcatcgacaatgaagaactcaaaattgtctgcgcgacctacgccaattaagaa
aggaaatggaatcgaaggacgcctcattgcccacattatctcaatggaaactccacattgtctccgaaaataact
ttcctacagcagctggtttagcttcctccgctgctggctttgctgcattggtctctgcaattgctaagttatacc
aattaccacagtcaacttcagaaatatctagaatagcaagaaaggggtctggttcagcttgtagatcgttgtttg
gcggatacgtggcctgggaaatgggaaaagctgaagatggtcatgattccatggcagtacaaatcgcagacagct
ctgactggcctcagatgaaagcttgtgtcctagttgtcagcgatattaaaaaggatgtgagttccactcagggta
tgcaattgaccgtggcaacctccgaactatttaaagaaagaattgaacatgtcgtaccaaagagatttgaagtca
tgcgtaaagccattgttgaaaaagatttcgccacctttgcaaaggaaacaatgatggattccaactctttccatg
ccacatgtttggactctttccctccaatattctacatgaatgacacttccaagcgtatcatcagttggtgccaca
ccattaatcagttttacggagaaacaatcgttgcatacacgtttgatgcaggtccaaatgctgtgttgtactact
tagctgaaaatgagtcgaaactctttgcatttatctataaattgtttggctctgttcctggatgggacaagaaat
ttactactgagcagcttgaggctttcaaccatcaatttgaatcatctaacttttactgcacgtgaattggatcttg
agttgcaaaggatgttgccagagtgattttaactcaagtcggttcaggcccacaagaaacaaacgaatctttga
ttgacgcaaagactggtctaccaaaggaataaggatctaggaggtaatgataatgcaaacggaacacgtcattt
attgaatgcacagggagttcccacgggtacgctggaaaagtatgccgcacacacggcagacacccgcttacatct
cgcgttctccagttggctgtttaatgccaaaggacaattattagttaccgccgcgcactgagcaaaaaagcatg
gcctggcgtgtggactaactcggtttgtgggcacccacaactgggagaaagcaacgaagacgcagtgatccgccg
ttgccgttatgagcttggcgtggaaattacgcctcctgaatctatctatcctgactttcgctacgcgccaccga
tccgagtggcattgtggaaaatgaagtgtgtccggtatttccgcacgcaccactagtgcgttacagatcaatga
tgatgaagtgatggattatcaatggtgtgatttagcagatgtattacacggtattgatgccacgccgtgggcgtt
```

FIG. 20E

```
cagtccgtggatggtgatgcaggcgacaaatcgcgaagccagaaaacgattatctgcatttacccagcttaaata
aggatccaaactcgagtaaggatctccaggcatcaaataaaacgaaaggctcagtcgaaagactgggcctttcgt
tttatctgttgtttgtcggtgaacgctctctactagagtcacactggctcaccttcgggtgggcctttctgcgtt
tatacctagggatatattccgcttcctcgctcactgactcgctacgctcggtcgttcgactgcggcgagcggaaa
tggcttacgaacggggcggagatttcctggaagatgccaggaagatacttaacagggaagtgagagggccgcggc
aaagccgttttttccataggctccgccccctgacaagcatcacgaaatctgacgctcaaatcagtggtggcgaaa
cccgacaggactataaagataccaggcgtttccccctggcggctccctcgtgcgctctcctgttcctgcctttcg
gtttaccggtgtcattccgctgttatggccgcgtttgtctcattccacgcctgacactcagttccgggtaggcag
ttcgctccaagctggactgtatgcacgaaccccccgttcagtccgaccgctgcgccttatccggtaactatcgtc
ttgagtccaacccggaaagacatgcaaaagcaccactggcagcagccactggtaattgatttagaggagttagtc
ttgaagtcatgcgccggttaaggctaaactgaaaggacaagttttggtgactgcgctcctccaagccagttacct
cggttcaaagagttggtagctcagagaaccttcgaaaaaccgcctgcaaggcggttttttcgttttcagagcaa
gagattacgcgcagaccaaaacgatctcaagaagatcatcttattaatcagataaaatatttctagatttcagtg
caatttatctcttcaaatgtagcacctgaagtcagccccatacgatataagttgttactagtgcttggattctca
ccaataaaaaacgcccggcggcaaccgagcgttctgaacaaatccagatggagttctgaggtcattactggatct
atcaacaggagtccaagcgagctcgatatcaaattacgccccgccctgccactcatcgcagtactgttgtaattc
attaagcattctgccgacatggaagccatcacaaacggcatgatgaacctgaatcgccagcggcatcagcaccttc
gtcgccttgcgtataatatttgcccatggtgaaaacggggcgaagaagttgtccatattggccacgtttaaatc
aaaactggtgaaactcacccagggattggctgagacgaaaaacatattctcaataaacccttaggggaaataggc
caggttttcaccgtaacacgccacatcttgcgaatatatgtgtagaaactgccggaaatcgtcgtggtattcact
ccagagcgatgaaaacgtttcagttgctcatggaaaacggtgtaacaagggtgaacactatcccatatcaccag
ctcaccgtctttcattgccatacgaaattccggatgagcattcatcaggcgggcaagaatgtgaataaaggccgg
ataaaacttgtgcttattttttctttacggtctttaaaaaggccgtaatatccagctgaacggtctggttataggt
acattgagcaactgactgaaatgcctcaaaatgttctttacgatgccattggatatatcaacggtggtatatcc
agtgattttttttctccattttagcttcctagctcctgaaaatctcgataactcaaaaaatacgcccggtagtga
tcttatttcattatggtgaaagttggaacctcttacgtgccgatcaacgtctcattttcgccagatatc
```

FIG. 21A gacgtggtgcctaatgagtgagctaacttacattaattgcgttgcgctcactgcccgctttccagtcgggaaac
ctgtcgtgccagctgcattaatgaatcggccaacgcgcggggagaggcggttttgcgtattgggcgccaggtggt
ttttcttttcaccagtgagacgggcaacagctgattgcccttcaccgcctggccctgagagagttgcagcaagcg
gtccacgctggtttgccccagcaggcgaaaatcctgtttgatggtggttaacggcgggatataacatgagctgtc
ttcggtatcgtcgtatcccactaccgagatgtccgcaccaacgcgcagcccggactcggtaatggcgcgcattgc
gcccagcgccatctgatcgttggcaaccagcatcgcagtgggaacgatgccctcattcagcatttgcatggtttg
ttgaaaaccggacatggcactccagtcgccttcccgttccgctatcggctgaatttgattgcgagtgagatattt
atgccagccagccagacgcagacgcgcgagacagaacttaatgggcccgctaacagcgcgatttgctggtgacc
caatgcgaccagatgctccacgcccagtcgcgtaccgtcttcatgggagaaaataatactgttgatgggtgtctg
gtcagagacatcaagaaataacgccggaacattagtgcaggcagcttccacagcaatggcatcctggtcatccag
cggatagttaatgatcagcccactgacgcgttgcgcgagaagattgtgcaccgccgctttacaggcttcgacgcc
gcttcgttctaccatcgacaccaccacgctggcacccagttgatcggcgcgagatttaatcgccgcgacaatttg
cgacggcgcgtgcagggccagactggaggtggcaacgccaatcagcaacgactgtttgccgcccagttgttgtgc
cacgcggtgggaatgtaattcagctccgccatcgccgcttccacttttcccgcgttttcgcagaaacgtggct
ggcctggttcaccacgcgggaaacggtctgataagagacaccggcatactctgcgacatcgtataacgttactgg
tttcacattcaccaccctgaattgactctcttccgggcgctatcatgccataccgcgaaaggttttgcgccattc
gatggtgtccgggatctcgacgctctcccttatgcgactcctgcattaggaagcagcccagtagtaggttgaggc
cgttgagcaccgccgccgcaaggaatggtgcatgcaaggagatggcgcccaacagtccccggccacgggcctg
ccaccatacccacgccgaaacaagcgctcatgagcccgaagtggcgagccgatcttccccatcggtgatgtcgg
cgatataggcgccagcaaccgcacctgtggcgccggtgatgccggccacgatgcgtccggcgtagaggatcgaga
tcgtttaggcaccccaggcttttacactttatgcttccggctcgtataatgtgtggaattgtgagcggataacaat
ttcagaattcaaagatctaaaggaggccatcctggccatgaagaactgtgtgattgtttctgcggtccgcacgg
cgatcggcagctttaacggctctttagcgagcacctctgcaatcgatctgggtgcgacggtcattaaggccgcca
ttgaacgcgccaaaatcgacagccagcacgttgatgaggtgatcatgggcaatgtgttacaagccggcctgggtc
aaaaccagcgcgtcaagcactgttaaaatctggtctggccgagacgtgtgtggcttcaccgtcaataaggttt
gcggctctggcctgaagagcgtggccctggcagcacaagcgattcaagccggtcaggcacaaagcatcgttgcgg
gtggcatggagaacatgtctctggcgccgtacttattagatgccaaagcccgcagcggttatcgcctgggcgatg
gtcaggtgtacgacgtcatcttacgcgatggcttaatgtgcgcgacccacgttaccacatgggtattacggccg
aaaacgtggcgaaagaatacggcattacgcgcgagatgcaggatgaattagcactgcactctcagcgcaaagcag
cagccgcgatcgagtctggtgcgtttacggcggaaatcgtgccagttaacgtggtcacgcgcaagaagacgttcg
ttttcagccaggacgagttcccgaaggcaaacagcaccgcggaggccttaggtgccttacgccagcctttgaca
aagcgggcacggtcaccgccggtaatgcgagcggcatcaatgatggtgcagcggcactggtcatcatggaagaga
gcgccgcattagcagcgggtctgacccccattagcgcgcattaaatcttatgcagcggcggcgtcccaccagccc
tgatgggcatgggtccggtccagccacgcaaaaagccctgcaattagcgggcctgcaactggccgacattgatc
tgatcgaggcgaacgaggcgtttgcagcgcagttcctggcggtgggtaagaatctggcttcgacagcgagaaag
tcaatgtgaacggtggcgcgattgcgttaggccatccgattggtgcaagcggcgcacgcatcttagtgacgttac
tgcacgccatgcaggcacgcgacaagaccttaggcctggcgacctatgtattggtggcggtcaaggtatcgcca
tggtgatcgaacgcctgaactgatgaaggaggaaagcaaaatgaaactgagcaccaagctgtgctggtgtggcat

FIG. 21B

```
caagggtcgcctgcgcccacaaaagcagcaacagctgcacaacacgaacctgcaaatgaccgagctgaaaaagca
gaagacggccgagcaaaagaccgccgcagaacgttggcatcaagggcatccagatttatatcccgacgcagtg
tgtcaaccaatctgagctggagaaattcgatggcgtcagccagggtaagtacaccatcggcctgggccagaccaa
catgagcttcgtgaacgaccgtgaggacatctattctatgagcctgacggtgctgtctaagctgatcaagagcta
caacatcgacacgaataagatcggtcgtctggaggtgggtacgagacgctgattgacaagagcaaaagcgtgaa
gtctgtcttaatgcagctgttcggcgagaacacggatgtcgagggtatcgacaccctgaacgcgtgttacggcgg
caccaacgcactgttcaatagcctgaactggattgagagcaacgcctggatggccgcgatgcgatcgtcgtgtg
cggcgatatcgccatctatgacaaggtgcggcacgtccgaccggcggtgcaggcaccgttgcgatgtggattgg
cccggacgcaccaattgtcttcgattctgtccgcgcgtcttacatggagcacgcctacgacttttacaagccgga
cttcacgagcgaatacccgtacgtggacggccacttctctctgacctgctatgtgaaggcgctggaccaggttta
taagtcttatagcaaaaaggcgatttctaagggcctggtcagcgacccggcaggcagcgacgccctgaacgtgct
gaagtatttcgactacaacgtgttccatgtcccgacctgcaaattagtgaccaaatcttatggccgcctgttata
taatgatttccgtgccaaccccgcagctgttcccggaggttgacgccgagctggcgacgcgtgattacgacgagag
cctgaccgacaagaacatcgagaagaccttcgtcaacgtcgcgaagccgttccacaaagagcgtgtggcccaaag
cctgatcgtcccgaccaacacgggcaacatgtataccgcgtctgtctacgcggcattcgcgagcctgctgaatta
cgtcggttctgacgacctgcagggcaagcgcgttggcctgttcagctacggtagcggcttagcggccagcctgta
tagctgcaaaattgtcggcgacgtccagcacatcatcaaggagctggacatcaccaacaagctggcgaagcgcat
caccgagacgccgaaagattacgaggcagcgatcgagttacgcgagaatgcgcatctgaagaagaacttcaagcc
gcaaggtagcatcgagcacctgcagagcggcgtctactacctgacgaacattgacgacaagttccgccgttctta
tgacgtcaaaaagtaactagtaggaggaaaacatcatggtgctgacgaacaaaaccgtcattagcggcagcaagg
tgaagtctctgagcagcgcccaaagctctagcagcggccccgtctagcagcagcgaggaggacgacagccgtgaca
ttgagtctctggacaagaagatccgcccgctggaggagttagaggccctgctgagcagcggcaacaccaagcagc
tgaagaacaaggaagttgcagcgctggtgatccacggtaagctgccactgtatgcgctggaaaagaaactgggcg
atacgacgcgtgcggtcgcggtgcgtcgcaaagccttaagcatcttagcggaggccccggtgttagccagcgacc
gcctgccgtacaagaactacgactacgaccgcgtgtttggcgcgtgctgcgagaatgtcattggctacatgccgt
taccggttggtgtgatcggcccgctggtcattgatggcacgagctatcacattccaatggcgaccacggaaggtt
gcttagtcgccagcgccatgcgtggctgtaaggcgattaacgccggcggtggcgcgacgaccgtgttaaccaagg
atggtatgacgcgcggtccggtcgtccgcttcccaacgctgaagcgcagcggcgcgtgtaagatttggctggatt
ctgaggagggccaaaacgcgatcaagaaagccttcaactctacgagccgtttcgcgcgtttacagcatatccaga
cctgcctggccggcgacctgctgttcatgcgcttccgcaccaccacgggcgatgcgatgggcatgaacatgatca
gcaagggcgtcgaatatagcctgaaacaaatggtggaagaatatggctggaggacatggaggttgtctctgtga
gcggcaactattgcaccgacaagaagccggcagccattaactggattgagggtcgcggcaaaagcgtcgtggcag
aagcgaccatcccaggcgacgtggtccgtaaggttctgaagagcgacgtcagcgccctggttgagttaaatatcg
cgaaaaacctggtcggcagcgcgatggcgggcagcgtgggtggctttaacgcacatgcagcgaatctggttacgg
cggttttcttagccttaggtcaggacccagcccaaaatgtcgagagcagcaactgcattaccttaatgaaagagg
ttgacggtgacctgcgcatcagcgtttctatgccgtctatcgaggtcggcacgatcggcggcggcaccgttttag
aaccgcaaggtcgatgctggatctgctgggcgtgcgcggcccacatgcaacgcccaggcaccaatgcccgcc
aactggcccgtatcgtggcctgcgcggttctggcgggtgagctgagcctgtgcgccgcattagccgcgggccatt
```

FIG. 21C

```
tagttcaatctcacatgacccacaaccgcaagccggcagaaccaaccaagccaaataacctggacgcaaccgaca
ttaaccgtctgaaggatggcagcgtcacgtgcattaaaagctgaggatctccaggcatcaaataaaacgaaaggc
tcagtcgaaagactgggcctttcgttttatctgttgtttgtcggtgaacgctctctactagagtcacactggctc
accttcgggtgggcctttctgcgtttatagcgaattgatctggtttgacagcttatcatcgactgcacggtgcac
caatgcttctggcgtcaggcagccatcggaagctgtggtatggctgtgcaggtcgtaaatcactgcataattcgt
gtcgctcaaggcgcactcccgttctggataatgttttttgcgccgacatcataacggttctggcaaatattctga
aatgagctgttgacaattaatcatccggctcgtataatgtgtggaattgtgagcggataacaatttcaggatcta
ggaggaaataaccatgtctctgccattcctgacgtctgcgccaggtaaggtgatcatcttcggcgagcactctgc
ggtgtacaataagccggccgtcgccgcctctgtgtctgcgttacgcacctacctgctgatcagcgaatcttctgc
accggacacgatcgagctggactttccggacatcagcttcaaccacaagtggagcatcaacgacttcaacgcgat
cacggaggaccaggtgaacagccaaaagctggccaaagcccagcaagcaacgacggtctgtctcaggagctggt
gtctctgctggaccgctgttagcgcagttaagcgagagcttccattaccacgccgcgttctgcttcctgtacat
gttcgtttgcctgtgcccgcacgcaaagaacatcaagttcagcctgaagagcacgctgccgattggcgcaggctt
aggctctagcgcatctatcagcgtgagcctggcgctggcgatggcctatctgggtggcctgattggcagcaacga
cctggagaaactgagcgaaaacgacaagcacatcgtgaaccagtgggcctttatcggcgagaagtgcattcatgg
cacccgagcggcattgacaacgcagttgccacgtatgcaacgccctgctgttcgagaagacagccacaacgg
cacgatcaacacgaacaacttcaagttcctggacgacttccggcgatccgatgattctgacctacacccgtat
cccacgcagcaccaaggatttagtcgcccgcgtgcgtgttagtcaccgaaaagttcccggaggtgatgaagcc
gatcctggacgcgatgggcgagtgcgcgctgcagggtctggagatcatgaccaagctgagcaagtgcaagggcac
cgacgatgaggcggtggagaccaacaatgagctgtacgagcagctgctggagctgatccgtatcaatcacgcct
gctggtctctatcggtgtgtctcaccggggcctggaactgatcaaaaacctgagcgacgacctgcgcattggctc
tacgaaattaacgggtgcaggtggcggtggctgctctttaacgctgctgcgccgtgacattacgcaggagcaaat
cgacagcttcaagaagaagctgcaggacgacttcagctacgagacgttcgagacggacctgggcggcacgggctg
ttgcctgctgagcgccaaaaatctgaacaaggacctgaagatcaaaagcctggtgttccagctgttcgaaaacaa
gacgaccacgaagcagcagatcgacgacctgttactgccgggtaacaccaatctgccgtggacgtcttaaggatc
taggagggagatcatatgagcgaattacgtgcattcagcgcgccaggtaaggcactgctggccggtggctacctg
gtgttagacaccaagtacgaggcgttcgtcgtcggcttatctgcccgtatgcatgcagttgcccaccgtatggt
agcctgcagggctctgacaagttcgaagtgcgtgtgaagagcaagcagttcaaggacggcgagtggctgtaccac
attagcccaaagagcggcttcatcccggttagcattggtggcagcaagaacccatttatcgagaaggtcattgcc
aacgtcttcagctacttcaagccgaatatggacgattactgcaaccgcaacctgttcgtcatcgacattttcagc
gacgacgcgtaccacagccaagaggactctgttacggagcatcgtggtaaccgccgcctgagcttccacagccat
cgcattgaggaggtgccgaagacgggtctgggttctagcgccggtttagttaccgtcttaacgacggcgttagcg
agcttcttcgtgagcgacctggagaacaacgtggacaagtaccgcgaagtgattcataacctggcgcaggtggca
cattgtcaggcccaaggtaagattggctctggttttgatgtggcagcggccgcctatggctctatccgctatcgc
cgctttccgccggccctgatcagcaatctgccggacatcggctctgcgacgtatggtagcaaactggcgcatctg
gtggacgaagaagactggaacatcaccattaagtctaatcacctgccgagcggcttaacgttatggatgggcgat
atcaagaacggcagcgaaacggttaagctggtgcagaaagtgaaaaactggtacgacagccacatgccggaaagc
ctgaagatttacacggagctggaccacgccaatagccgtttcatggatggtctgagcaagctggaccgcctgcac
```

FIG. 21D gaaacccacgacgactacagcgaccaaatcttcgagagcctggagcgcaatgactgcacctgccagaagtacccg
gagatcacggaggtccgcgatgccgtggcaacgattcgccgtagcttccgcaaaattacgaaggagagcggcgcg
gatatcgaaccaccggtccagacgtctctgctggacgactgtcaaaccttaaagggcgtgttaacgtgcctgatt
ccgggcgcgggtggttacgacgccattgccgtcatcacgaaacaggacgtcgatctgcgcgcacaaacggccaac
gacaaacgtttcagcaaagtccaatggctggatgttacgcaggccgactgggtgttcgcaaggagaaggacccg
gaaacgtatctggataagtgaggatctaggaggattatgagatgaccgtttacacagcatccgttaccgcacccg
tcaacatcgcaacccttaagtattggggaaaagggacacgaagttgaatctgccaccaattcgtccatatcag
tgactttatcgcaagatgacctcagaacgttgacctctgcggctactgcacctgagtttgaacgcgacactttgt
ggttaaatggagaaccacacagcatcgacaatgaaagaactcaaaattgtctgcgcgacctacgccaattaagaa
aggaaatggaatcgaaggacgcctcattgcccacattatctcaatgaaactccacattgtctccgaaaataact
ttcctacagcagctggtttagcttcctccgctgctggctttgctgcattggtctctgcaattgctaagttatacc
aattaccacagtcaacttcagaaatatctagaatagcaagaaagggtctggttcagcttgtagatcgttgtttg
gcggatacgtggcctgggaaatgggaaaagctgaagatggtcatgattccatggcagtacaaatcgcagacagct
ctgactggcctcagatgaaagcttgtgtcctagttgtcagcgatattaaaaaggatgtgagttccactcagggta
tgcaattgaccgtggcaacctccgaactatttaaagaaagaattgaacatgtcgtaccaaagagatttgaagtca
tgcgtaaagccattgttgaaaaagatttcgccaccctttgcaaaggaaacaatgatggattccaactctttccatg
ccacatgtttggactctttccctccaatattctacatgaatgacacttccaagcgtatcatcagttggtgccaca
ccattaatcagttttacggagaaacaatcgttgcatacacgtttgatgcaggtccaaatgctgtgttgtactact
tagctgaaaatgagtcgaaactctttgcatttatctataaattgtttggctctgttcctggatgggacaagaaat
ttactactgagcagcttgaggctttcaaccatcaatttgaatcatctaactttactgcacgtgaattggatcttg
agttgcaaaaggatgttgccagagtgattttaactcaagtcggttcaggcccacaagaaacaaacgaatctttga
ttgacgcaaagactggtctaccaaaggaataaggatctaggaggtaatgataatgcaaacggaacacgtcattt
attgaatgcacagggagttccacgggtacgctggaaaagtatgccgcacacacggcagacacccgcttacatct
cgcgttctccagttggctgtttaatgccaaaggacaattattagttacccgccgcgcactgagcaaaaagcatg
gcctggcgtgtggactaactcggtttgtgggcacccacaactgggagaaagcaacgaagacgcagtgatccgcg
ttgccgttatgagcttggcgtggaaattacgcctcctgaatctatctatcctgactttcgctaccgcgccaccga
tccgagtggcattgtggaaaatgaagtgtgtccggtatttgccgcacgcaccactagtgcgttacagatcaatga
tgatgaagtgatggattatcaatggtgtgatttagcagatgtattacacggtattgatgccacgccgtgggcgtt
cagtccgtggatggtgatgcaggcgacaaatcgcgaagccagaaaacgattatctgcatttacccagcttaaata
agGAtcttttaagaaggagatatacatATGGTGGAATTTGATTTTAACAAATATATGGATAGCAAAGCGATGACC
GTGAACGAAGCGCTGAACAAAGCGATTCCGCTGCGCTATCCGCAGAAAATTTATGAAAGCATGCGCTATAGCCTG
CTGGCGGGCGGCAAACGCGTGCGCCCGGTGCTGTGCATTGCCGCGTGCGAACTGGTGGGCGGCACCGAAGAACTG
GCGATTCCGACCGCGTGCGCGATTGAAATGATTCATACCATGAGCCTGATGCATGATGATCTGCCGTGCATTGAT
AACGATGATCTGCGCCCGCGCAAACCGACCAACCATAAAATTTTTGGCGAAGATACCGCGGTGACCGCGGGCAAC
GCGCTGCATAGCTATGCGTTTGAACATATTGCGGTGAGCACCAGCAAAACCGTGGGCGCGGATCGCATTCTGCGC
ATGGTGAGCGAACTGGGCCGCGCGACCGGCAGCGAAGGCGTGATGGGCGGCCAGATGGTGGATATTGCGAGCGAA
GGCGATCCGAGCATTGATCTGCAGACCCTGGAATGGATTCATATTCATAAAACCGCGATGCTGCTGGAATGCAGC
GTGGTGTGCGGCGCGATTATTGGCGGCGCGAGCGAAATTGTGATTGAACGCGCGCGCCGCTATGCGCGCTGCGTG

FIG. 21E

```
GGCCTGCTGTTTCAGGTGGTGGATGATATTCTGGATGTGACCAAAAGCAGCGATGAACTGGGCAAAACCGCGGGC
AAAGATTTAATTAGCGATAAAGCGACCTATCCGAAACTGATGGGCCTGGAAAAAGCGAAAGAATTTAGCGATGAA
CTGCTGAACCGCGCGAAAGGCGAACTGAGCTGCTTTGATCCGGTGAAAGCGGCGCCGCTGCTGGGCCTGGCGGAT
TATGTGGCGTTTCGCCAGAACTAAGGATCCaaactcgagtaaggatctccaggcatcaaataaaacgaaaggctc
agtcgaaagactgggcctttcgttttatctgttgtttgtcggtgaacgctctctactagagtcacactggctcac
cttcgggtgggccttttctgcgtttatacctaggatatattccgcttcctcgctcactgactcgctacgctcggt
cgttcgactgcggcgagcggaaatggcttacgaacggggcggagatttcctggaagatgccaggaagatacttaa
cagggaagtgagagggccgcggcaaagccgttttttccataggctccgcccccctgacaagcatcacgaaatctga
cgctcaaatcagtggtggcgaaacccgacaggactataaagataccaggcgtttccccctggcggctccctcgtg
cgctctcctgttcctgcctttcggtttaccggtgtcattccgctgttatggccgcgtttgtctcattccacgcct
gacactcagttccgggtaggcagttcgctccaagctggactgtatgcacgaaccccccgttcagtccgaccgctg
cgccttatccggtaactatcgtcttgagtccaacccggaaagacatgcaaaagcaccactggcagcagccactgg
taattgatttagaggagttagtcttgaagtcatgcgccggttaaggctaaactgaaaggacaagttttggtgact
gcgctcctccaagccagttacctcggttcaaagagttggtagctcagagaaccttcgaaaaaccgccctgcaagg
cggttttttcgttttcagagcaagagattacgcgcagaccaaaacgatctcaagaagatcatcttattaatcaga
taaaatatttctagatttcagtgcaatttatctcttcaaatgtagcacctgaagtcagccccatacgatataagt
tgttactagtgcttggattctcaccaataaaaaacgcccggcggcaaccgagcgttctgaacaaatccagatgga
gttctgaggtcattactggatctatcaacaggagtccaagcgagctcgatatcaaattacgccccgccctgccac
tcatcgcagtactgttgtaattcattaagcattctgccgacatggaagccatcacaaacggcatgatgaacctga
atcgccagcggcatcagcaccttgtcgccttgcgtataatatttgcccatggtgaaaacggggcgaagaagttg
tccatattggccacgtttaaatcaaaactggtgaaactcacccagggattggctgagacgaaaaacatattctca
ataaacccttagggaataggccaggttttcaccgtaacacgccacatcttgcgaatatatgtgtagaaactgc
cggaaatcgtcgtggtattcactccagagcgatgaaaacgtttcagtttgctcatggaaaacggtgtaacaaggg
tgaacactatcccatatcaccagctcaccgtctttcattgccatacgaaattccggatgagcattcatcaggcgg
gcaagaatgtgaataaaggccggataaaacttgtgcttatttttctttacggtcttttaaaaaggccgtaatatcc
agctgaacggtctggttataggtacattgagcaactgactgaaatgcctcaaaatgttctttacgatgccattgg
gatatatcaacggtggtatatccagtgatttttttctccatttttagcttccttagctcctgaaaatctcgataac
tcaaaaatacgcccggtagtgatcttatttcattatggtgaaagttggaacctcttacgtgccgatcaacgtct
cattttcgccagatatc
```

FIG. 22A

```
gacgtcgacaccatcgaatggtgcaaaacctttcgcggtatggcatgatagcgcccggaagagagtcaattcagg
gtggtgaatgtgaaaccagtaacgttatacgatgtcgcagagtatgccggtgtctcttatcagaccgtttcccgc
gtggtgaaccaggccagccacgtttctgcgaaaacgcgggaaaaagtggaagcggcgatggcggagctgaattac
attcccaaccgcgtggcacaacaactggcgggcaaacagtcgttgctgattggcgttgccacctccagtctggcc
ctgcacgcgccgtcgcaaattgtcgcggcgattaaatctcgcgccgatcaactgggtgccagcgtggtggtgtcg
atggtagaacgaagcggcgtcgaagctgtaaagcggcggtgcacaatcttctcgcgcaacgcgtcagtgggctg
atcattaactatccgctggatgaccaggatgccattgctgtggaagctgcctgcactaatgttccggcgttattt
cttgatgtctctgaccagacacccatcaacagtattattttctcccatgaagacggtacgcgactggcgtggag
catctggtcgcattgggtcaccagcaaatcgcgctgttagcggcccattaagttctgtctcggcgcgtctgcgt
ctggctggctggcataaatatctcactcgcaatcaaattcagccgatagcggaacgggaaggcgactggagtgcc
atgtccggttttcaacaaaccatgcaaatgctgaatgagggcatcgttcccactgcgatgctggttgccaacgat
cagatggcgctggcgcaatgcgcgccattaccgagtcgggctgcgcgttggtgcggatatctcggtagtggga
tacgacgataccgaagacagctcatgttatatcccgccgttaaccaccatcaaacaggatttcgcctgctgggg
caaaccagcgtggaccgcttgctgcaactctctcagggccaggcggtgaagggcaatcagctgttgcccgtctca
ctggtgaaaagaaaaaccacctggcgcccaatacgcaaaccgcctctcccgcgcgttggccgattcattaatg
cagctggcacgacaggtttcccgactggaaagcgggcagtgagcgcaacgcaattaatgtaagttagcgcgaatt
gatctggtttgacagcttatcatcgactgcacggtgcaccaatgcttctggcgtcaggcagccatcggaagctgt
ggtatggctgtgcaggtcgtaaatcactgcataattcgtgtcgctcaaggcgcactcccgttctggataatgttt
tttgcgccgacatcataacggttctggcaaatattctgaaatgagctgttgacaattaatcatccggctcgtata
atgtgtggaattgtgagcggataacaatttcagaattcaaaAGATCTtttaagaaggagatatacatATGCGTCG
TAGCGCAAATTATCAGCCGAGCATTTGGAATCATGATTATATTGAAAGCCTGCGTATTGAATATGTTGGTGAAAC
CTGTACCCGTCAGATTAATGTTCTGAAAGAACAGGTTCGTATGATGCTGCATAAAGTTGTTAATCCGCTGGAACA
GCTGGAACTGATTGAAATTCTGCAGCGTCTGGGTCTGAGCTATCATTTTGAAGAAGAAATTAAACGTATTCTGGA
TGGTGTTTATAATAATGATCATGGTGGTGATACCTGGAAAGCAGAAAATCTGTATGCAACCGCACTGAAATTTCG
TCTGCTGCGTCAGCATGGTTATAGCGTTAGCCAGGAAGTTTTTAATAGCTTTAAAGATGAACGTGGTAGCTTTAA
AGCATGTCTGTGTGAAGATACCAAAGGTATGCTGAGCCTGTATGAAGCAAGCTTTTTTCTGATTGAAGGTGAAAA
TATTCTGGAAGAAGCACGTGATTTTAGCACCAAACATCTGGAAGAATATGTTAAACAGAATAAAGAAAAAAATCT
GGCAACCCTGGTTAATCATAGCCTGGAATTTCCGCTGCATTGGCGTATGCCGCGTCTGGAAGCACGTTGGTTTAT
TAATATTTATCGTCATAATCAGGATGTTAATCCGATTCTGCTGGAATTTGCAGAACTGGATTTAATATTGTTCA
GGCAGCACATCAGGCAGATTTAAAACAGGTTAGCACCTGGTGGAAAAGCACCGGTCTGGTTGAAAATCTGAGCTT
TGCACGTGATCGTCCGGTTGAAAATTTTTTTTGGACCGTTGGTCTGATTTTTCAGCCGCAGTTTGGTTATTGTCG
TCGTATGTTTACCAAAGTTTTTGCACTGATTACCACCATTGATGATGTTTATGATGTTTATGGTACCCTGGATGA
ACTGGAACTGTTTACCGATGTTGTTGAACGTTGGGATATTAATGCAATGGATCAGCTGCCGGATTATATGAAAAT
TTGTTTTCTGACCCTGCATAATAGCGTTAATGAAATGGCACTGGATACCATGAAAGAACAGCGTTTTCATATTAT
TAAATATCTGAAAAAAGCATGGGTTGATCTGTGTCGTTATTATCTGGTGAAGCAAAATGGTATAGCAATAAATA
TCGTCCGAGCCTGCAGGAATATATTGAAAATGCATGGATTAGCATTGGTGCACCGACCATTCTGGTTCATGCATA
TTTTTTTGTTACCAATCCGATTACCAAAGAAGCACTGGATTGTCTGGAAGAATATCCGAATATTATTCGTTGGAG
CAGCATTATTGCACGTCTGGCAGATGATCTGGGTACCAGCACCGATGAACTGAAACGTGGTGATGTTCCGAAAGC
```

FIG. 22B

```
AATTCAGTGTTATATGAATGAAACCGGTGCAAGCGAAGAAGGTGCACGTGAATATATTAAATATCTGATTAGCGC
AACCTGGAAAAAAATGAATAAAGATCGTGCAGCAAGCAGCCCGTTTAGCCATATTTTTATTGAAATTGCACTGAA
TCTGGCACGTATGGCACAGTGTCTGTATCAGCATGGTGATGGTCATGGTCTGGGTAATCGTGAAACCAAAGATCG
TATTCTGAGCCTGCTGATTCAGCCGATTCCGCTGAATAAAGATTAAGGATCCaaactcgagtaaggatctccagg
catcaaataaaacgaaaggctcagtcgaaagactgggcctttcgttttatctgttgtttgtcggtgaacgctctc
tactagagtcacactggctcaccttcgggtgggcctttctgcgtttatacctagggcgttcggctgcggcgagcg
gtatcagctcactcaaaggcggtaatacggttatccacagaatcaggggataacgcaggaaagaacatgtgagca
aaaggccagcaaaaggccaggaaccgtaaaaaggccgcgttgctggcgtttttccataggctccgcccccctgac
gagcatcacaaaaatcgacgctcaagtcagaggtggcgaaacccgacaggactataaagataccaggcgtttccc
cctggaagctccctcgtgcgctctcctgttccgaccctgccgcttaccggatacctgtccgcctttctcccttcg
ggaagcgtggcgctttctcatagctcacgctgtaggtatctcagttcggtgtaggtcgttcgctccaagctgggc
tgtgtgcacgaaccccccgttcagcccgaccgctgcgccttatccggtaactatcgtcttgagtccaacccggta
agacacgacttatcgccactggcagcagccactggtaacaggattagcagagcgaggtatgtaggcggtgctaca
gagttcttgaagtggtggcctaactacggctacactagaaggacagtatttggtatctgcgctctgctgaagcca
gttaccttcggaaaaagagttggtagctcttgatccggcaaacaaaccaccgctggtagcggtggtttttttgtt
tgcaagcagcagattacgcgcagaaaaaaaggatctcaagaagatcctttgatcttttctacggggtctgacgct
cagtggaacgaaaactcacgttaagggattttggtcatgactagtgcttggattctcaccaataaaaaacgcccg
gcggcaaccgagcgttctgaacaaatccagatggagttctgaggtcattactggatctatcaacaggagtccaag
cgagctcgtaaacttggtctgacagttaccaatgcttaatcagtgaggcacctatctcagcgatctgtctatttc
gttcatccatagttgcctgactccccgtcgtgtagataactacgatacgggagggcttaccatctggccccagtg
ctgcaatgataccgcgagacccacgctcaccggctccagatttatcagcaataaaccagccagccggaagggccg
agcgcagaagtggtcctgcaactttatccgcctccatccagtctattaattgttgccgggaagctagagtaagta
gttcgccagttaatagtttgcgcaacgttgttgccattgctacaggcatcgtggtgtcacgctcgtcgtttggta
tggcttcattcagctccggttcccaacgatcaaggcgagttacatgatcccccatgttgtgcaaaaaagcggtta
gctccttcggtcctccgatcgttgtcagaagtaagttggccgcagtgttatcactcatggttatggcagcactgc
ataattctcttactgtcatgccatccgtaagatgcttttctgtgactggtgagtactcaaccaagtcattctgag
aatagtgtatgcggcgaccgagttgctcttgcccggcgtcaatacgggataatacgcgccacatagcagaactt
taaaagtgctcatcattggaaaacgttcttcggggcgaaaactctcaaggatcttaccgctgttgagatccagtt
cgatgtaacccactcgtgcacccaactgatcttcagcatcttttactttcaccagcgtttctgggtgagcaaaaa
caggaaggcaaaatgccgcaaaaaagggaataagggcgacacggaaatgttgaatactcatactcttcctttttc
aatattattgaagcatttatcaggttattgtctcatgagcggatacatatttgaatgtatttagaaaaataaac
aaatagggggttccgcgcacatttccccgaaaagtgccacct
```

FIG. 23A

```
gacgtcgacaccatcgaatggtgcaaaacctttcgcggtatggcatgatagcgcccggaagagagtcaattcagg
gtggtgaatgtgaaaccagtaacgttatacgatgtcgcagagtatgccggtgtctcttatcagacgtttcccgc
gtggtgaaccaggccagccacgtttctgcgaaaacgcgggaaaaagtggaagcggcgatggcggagctgaattac
attcccaaccgcgtggcacaacaactggcgggcaaacagtcgttgctgattggcgttgccacctccagtctggcc
ctgcacgcgccgtcgcaaattgtcgcggcgattaaatctcgcgccgatcaactgggtgccagcgtggtggtgtcg
atggtagaacgaagcggcgtcgaagcctgtaaagcggcggtgcacaatcttctcgcgcaacgcgtcagtgggctg
atcattaactatccgctggatgaccaggatgccattgctgtggaagctgcctgcactaatgttccggcgttattt
cttgatgtctctgaccagacaccatcaacagtattattttctcccatgaagacggtacgcgactgggcgtggag
catctggtcgcattgggtcaccagcaaatcgcgctgttagcgggccattaagttctgtctcggcgcgtctgcgt
ctggctggctggcataaatatctcactcgcaatcaaattcagccgatagcggaacgggaaggcgactggagtgcc
atgtccggttttcaacaaaccatgcaaatgctgaatgagggcatcgttcccactgcgatgctggttgccaacgat
cagatggcgctgggcgcaatgcgcgccattaccgagtccgggctgcgcgttggtgcggatatctcggtagtggga
tacgacgataccgaagacagctcatgttatatcccgccgttaaccaccatcaaacaggattttcgcctgctgggg
caaaccagcgtggaccgcttgctgcaactctctcagggccaggcggtgaagggcaatcagctgttgcccgtctca
ctggtgaaaagaaaaaccaccctggcgcccaatacgcaaaccgcctctcccgcgcgttggccgattcattaatg
cagctggcacgacaggtttcccgactggaaagcgggcagtgagcgcaacgcaattaatgtaagttagcgcgaatt
gatctggtttgacagcttatcatcgactgcacggtgcaccaatgcttctggcgtcaggcagccatcggaagctgt
ggtatggctgtgcaggtcgtaaatcactgcataattcgtgtcgctcaaggcgcactcccgttctggataatgttt
tttgcgccgacatcataacggttctggcaaatattctgaaatgagctgttgacaattaatcatccggctcgtata
atgtgtggaattgtgagcggataacaatttcagaattcaaaAGAtcttttaagaaggagatatacatATGGTGGA
ATTTGATTTTAACAAATATATGGATAGCAAAGCGATGACCGTGAACGAAGCGCTGAACAAAGCGATTCCGCTGCG
CTATCCGCAGAAAATTTATGAAAGCATGCGCTATAGCCTGCTGGCGGGCGGCAAACGCGTGCGCCCGGTGCTGTG
CATTGCGGCGTGCGAACTGGTGGGCGGCACCGAAGAACTGGCGATTCCGACCGCGTGCGCGATTGAAATGATTCA
TACCATGAGCCTGATGCATGATGATCTGCCGTGCATTGATAACGATGATCTGCGCCCGCGGCAAACCGACCAACCA
TAAAATTTTTGGCGAAGATACCGCGGTGACCGCGGGCAACGCGCTGCATAGCTATGCGTTTGAACATATTGCGGT
GAGCACCAGCAAAACCGTGGGCGCGGATCGCATTCTGCGCATGGTGAGCGAACTGGGCCGCGCGACCGGCAGCGA
AGGCGTGATGGGCGGCCAGATGGTGGATATTGCGAGCGAAGGCGATCCGAGCATTGATCTGCAGACCCTGGAATG
GATTCATATTCATAAAACCGCGATGCTGCTGGAATGCAGCGTGGTGTGCGGCGCGATTATTGGCGGCGCGAGCGA
AATTGTGATTGAACGCGCGCGCCGCTATGCGCGCTGCGTGGGCCTGCTGTTTCAGGTGGTGGATGATATTCTGGA
TGTGACCAAAAGCAGCGATGAACTGGGCAAAACCGCGGGCAAAGATTTAATTAGCGATAAAGCGACCTATCCGAA
ACTGATGGGCCTGGAAAAAGCGAAAGAATTTAGCGATGAACTGCTGAACCGCGCGAAAGCGAACTGAGCTGCTT
TGATCCGGTGAAAGCGGCGCCGCTGCTGGCCTGGCGGATTATGTGGCGTTTCGCCAGAACTAAGGATCTtttaa
gaaggagatatacatATGCGTCGTAGCGCAAATTATCAGCCGAGCATTTGGAATCATGATTATATTGAAAGCCTG
CGTATTGAATATGTTGGTGAAACCTGTACCCGTCAGATTAATGTTCTGAAAGAACAGGTTCGTATGATGCTGCAT
AAAGTTGTTAATCCGCTGGAACAGCTGGAACTGATTGAAATTCTGCAGCGTCTGGGTCTGAGCTATCATTTTGAA
GAAGAAATTAAACGTATTCTGGATGGTGTTTATAATAATGATCATGGTGGTGATACCTGGAAAGCAGAAAATCTG
TATGCAACCGCACTGAAATTTCGTCTGCTGCGTCAGCATGGTTATAGCGTTAGCCAGGAAGTTTTTAATAGCTTT
AAAGATGAACGTGGTAGCTTTAAAGCATGTCTGTGTGAAGATACCAAAGGTATGCTGAGCCTGTATGAAGCAAGC
```

FIG. 23B

```
TTTTTTCTGATTGAAGGTGAAAATATTCTGGAAGAAGCACGTGATTTTAGCACCAAACATCTGGAAGAATATGTT
AAACAGAATAAAGAAAAAAATCTGGCAACCCTGGTTAATCATAGCCTGGAATTTCCGCTGCATTGGCGTATGCCG
CGTCTGGAAGCACGTTGGTTTATTAATATTTATCGTCATAATCAGGATGTTAATCCGATTCTGCTGGAATTTGCA
GAACTGGATTTTAATATTGTTCAGGCAGCACATCAGGCAGATTTAAAACAGGTTAGCACCTGGTGGAAAAGCACC
GGTCTGGTTGAAAATCTGAGCTTTGCACGTGATCGTCCGGTTGAAAATTTTTTTTGGACCGTTGGTCTGATTTTT
CAGCCGCAGTTTGGTTATTGTCGTCGTATGTTTACCAAAGTTTTTGCACTGATTACCACCATTGATGATGTTTAT
GATGTTTATGGTACCCTGGATGAACTGGAACTGTTTACCGATGTTGTTGAACGTTGGGATATTAATGCAATGGAT
CAGCTGCCGGATTATATGAAAATTTGTTTTCTGACCCTGCATAATAGCGTTAATGAAATGGCACTGGATACCATG
AAAGAACAGCGTTTTCATATTATTAAATATCTGAAAAAAGCATGGGTTGATCTGTGTCGTTATTATCTGGTTGAA
GCAAAATGGTATAGCAATAAATATCGTCCGAGCCTGCAGGAATATATTGAAAATGCATGGATTAGCATTGGTGCA
CCGACCATTCTGGTTCATGCATATTTTTTGTTACCAATCCGATTACCAAAGAAGCACTGGATTGTCTGGAAGAA
TATCCGAATATTATTCGTTGGAGCAGCATTATTGCACGTCTGGCAGATGATCTGGGTACCAGCACCGATGAACTG
AAACGTGGTGATGTTCCGAAAGCAATTCAGTGTTATATGAATGAAACCGGTGCAAGCGAAGAAGGTGCACGTGAA
TATATTAAATATCTGATTAGCGCAACCTGGAAAAAAATGAATAAAGATCGTGCAGCAAGCAGCCCGTTTAGCCAT
ATTTTTATTGAAATTGCACTGAATCTGGCACGTATGGCACAGTGTCTGTATCAGCATGGTGATGGTCATGGTCTG
GGTAATCGTGAAACCAAAGATCGTATTCTGAGCCTGCTGATTCAGCCGATTCCGCTGAATAAAGATTAAGGATCC
aaactcgagtaaggatctccaggcatcaaataaaacgaaaggctcagtcgaaagactgggcctttcgttttatct
gttgtttgtcggtgaacgctctctactagagtcacactggctcaccttcgggtgggcctttctgcgtttatacct
agggcgttcggctgcggcgagcggtatcagctcactcaaaggcggtaatacggttatccacagaatcaggggata
acgcaggaaagaacatgtgagcaaaaggccagcaaaaggccaggaaccgtaaaaaggccgcgttgctggcgtttt
tccataggctccgcccccctgacgagcatcacaaaaatcgacgctcaagtcagaggtggcgaaacccgacaggac
tataaagataccaggcgtttccccctggaagctccctcgtgcgctctcctgttccgaccctgccgcttaccggat
acctgtccgcctttctcccttcgggaagcgtggcgctttctcatagctcacgctgtaggtatctcagttcggtgt
aggtcgttcgctccaagctgggctgtgtgcacgaaccccccgttcagcccgaccgctgcgccttatccggtaact
atcgtcttgagtccaacccggtaagacacgacttatcgccactggcagcagccactggtaacaggattagcagag
cgaggtatgtaggcggtgctacagagttcttgaagtggtggcctaactacggctacactagaaggacagtatttg
gtatctgcgctctgctgaagccagttaccttcggaaaaagagttggtagctcttgatccggcaaacaaaccaccg
ctggtagcggtggtttttttgtttgcaagcagcagattacgcgcagaaaaaaaggatctcaagaagatcctttga
tcttttctacggggtctgacgctcagtggaacgaaaactcacgttaagggattttggtcatgactagtgcttgga
ttctcaccaataaaaaacgcccggcggcaaccgagcgttctgaacaaatccagatggagttctgaggtcattact
ggatctatcaacaggagtccaagcgagctcgtaaacttggtctgacagttaccaatgcttaatcagtgaggcacc
tatctcagcgatctgtctatttcgttcatccatagttgcctgactccccgtcgtgtagataactacgatacggga
gggcttaccatctggccccagtgctgcaatgataccgcgagacccacgctcaccggctccagatttatcagcaat
aaaccagccagccggaagggccgagcgcagaagtggtcctgcaactttatccgcctccatccagtctattaattg
ttgccgggaagctagagtaagtagttcgccagttaatagtttgcgcaacgttgttgccattgctacaggcatcgt
ggtgtcacgctcgtcgtttggtatggcttcattcagctccggttcccaacgatcaaggcgagttacatgatcccc
catgttgtgcaaaaaagcggttagctccttcggtcctccgatcgttgtcagaagtaagttggccgcagtgttatc
actcatggttatggcagcactgcataattctcttactgtcatgccatccgtaagatgcttttctgtgactggtga
```

FIG. 23C

```
cttaccgctgttgagatccagttcgatgtaacccactcgtgcacccaactgatcttcagcatcttttactttcac
cagcgtttctgggtgagcaaaaacaggaaggcaaaatgccgcaaaaagggaataagggcgacacggaaatgttg
aatactcatactcttccttttttcaatattattgaagcatttatcagggttattgtctcatgagcggatacatatt
tgaatgtatttagaaaaataaacaatagggqttccgcgcacatttccccgaaaagtgccacct
```

VECTORS AND STRAINS FOR PRODUCING MYRCENE AND METHOD OF PRODUCING MYRCENE USING THE SAME

FIELD OF THE INVENTION

Disclosed herein is an expression vector capable of expressing myrcene. Also disclosed herein are a strain transformed with the vector and having improved capability of producing myrcene and a method for producing myrcene and a method for recycling glycerol using the same.

CROSS-REFERENCE TO RELATED APPLICATION

This application claims priority to Korean Patent Application No. 10-2015-0097250, filed on Jul. 8, 2015, and all the benefits accruing therefrom under 35 U.S.C. §119, the contents of which in its entirety are herein incorporated by reference.

DESCRIPTION ABOUT NATIONAL SUPPORT RESEARCH AND DEVELOPMENT

This study is made by the support of Cooperative Study Business (Creative Allied Project, CAP) of Korea Ministry of Science, ICT and Future Planning under the supervision of Korea Institute of Science and Technology, and the subject name thereof is Development of technology for producing next generation fuel/material by integrative use of woody biomass (Subject Identification No. CAP-11-1).

BACKGROUND OF THE INVENTION

Monoterpenes are naturally occurring substances which are very important in cosmetic or pharmaceutical industry. Among them, myrcene is a substance that can be used as a starting material for various substances. In particular, it can be widely used as a precursor for menthol or other alcohol substances (e.g., linalool, geraniol). Until now, various myrcene-synthesizing genes have been found in different plants and have been characterized. Nevertheless, the currently available method of producing myrcene is limited only to extraction from plants or pyrolysis of β-pinene.

REFERENCES OF THE RELATED ART

Non-Patent Documents (Non-patent document 1) Sarria S et al., (2014) Microbial Synthesis of Pinene", ACS Synthetic Biology 3, pp. 466-475.

SUMMARY

In an aspect, the present disclosure is directed to providing an expression vector capable of expressing myrcene by transforming *Escherichia coli*.

In another aspect, the present disclosure is directed to providing an *Escherichia coli* strain having improved capability of producing myrcene.

In another aspect, the present disclosure is directed to production of myrcene on a large scale using a transformed *Escherichia coli* strain.

In another aspect, the present disclosure is directed to production and isolation/extraction of strongly volatile myrcene simultaneously.

In another aspect, the present disclosure is directed to production of high value-added myrcene using waste glycerol.

In an aspect, the present disclosure relates to a first vector containing, in sequence, a chloramphenicol resistance gene as a selection marker; a p15A replication origin as a replication origin; a lacUV5 promoter; a first domain containing a gene encoding an enzyme which produces mevalonate from acetyl-CoA; and a second domain containing a gene encoding an enzyme which produces dimethylallyl pyrophosphate (DMAPP) from mevalonate.

In another aspect, the present disclosure relates to a second vector containing, in sequence, an ampicillin resistance gene as a selection marker; a ColE1 replication origin as a replication origin; a trc promoter; and a gene encoding an enzyme which is capable of producing myrcene from geranyl pyrophosphate (GPP).

In another aspect, the present disclosure relates to an *Escherichia coli* strain transformed with the first vector and the second vector.

In another aspect, the present disclosure relates to an *Escherichia coli* strain producing 45 mg/L or more of myrcene in 70 hours under a condition of 37° C. and 1% (w/v) glycerol.

In another aspect, the present disclosure relates to a method for producing myrcene, including a step of cultuirng an *Escherichia coli* strain.

In another aspect, the present disclosure relates to a method for recycling glycerol, including a step of cultuirng an *Escherichia coli* strain.

In another aspect, the present disclosure relates to a kit for producing myrcene.

In an aspect, an *Escherichia coli* strain transformed with the vector of the present disclosure can produce myrcene with high purity on a large scale using glycerol or glucose as a carbon source. The *Escherichia coli* strain is economical because it can produce high value-added myrcene using waste glycerol as a carbon source. Also, it is environment-friendly because the microorganism can remove waste glycerol.

BRIEF DESCRIPTION OF THE DRAWINGS

FIGS. 1A and 1B show depository receipts of transformed *Escherichia coli* strains of the present disclosure.

FIG. 9 shows the sequence of an atoB gene (SEQ ID NO: 1).

FIG. 10 shows the sequence of an HMGS gene (SEQ ID NO: 2).

FIG. 11 shows the sequence of an HMGR gene (SEQ ID NO: 3).

FIG. 12 shows the sequence of an MK gene (SEQ ID NO: 4).

FIG. 13 shows the sequence of a PMK gene (SEQ ID NO: 5).

FIG. 14 shows the sequence of a PMD gene (SEQ ID NO: 6).

FIG. 15 shows the sequence of an IDI gene (SEQ ID NO: 7).

FIG. 16 shows the sequence of a tGPPS gene (SEQ ID NO: 8).

FIG. 17 shows the sequence of a tMS-Qi gene (SEQ ID NO: 9).

FIG. 18A-FIG. 18E show the sequence of a pBbA5c-MevT(co)-MBI(co) plasmid vector (SEQ ID NO: 10), in sequence.

FIG. 19A-FIG. 19E show the sequence of a pBbA5c-MevT(co)-MBIG(co) plasmid vector (SEQ ID NO: 11), in sequence.

FIG. 20A-FIG. 20E show the sequence of a pBbA5c-MevT(co)-T1-MBI(co) plasmid vector (SEQ ID NO: 12), in sequence.

FIG. 21A-FIG. 21E show the sequence of a pBbA5c-MevT(co)-T1-MBIG(co) plasmid vector (SEQ ID NO: 13), in sequence.

FIG. 22A-FIG. 22B show the sequence of a pBbE1a-tMS (co.Qi) plasmid vector (SEQ ID NO: 14), in sequence.

FIGS. 23A-FIG. 23C show the sequence of a pBbE1a-tGPPS2(co)-tMS(co.Qi) plasmid vector (SEQ ID NO: 15), in sequence.

DETAILED DESCRIPTION

Figure 1A:
Figure 2:
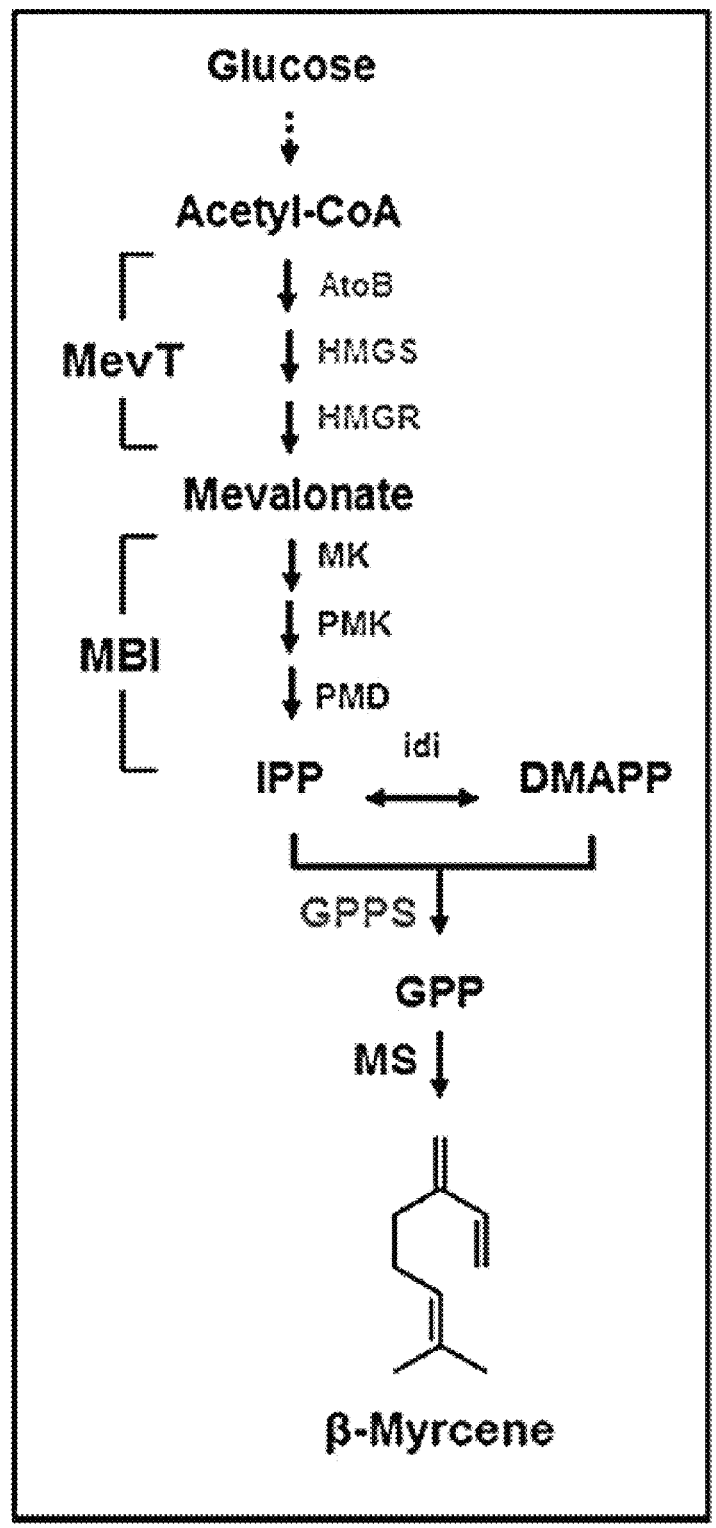
FIG. 2 shows a myrcene production pathway of a transformed *Escherichia coli* strain of the present disclosure.

Hereinafter, the present disclosure is described in detail.

In an aspect, the present disclosure relates to a transformed *Escherichia coli* strain transformed with a first vector and a second vector, the first vector containing, in sequence, a chloramphenicol resistance gene as a selection marker; a p15A replication origin as a replication origin; a lacUV5 promoter; a first domain containing a gene encoding an enzyme which produces mevalonate from acetyl-CoA; and a second domain containing a gene encoding an enzyme which produces dimethylallyl pyrophosphate (DMAPP) from mevalonate, and the second vector containing, in sequence, an ampicillin resistance gene as a selection marker; a ColE1 replication origin as a replication origin; a trc promoter; and a gene encoding an enzyme which is capable of producing myrcene from geranyl pyrophosphate (GPP).

In the present disclosure, a pathway of synthesizing mevalonate from acetyl-CoA is denoted by the acronym MevT, and a pathway of synthesizing isopentenyl diphosphate (IPP) from mevalonate is denoted by the acronym MBI.

In the present disclosure, the first vector is also called a first plasmid or a first plasmid vector, and the second vector is also called a second plasmid or a second plasmid vector.

In this aspect, the first vector may further contain one or more selected from a trc promoter; and a gene encoding an enzyme which is capable of producing geranyl pyrophosphate (GPP) from dimethylallyl pyrophosphate (DMAPP) and isopentenyl diphosphate (IPP). The trc promoter may be located between the first domain and the second domain, and the gene encoding an enzyme which is capable of producing geranyl pyrophosphate (GPP) from dimethylallyl pyrophosphate (DMAPP) and isopentenyl diphosphate (IPP) may be located downstream of the second domain.

In the transformed *Escherichia coli* strain according to an aspect of the present disclosure, the first domain of the first vector may contain, in sequence, a gene encoding acetyl-CoA thiolase (ACAT); a gene encoding 3-hydroxyl-3-methyl-glutaryl-CoA synthase (HMGS); and a gene encoding 3-hydroxyl-3-methyl-glutaryl-CoA reductase (HMGR). In this aspect, the second domain of the first vector may contain, in sequence, a gene encoding mevalonate kinase (MK); a gene encoding phosphomevalonate kinase (PMK); a gene encoding mevalonate diphosphate decarboxylase (PMD); and a gene encoding isopentenyl diphosphate isomerase (IDI).

In this aspect, the enzyme which is capable of producing geranyl pyrophosphate (GPP) from dimethylallyl pyrophosphate (DMAPP) and isopentenyl diphosphate (IPP) may be geranyl pyrophosphate synthase (GPPS).

In the transformed *Escherichia coli* strain according to an aspect of the present disclosure, the gene encoding acetyl-CoA thiolase (hereinafter, atoB gene) may contain a sequence of SEQ ID NO: 1, the gene encoding 3-hydroxyl-3-methyl-glutaryl-CoA synthase (hereinafter, HMGS gene) may contain a sequence of SEQ ID NO: 2, the gene encoding 3-hydroxyl-3-methyl-glutaryl-CoA reductase (hereinafter, HMGR gene) may contain a sequence of SEQ ID NO: 3, the gene encoding mevalonate kinase (hereinafter, MK gene) may contain a sequence of SEQ ID NO: 4, the gene encoding phosphomevalonate kinase (hereinafter, PMK gene) may contain a sequence of SEQ ID NO: 5, the gene encoding mevalonate diphosphate decarboxylase (hereinafter, PMD gene) may contain a sequence of SEQ ID NO: 6, and the gene encoding isopentenyl diphosphate isomerase (hereinafter, IDI gene) may contain a sequence of SEQ ID NO: 7.

And, the gene encoding geranyl pyrophosphate synthase (hereinafter, GPPS or tGPPS gene) may contain a SEQ ID NO: 8.

In the transformed *Escherichia coli* strain according to an aspect of the present disclosure, the first vector may contain a sequence of any of SEQ ID NO: 10, SEQ ID NO: 11, SEQ ID NO: 12, OR SEQ ID NO: 13.

In this aspect, the enzyme which is capable of producing myrcene from geranyl pyrophosphate (GPP) may be myrcene synthase (MS).

And, in the transformed *Escherichia coli* strain according to an aspect of the present disclosure, the second vector may further contain, between the trc promoter and the gene encoding an enzyme which is capable of producing myrcene from geranyl pyrophosphate (GPP), an enzyme which is capable of producing geranyl pyrophosphate (GPP) from dimethylallyl pyrophosphate (DMAPP) and isopentenyl diphosphate (IPP).

The enzyme which is capable of producing geranyl pyrophosphate (GPP) from dimethylallyl pyrophosphate (DMAPP) and isopentenyl diphosphate (IPP) may be geranyl pyrophosphate synthase (GPPS).

In this aspect, the gene encoding myrcene synthase (MS) (hereinafter, MS or tMS gene) may contain a sequence of SEQ ID NO: 9, and the gene encoding geranyl pyrophosphate synthase (GPPS) (hereinafter, GPPS or tGPPS gene) may contain a sequence of SEQ ID NO: 8.

In the transformed *Escherichia coli* strain according to an aspect of the present disclosure, the second vector may contain a sequence of SEQ ID NO: 14 or 15. In the present disclosure, pM1 denotes a first vector containing a chloramphenicol resistance gene, a p15A replication origin, an atoB gene, an HMGS gene and an HMGR gene, and further containing an MK gene, a PMK gene, a PMD gene and an IDI gene, and is also expressed as pBbA5c-MevT(co)-MBI(co). And, in the present disclosure, pM2 denotes a first vector (pM1) further containing a tGPPS gene, and is also expressed as pBbA5c-MevT(co)-MBIG(co). And, in the present disclosure, pM3 denotes a first vector (pM1) further containing a promoter, e.g., a Trc promoter ($P_{Trc}$). The promoter may be located between the HMGR gene and the MK gene. pM3 is also expressed as pBbA5c-MevT(co)-T1-MBI(co). In the present disclosure, pM4 denotes a first vector (pM3) further containing a tGPPS gene, and is also expressed as pBbA5c-MevT(co)-T1-MBIG(co). And, in the present disclosure, pM(Qi) denotes a second vector containing a trc promoter and an MS gene, and is also expressed as pBbE1a-tMS(co.Qi). And, in the present disclosure, pGM (Qi) denotes a second vector (pM(Qi)) further containing a GPPS gene. The GPPS gene may be located between the tMS gene and the promoter. pGM(Qi) is also expressed as pBbE1a-tGPPS2(co)-tMS(co.Qi).

pM1 may contain a sequence of SEQ ID NO: 10, pM2 may contain a sequence of SEQ ID NO: 11, and pM3 may contain a sequence of SEQ ID NO: 13. pM(Qi) may contain a sequence of SEQ ID NO: 14, and pGM(Qi) may contain a sequence of SEQ ID NO: 15.

The vectors according to an aspect of the present disclosure may be those described in Table 1.

TABLE 1

| Plasmid vectors | Characteristics |
| --- | --- |
| pBbA5c-MevT(co)-MBI(co) | Contains p15A, $Cm^R$, PlacUV5 and mevalonate pathway gene |
| pBbA5c-MevT(co)-MBIG(co) | Contains p15A, $Cm^R$, PlacUV5, mevalonate pathway gene and tGPPS gene |
| pBbA5c-MevT(co)-T1-MBI(co) | Contains p15A, $Cm^R$, PlacUV5, Ptrc and mevalonate pathway gene |
| pBbA5c-MevT(co)-T1-MBIG(co) | Contains p15A, $Cm^R$, PlacUV5, Ptrc, mevalonate pathway gene and tGPPS gene |
| pBbE1a-tMS(co.Qi) | Contains ColE1, $Amp^R$, Ptrc and myrcene synthase (MS) from *Q. ilex* L. |
| pBbE1a-tGPPS2(co)-tMS(co.Qi) | Contains ColE1, $Amp^R$, Ptrc, GPPS2 gene from *A. grandis* and myrcene synthase (MS) from *Q. ilex* L. |

In Table 1, $Cm^R$ denotes a chloramphenicol resistance gene and $Amp^R$ denotes an ampicillin resistance gene.

Also, the first vector and the second vector may be *Escherichia coli* expression vectors.

The transformed *Escherichia coli* strain according to an aspect of the present disclosure may be *Escherichia coli* DH1 transformed with the first vector and the second vector. Specifically, it may contain two vectors, i.e., the first vector containing a gene which encodes an enzyme capable of producing dimethylallyl pyrophosphate (DMAPP) or geranyl pyrophosphate (GPP) from a carbon source and the second vector containing a gene which encodes an enzyme capable of producing myrcene from dimethylallyl pyrophosphate (DMAPP) and isopentenyl diphosphate (IPP) or from geranyl pyrophosphate (GPP).

In the present disclosure, the 'first' vector and the 'second' vector do not mean that the parent strain should be transformed with the vectors in that order.

In this aspect, the strain may be one described in Table 2.

TABLE 2

| Strains | Characteristics (introduced plasmid vectors) |
| --- | --- |
| Ec-pM1/pGM(Qi) | DH1, pBbA5c-MevT(co)-MBI(co) and pBbE1a-tGPPS2(co)-tMS(co.Qi) |
| Ec-pM2/pM(Qi) | DH1, pBbA5c-MevT(co)-MBIG(co) and pBbE1a-tMS(co.Qi) |
| Ec-pM2/pGM(Qi) | DH1, pBbA5c-MevT(co)-MBIG(co) and pBbE1a-tGPPS2(co)-tMS(co.Qi) |
| Ec-pM3/pGM(Qi) | DH1, pBbA5c-MevT(co)-T1-MBI(co) and pBbE1a-tGPPS2(co)-tMS(co.Qi) |
| Ec-pM4/pM(Qi) | DH1, pBbA5c-MevT(co)-T1-MBIG(co) and pBbE1a-tMS(co.Qi) |
| Ec-pM4/pGM(Qi) | DH1, pBbA5c-MevT(co)-T1-MBIG(co) and pBbE1a-tGPPS2(co)-tMS(co.Qi) |

The transformed *Escherichia coli* strain according to an aspect of the present disclosure may produce 45 mg/L or more of myrcene in 70 hours under a condition of 37° C. and 1% (w/v) glycerol. It may produce 5 mg/L or more, 10 mg/L or more, 15 mg/L or more, 20 mg/L or more, 25 mg/L or more, 30 mg/L or more, 35 mg/L or more, 40 mg/L or more, 45 mg/L or more, 50 mg/L or more, 55 mg/L or more, 60 mg/L or more, 65 mg/L or more or 70 mg/L or more of myrcene, although not being limited thereto.

The transformed *Escherichia coli* strain according to an aspect of the present disclosure may use glucose or glycerol as a carbon source, although not being limited thereto.

In this aspect, when glycerol is used as a carbon source, the strain may produce 3 times or more, 1.5 times or more, 1.7 times or more, 1.9 times or more, 2 times or more, 2.1 times or more, 2.3 times or more, 2.5 times or more, 2.7 times or more, 2.9 times or more or 3.1 times or more of myrcene as compared to when glucose is used as a carbon source, although not being limited thereto. In this aspect, the amount of myrcene produced may vary depending on the components of a medium in which the *Escherichia coli* strain is cultured.

Also, the *Escherichia coli* strain may be a strain of an accession number KCTC12850BP or KCTC12851BP.

In another aspect, the present disclosure relates to a method for producing myrcene, including a step of culturing a transformed *Escherichia coli* strain.

In this aspect, the method for producing myrcene may further include a step of supplying a carbon source to the culture medium. The carbon source may be glucose or glycerol, although not being limited thereto.

Also, the method for producing myrcene according to an aspect of the present disclosure may further include a step of adding 10-30% (w/v) of dodecane based on the volume of the culture medium. The addition amount of dodecane may be 5-35%, 10-30%, 10-25%, 10-20%, 10-15%, 15-30%, 15-25% or 15-20%, although not being limited thereto. The dodecane may be added simultaneously with the culture medium or the carbon source, or may be added after the culture medium and/or the carbon source has been supplied. The dodecane may be located naturally above the culture medium without being mixed with the culture medium. Specifically, it may be added on top of the culture medium. When the dodecane is added, evaporation and loss of the strongly volatile myrcene into the atmosphere may be prevented.

In another aspect, the present disclosure relates to a method for recycling glycerol, including a step of culturing the *Escherichia coli* strain. In this aspect, the method may further include a step of supplying glycerol, specifically waste glycerol, to the *Escherichia coli* strain. The waste glycerol may be a byproduct from biodiesel production.

Hereinafter, the present disclosure will be described in detail through examples. However, the following examples are for illustrative purposes only and it will be apparent to those of ordinary skill in the art that the scope of the present disclosure is not limited by the examples.

Example 1 Establishment of Strategy for Producing Myrcene

A myrcene metabolic pathway as shown in FIG. 1 was designed to prepare an *Escherichia coli* strain having superior capability of producing myrcene.

Also, literature search was conducted to select a gene encoding a myrcene synthase (MS) gene. Candidate genes were selected based on the literature search and synthesized after codon optimization for expression in *Escherichia coli*. The selected gene was myrcene synthase derived from pine tree (*Quercur liex* L.) (Fischbach R et al., *Eur. J. Biochem.*, 2001).

Example 2 Preparation of Plasmid Vector and Strain

Two types of plasmids were constructed for production of myrcene. To a first plasmid, a gene necessary for producing IPP and DMAPP from acetyl-CoA was introduced. The first plasmid was cloned using a pBbA5c-RFP vector (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12). pBbA5c-RFP was treated with restriction enzymes EcoRI and BamHI and pBbA5c and RFP fragments were isolated by agarose gel electrophoresis. Only the purified pBbA5c vector was used for cloning. A DMAPP producing gene synthesized in the same manner was treated with the same restriction enzymes and then purified. The restriction enzyme-treated pBbA5c vector and DMAPP producing gene were transformed into *E. coli* by treating with ligase and then cloning was conducted. All the genes introduced into the plasmids were prepared by GenScriptR. Additionally, a strong pTrc promoter was introduced upstream of a mevalonate kinase (MK) gene. A total of four plasmids pM1, pM2, pM3 and pM4 were constructed.

Figure 3:
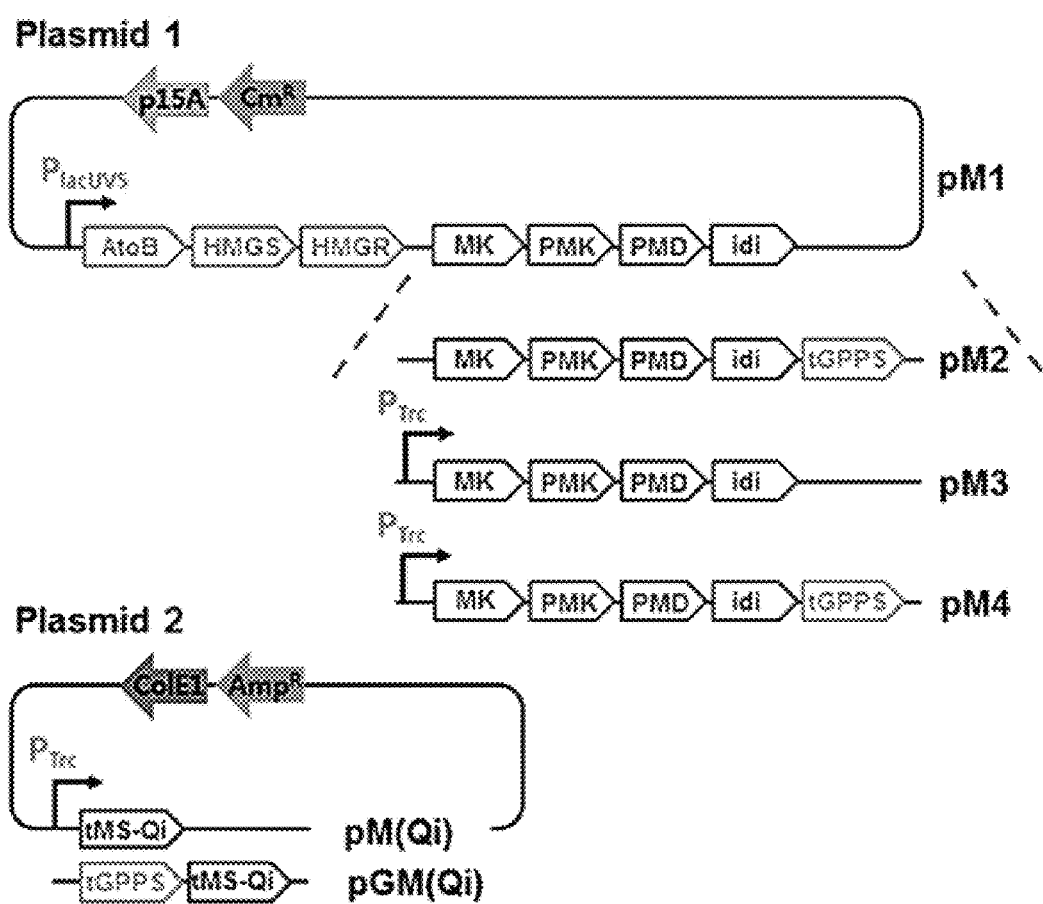
FIG. 3 shows the structure of a first plasmid vector (plasmid 1) and a second plasmid vector (plasmid 2) of the present disclosure.

A second plasmid was prepared as two types, one in which a myrcene synthase gene and a GPP synthase gene were introduced and the other in which only a myrcene synthase gene was introduced (Table 1). The second plasmid was cloned using a pBbE1a-RFP vector (Lee T S, Krupa R A, Zhang F, Hajimorad M, Holtz W J, Prasad N, Lee S K, Keasling J D (2011 b) BglBrick vectors and datasheets: a synthetic biology platform for gene expression. *J Biol Eng* 5:12). The second plasmid was constructed in the same manner as the first plasmid. The constructed plasmids are shown in Table 2 and FIG. 3.

The constructed first plasmid and second plasmid were introduced into an *Escherichia coli* DH1 strain through transformation. The parent strain *Escherichia coli* DH1 was acquired from the *Coli* Genetic Stock Center (CGSC). A total of six myrcene-producing strains were prepared (Table 2).

Example 3 Production of Myrcene Using Transformed *Escherichia coli* Strain

Figure 5A:
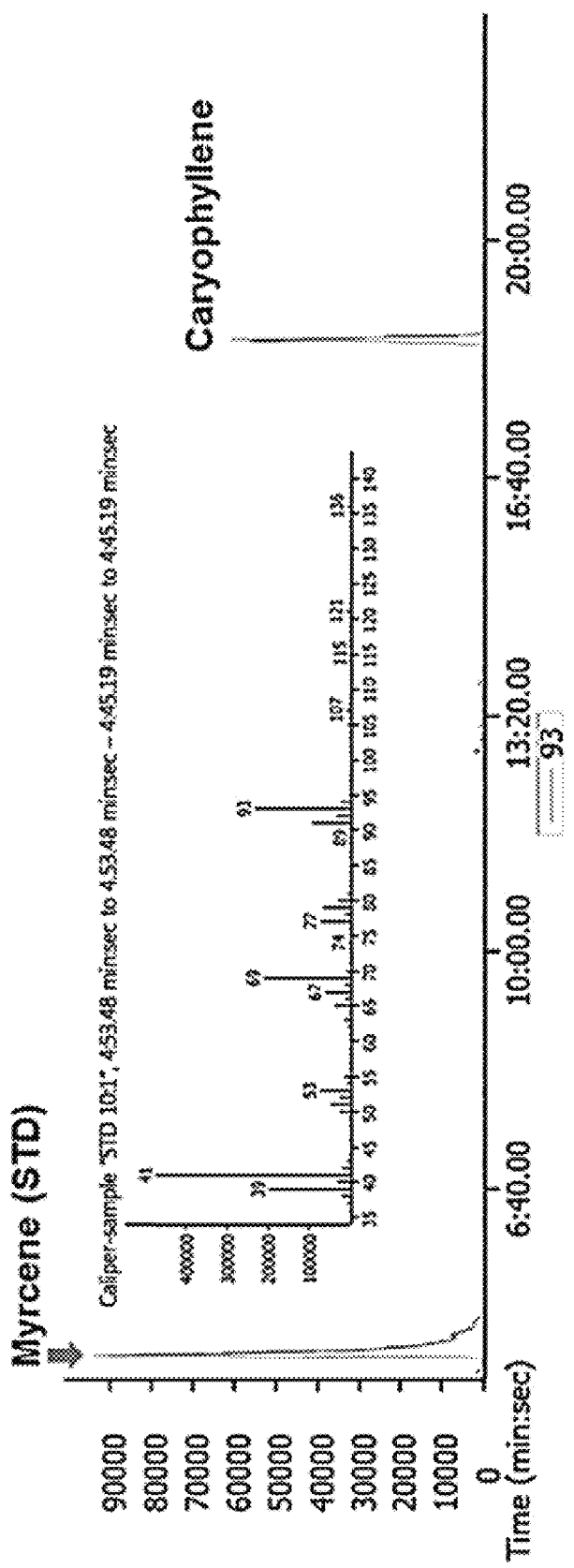
FIG. 5A and FIG. 5B show a result of measuring myrcene production by a transformed *Escherichia coli* strain of the present disclosure by gas chromatography-mass spectrophotometry (A: standard myrcene, B: myrcene produced by transformed *Escherichia coli*).
Figure 5B:
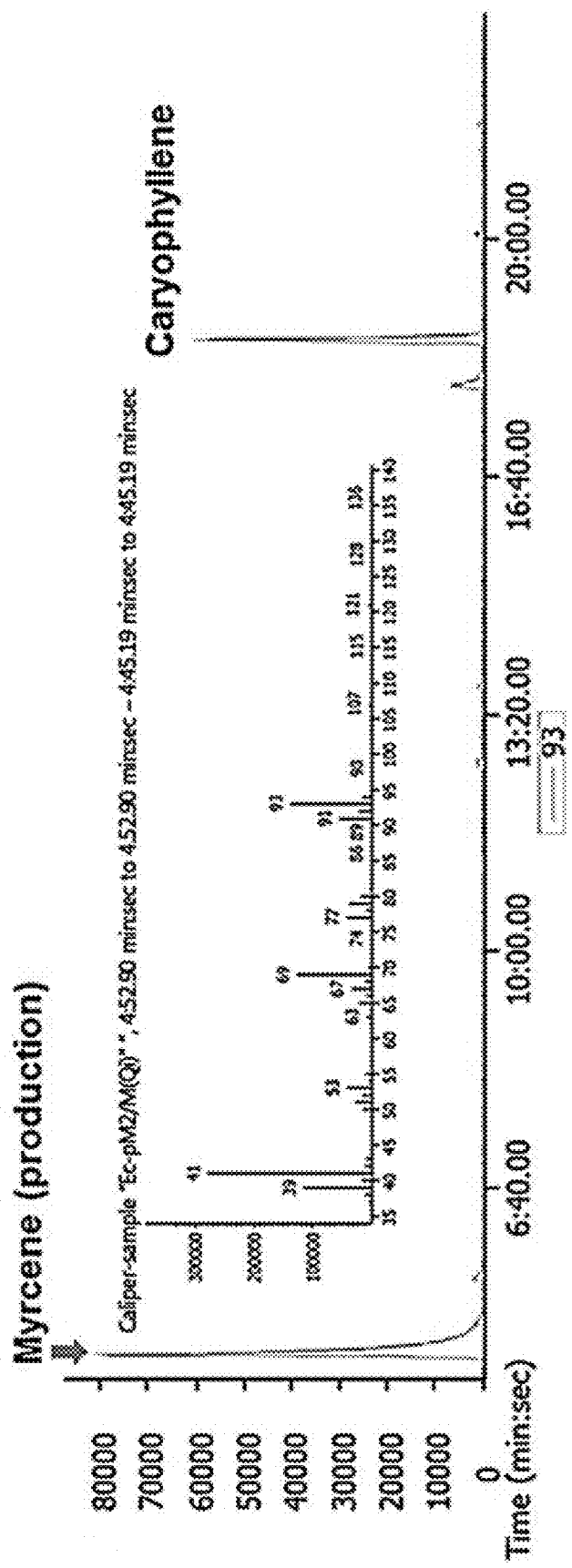
Figure 6A:
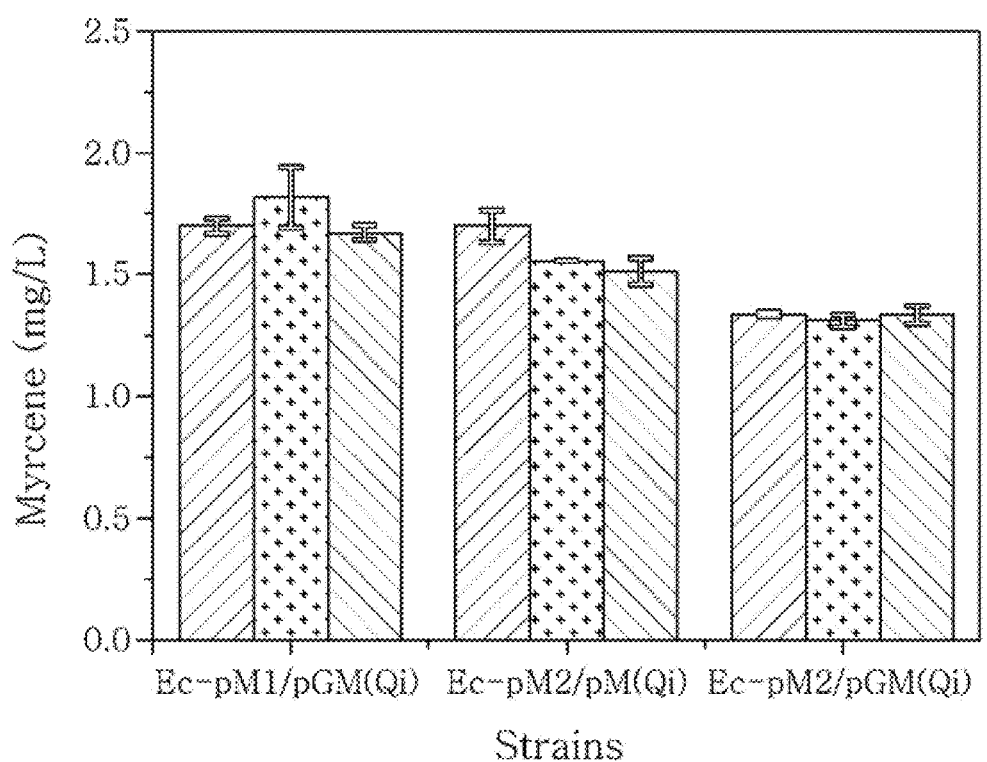
FIG. 6A, FIG. 6B and FIG. 6C show a result of measuring myrcene production by transformed *Escherichia coli* strains of the present disclosure when incubated in a medium supplemented with 1% glucose (first bar: 24 hours later, second bar: 48 hours later, third bar: 72 hours later, A: LB medium, B: EZ-rich medium, C: M9-MOPS medium).
Figure 6B:
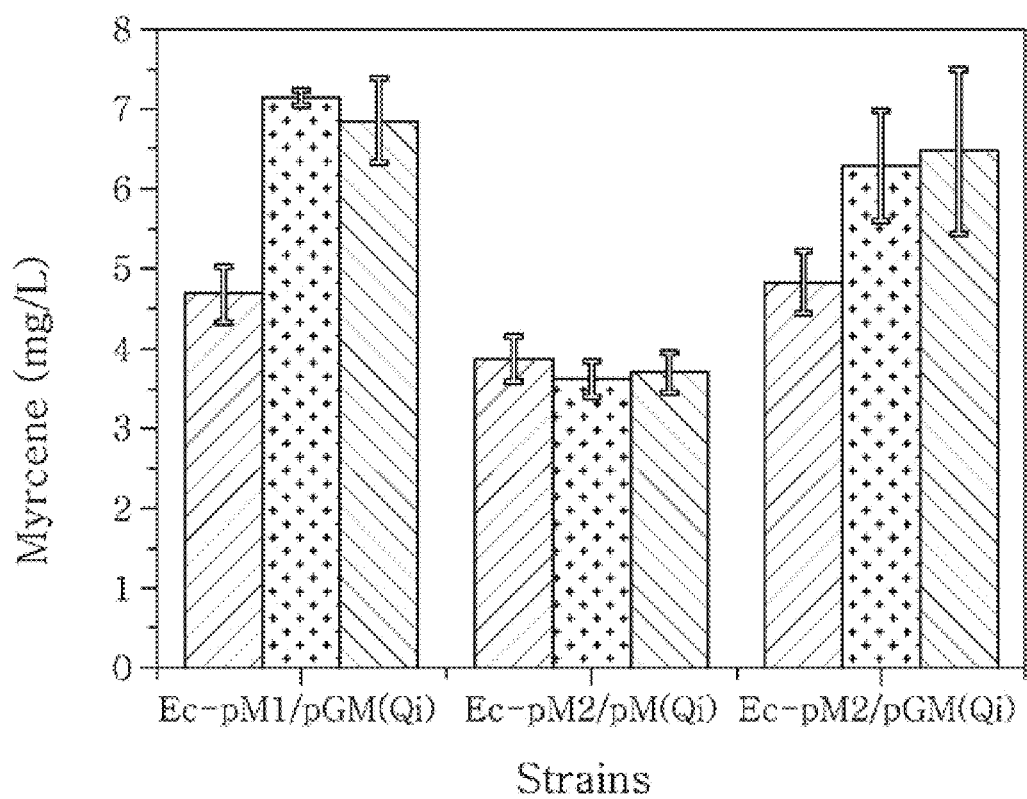
Figure 6C:
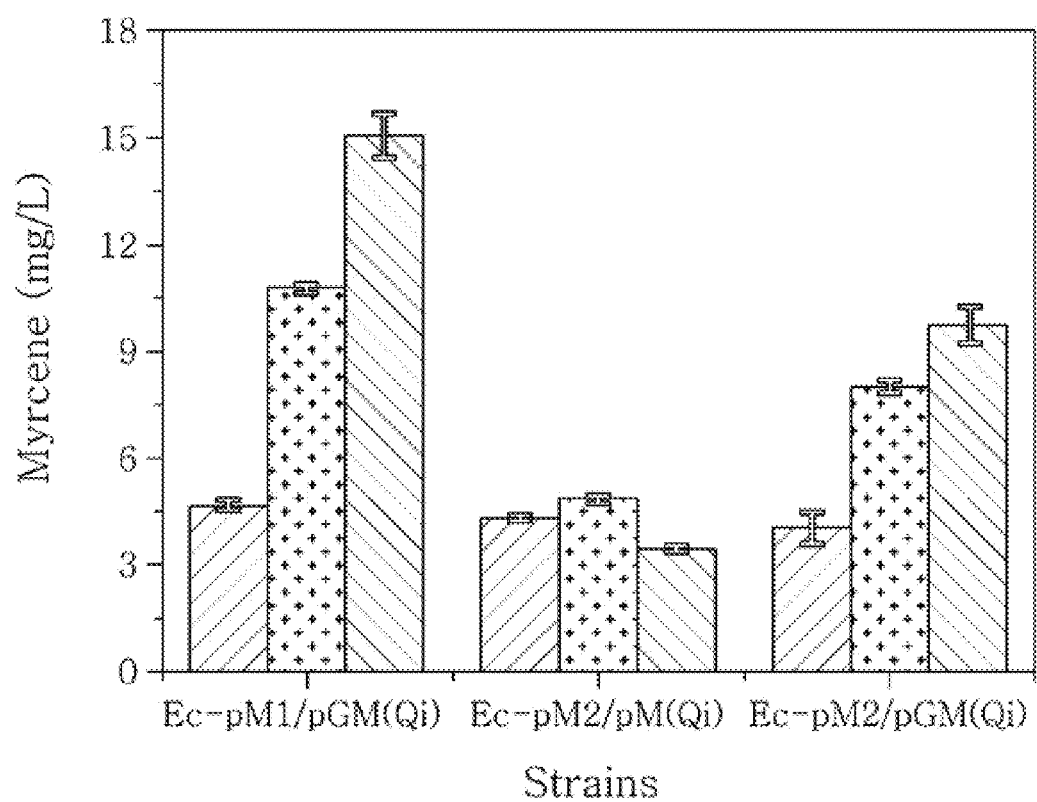

The transformed *Escherichia coli* strain was pre-cultured in a Luria-Bertani (LB) medium for 24 hours and then cultured again in three media: 1. LB, 2. EZ-rich (Teknova, Hollister, Calif.), 3. M9-Mops (M9 salt, 75 mM MOPS, 2 mM $MgSO_4$, 0.01 mM $CaCl_2$, 1 mg/L thiamine HCl, 2.78 mg/L $FeSO_4$, micronutrients: 3 nM ammonium molybdate, 0.4 M boric acid, 30 nM cobalt chloride, 23 nM cupric sulfate, 80 nM manganese chloride, 10 nM zinc sulfate). 1% glucose or 1% glycerol was supplied as a carbon source. After inoculating the strain to the three media and incubating for 4 hours in a shaking incubator at 37° C. at 200 rpm, enzymatic expression was induced by adding 100 μM IPTG (isopropyl β-D-1-thiogalactopyranoside) within an $OD_{600}$ value range of 0.8-1. Then, myrcene was produced by covering the culture medium with 20% (w/v) of dodecane based on the volume of the culture medium. Myrcene production was measured 24 hours, 48 hours and 72 hours later. The amount of myrcene produced for each medium was measured for the cases when 1% glucose was used as a carbon source (FIG. 5) and when 1% glycerol was used (FIG. 6).

Figure 4:
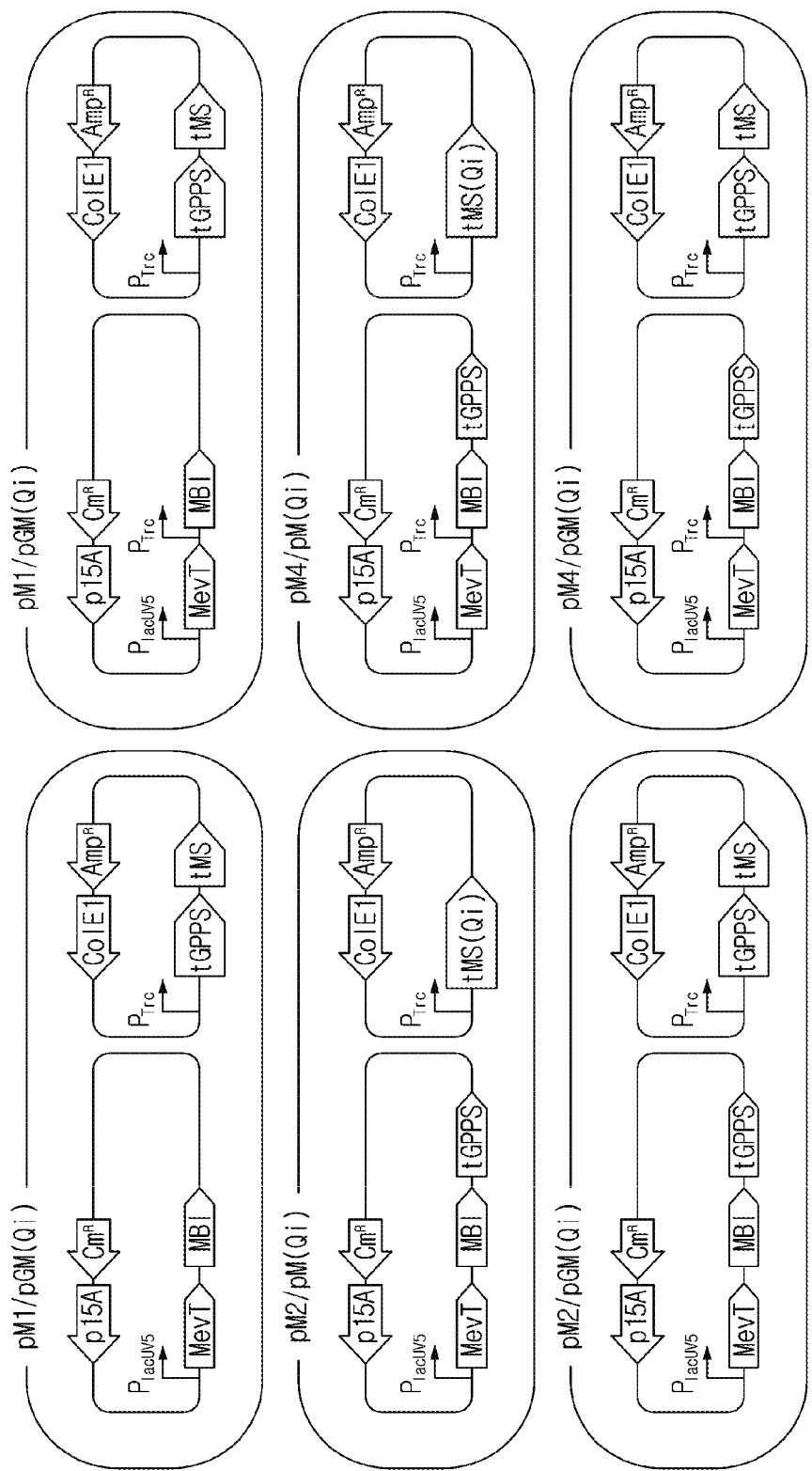
FIG. 4 shows six transformed strains of the present disclosure.

For quantitative analysis of the produced myrcene, comparative analysis was conducted with respect to standard myrcene by gas chromatography-mass spectrometry (GC-MS, Agilent 6890N series GC/TOF-MS (LECO)) (FIG. 4): injector temperature: 250° C., flow rate: 1.2 mL/min, split ratio=2:1, oven temperature: 60° C. for initial 5 minutes, raised at 4° C./min (to 240° C.), He gas used, HP-Ultra2 column: 25 m, 0.2 mm diameter, film thickness: 0.11 μm. All the reagents used in the experiment were acquired from Sigma-Aldrich.

Example 4 Confirmation of Dodecane Overlay Effect

Figure 7A:
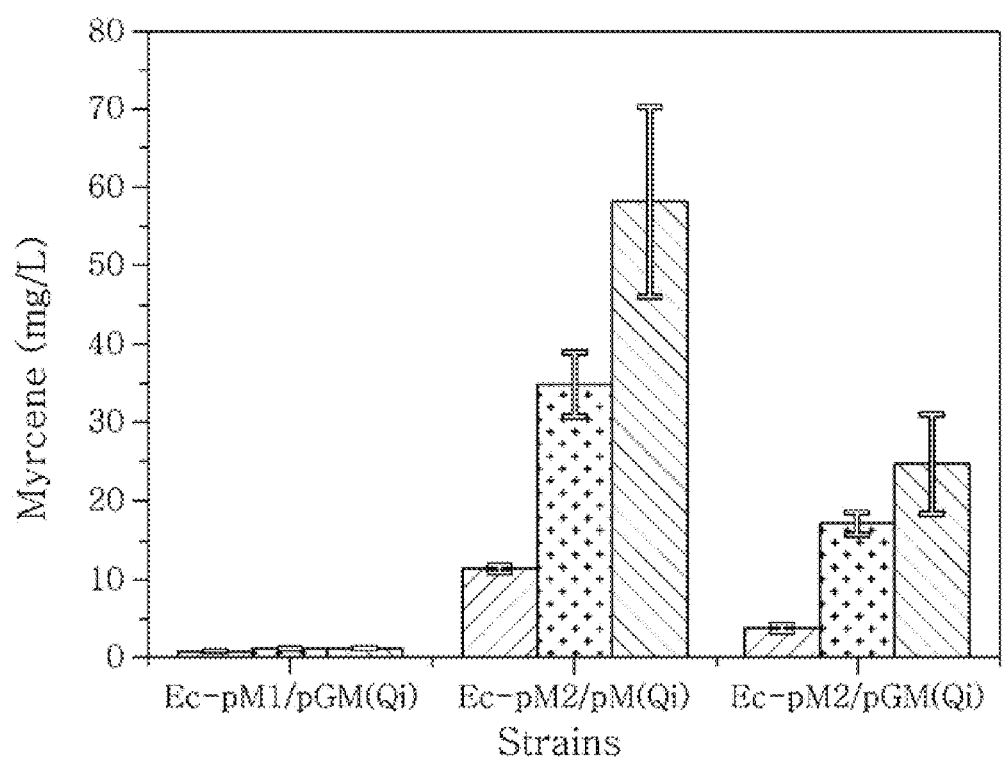
FIG. 7A and FIG. 7B show a result of measuring myrcene production by transformed *Escherichia coli* strains of the present disclosure when incubated in a medium supplemented with 1% glycerol (first bar: 24 hours later, second bar: 48 hours later, third bar: 72 hours later, A: EZ-rich medium, B: M9-MOPS medium).
Figure 7B:
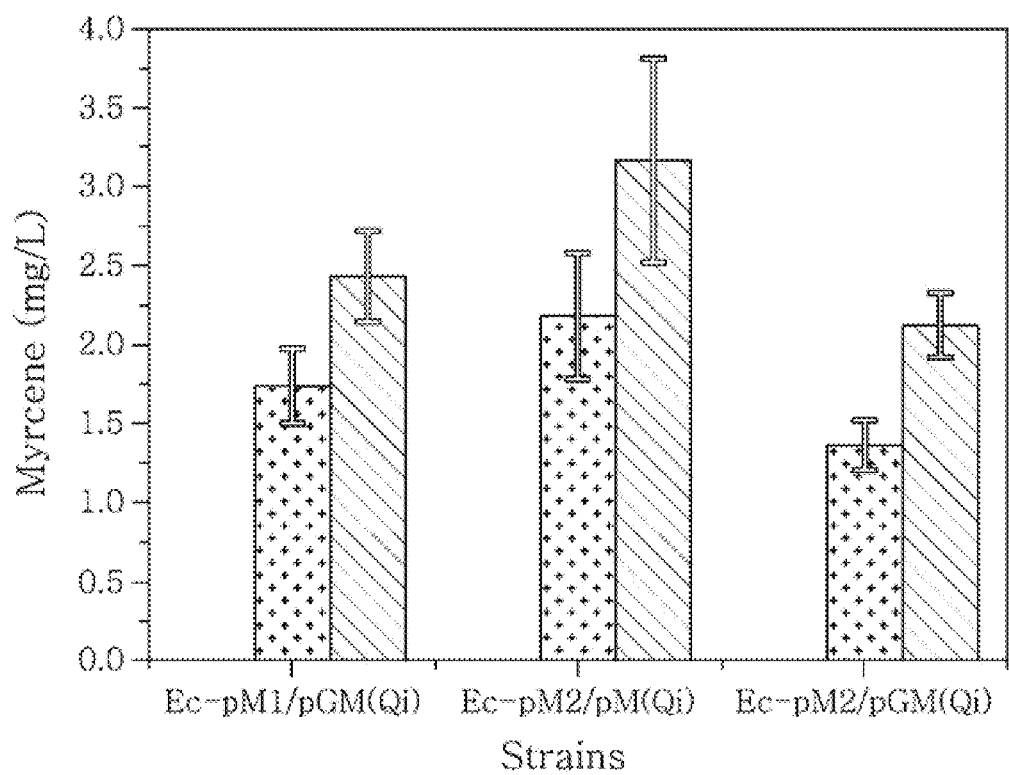
Figure 8:
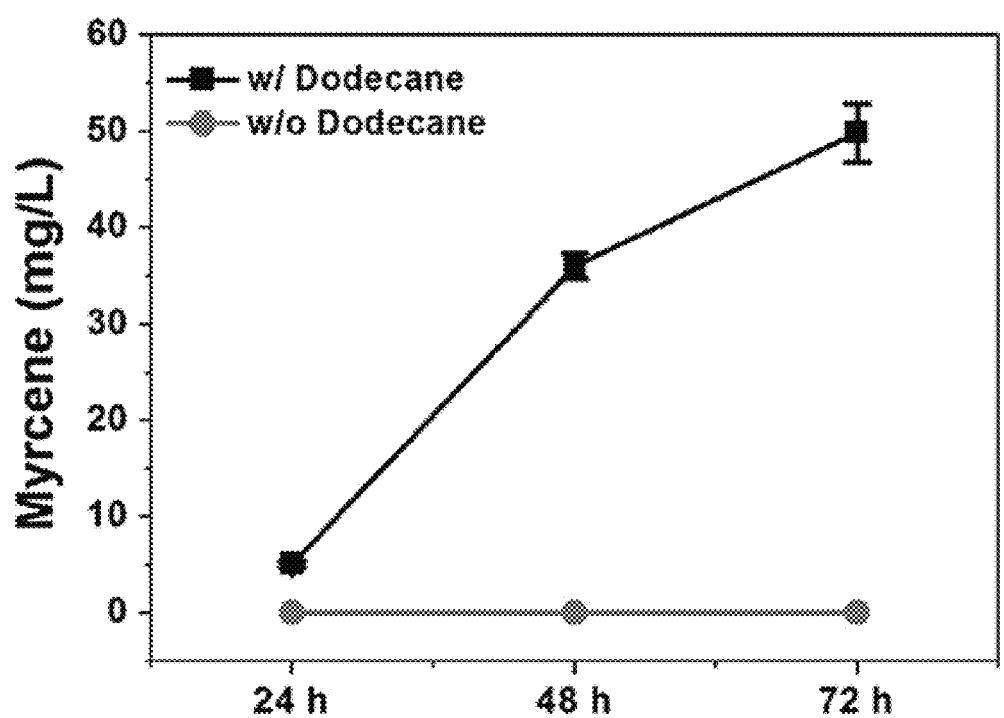
FIG. 8 shows recovery of myrcene with (w) or without (w/o) dodecane overlay.

The dodecane overlay method was used to increase recovery of the strongly volatile myrcene. Because dodecane is separated on top of the medium without being mixed with the medium, the myrcene which is evaporated as soon as it is produced can be extracted from the above dodecane layer. The dodecane overlay effect was compared using the strain (Ec-pM2/pM(Qi)) and condition (1% glycerol, EZ-rich) that showed the highest productivity. As seen from FIG. 7, when dodecane overlay was not used, all the produced myrcene was evaporated and nothing remained.

Biological material was deposited under the terms of the Budapest Treaty, as described below.

Accession Numbers

Depositor: Korea Research Institute of Bioscience & Biotechnology

Accession number: KCTC12850BP

Date of accession: 20150623

Depositor: Korea Research Institute of Bioscience & Biotechnology

Accession number: KCTC12851BP

Date of accession: 20150623

The biological material was accepted by the depository, all restrictions on the availability to the public of the deposited material will be removed, and the viability of the deposits will be maintained for the duration of the patent term or for a period of twenty years in accordance with 37 CFR 1.805-1.807.

What is claimed is:

1. A transformed *Escherichia coli* strain transformed with a first vector and a second vector, the first vector comprising, in sequence:
   a chloramphenicol resistance gene as a selection marker;
   a p15A replication origin;
   a lacUV5 promoter;
   a first domain comprising a series of genes encoding a series of enzymes that contribute to the production of mevalonate from acetyl-CoA; and
   a second domain comprising a series of genes encoding a series of enzymes that contribute to the production of dimethylallyl pyrophosphate (DMAPP) from mevalonate; and
   the second vector comprising, in sequence:
   an ampicillin resistance gene as a selection marker;
   a ColE1 replication origin;
   a trc promoter; and
   a gene encoding an enzyme capable of producing myrcene from geranyl pyrophosphate (GPP).

2. The transformed *Escherichia coli* strain according to claim 1,
   wherein the first domain of the first vector comprises, in sequence:
   a gene encoding acetyl-CoA thiolase (ACAT);
   a gene encoding 3-hydroxyl-3-methyl-glutaryl-CoA synthase (HMGS); and
   a gene encoding 3-hydroxyl-3-methyl-glutaryl-CoA reductase (HMGR), and
   wherein the second domain comprises, in sequence,
   a gene encoding mevalonate kinase (MK);
   a gene encoding phosphomevalonate kinase (PMK);
   a gene encoding mevalonate diphosphate decarboxylase (PMD); and
   a gene encoding isopentenyl diphosphate isomerase (IDI).

3. The transformed *Escherichia coli* strain according to claim 2,
   wherein the gene encoding acetyl-CoA thiolase (ACAT) comprises a sequence of SEQ ID NO: 1,
   the gene encoding 3-hydroxyl-3-methyl-glutaryl-CoA synthase (HMGS) comprises a sequence of SEQ ID NO: 2,
   the gene encoding 3-hydroxyl-3-methyl-glutaryl-CoA reductase (HMGR) comprises a sequence of SEQ ID NO: 3,
   the gene encoding mevalonate kinase (MK) comprises a sequence of SEQ ID NO: 4,
   the gene encoding phosphomevalonate kinase (PMK) comprises a sequence of SEQ ID NO: 5,
   the gene encoding mevalonate diphosphate decarboxylase (PMD) comprises a sequence of SEQ ID NO: 6, and
   the gene encoding isopentenyl diphosphate isomerase (IDI) comprises a sequence of SEQ ID NO: 7.

4. The transformed *Escherichia coli* strain according to claim 1, wherein the enzyme capable of producing myrcene from geranyl pyrophosphate (GPP) is myrcene synthase (MS).

5. The transformed *Escherichia coli* strain according to claim 4, wherein the gene encoding myrcene synthase (MS) comprises a sequence of SEQ ID NO: 9.

6. The transformed *Escherichia coli* strain according to claim 1,
   wherein the first vector further comprises one or more selected from the group consisting of: a trc promoter, and a gene encoding an enzyme capable of producing geranyl pyrophosphate (GPP) from dimethylallyl pyrophosphate (DMAPP) and isopentenyl diphosphate (IPP),
   wherein the trc promoter is located between the first domain and the second domain, and
   wherein the gene encoding the enzyme capable of producing geranyl pyrophosphate (GPP) from dimethylallyl pyrophosphate (DMAPP) and isopentenyl diphosphate (IPP) is located downstream of the second domain.

7. The transformed *Escherichia coli* strain according to claim 6, wherein the enzyme capable of producing geranyl pyrophosphate (GPP) from dimethylallyl pyrophosphate (DMAPP) and isopentenyl diphosphate (IPP) is geranyl pyrophosphate synthase (GPPS).

8. The transformed *Escherichia coli* strain according to claim 7, wherein the gene encoding geranyl pyrophosphate synthase (GPPS) comprises a sequence of SEQ ID NO: 8.

9. The transformed *Escherichia coli* strain according to claim 1, wherein the second vector further comprises, between the trc promoter and the gene encoding the enzyme capable of producing myrcene from geranyl pyrophosphate (GPP), a gene encoding an enzyme capable of producing geranyl pyrophosphate (GPP) from dimethylallyl pyrophosphate (DMAPP) and isopentenyl diphosphate (IPP).

10. The transformed *Escherichia coli* strain according to claim 9, wherein the enzyme capable of producing geranyl pyrophosphate (GPP) from dimethylallyl pyrophosphate (DMAPP) and isopentenyl diphosphate (IPP) is geranyl pyrophosphate synthase (GPPS).

11. The transformed *Escherichia coli* strain according to claim 10, wherein the gene encoding geranyl pyrophosphate synthase (GPPS) comprises a sequence of SEQ ID NO: 8.

12. The transformed *Escherichia coli* strain according to claim 1, wherein the first vector comprises a sequence of any of SEQ ID NO: 10, SEQ ID NO: 11, SEQ ID NO: 12, or SEQ ID NO: 13.

13. The transformed *Escherichia coli* strain according to claim 1, wherein the second vector further comprises a sequence of SEQ ID NO: 14 or SEQ ID NO: 15.

14. The transformed *Escherichia coli* strain according to claim 1, wherein the *Escherichia coli* strain is *Escherichia coli* DH1 transformed with the first vector and the second vector.

15. The transformed *Escherichia coli* strain according to claim 14, wherein the *Escherichia coli* strain produces at least 45 mg/L of myrcene in 70 hours under a condition of 37° C. and 1% (w/v) glycerol.

16. The transformed *Escherichia coli* strain according to claim 14, wherein, the *Escherichia coli* strain produces at least 3 times an amount of myrcene when glycerol is used as a carbon source as compared to when glucose is used as a carbon source.

17. The transformed *Escherichia coli* strain according to claim 14, wherein the *Escherichia coli* strain is an *Escherichia coli* strain of accession number KCTC12850BP or KCTC12851BP.

* * * * *

SEQUENCE LISTING

<160> NUMBER OF SEQ ID NOS: 15

<210> SEQ ID NO 1
<211> LENGTH: 1185
<212> TYPE: DNA
<213> ORGANISM: Artificial Sequence
<220> FEATURE:
<223> OTHER INFORMATION: atoB gene

<400> SEQUENCE: 1

| | | | | | |
|---|---|---|---|---|---|
| atgaagaact | gtgtgattgt | ttctgcggtc | cgcacggcga | tcggcagctt | taacggctct | 60 |
| ttagcgagca | cctctgcaat | cgatctgggt | gcgacggtca | ttaaggccgc | cattgaacgc | 120 |
| gccaaaatcg | acagccagca | cgttgatgag | gtgatcatgg | caatgtgtt | acaagccggc | 180 |
| ctgggtcaaa | acccagcgcg | tcaagcactg | ttaaaatctg | gtctggccga | daccgtgtgt | 240 |
| ggcttcaccg | tcaataaggt | ttgcggctct | ggcctgaaga | gcgtggccct | ggcagcacaa | 300 |
| gcgattcaag | ccggtcaggc | acaaagcatc | gttgcgggtg | gcatggagaa | catgtctctg | 360 |
| gcgccgtact | tattagatgc | caaagcccgc | agcggttatc | gcctgggcga | tggtcaggtg | 420 |
| tacgacgtca | tcttacgcga | tggcttaatg | tgcgcgaccc | acggttacca | catgggtatt | 480 |
| acggccgaaa | acgtggcgaa | agaatacggc | attacgcgcg | agatgcagga | tgaattagca | 540 |
| ctgcactctc | agcgcaaagc | agcagccgcg | atcgagtctg | gtgcgtttac | ggcggaaatc | 600 |
| gtgccagtta | acgtggtcac | gcgcaagaag | acgttcgttt | tcagccagga | cgagttcccg | 660 |
| aaggcaaaca | gcaccgcgga | ggccttaggt | gccttacgcc | cagcctttga | caaagcgggc | 720 |
| acggtcaccg | ccggtaatgc | gagcggcatc | aatgatggtg | cagcggcact | ggtcatcatg | 780 |
| gaagagagcg | ccgcattagc | agcgggtctg | accccattag | cgcgcattaa | atcttatgcc | 840 |
| agcggcggcg | tcccaccagc | cctgatgggc | atgggtccgg | tcccagccac | gcaaaaagcc | 900 |
| ctgcaattag | cgggcctgca | actggccgac | attgatctga | tcgaggcgaa | cgaggcgttt | 960 |
| gcagcgcagt | tcctggcggt | gggtaagaat | ctgggcttcg | acagcgagaa | agtcaatgtg | 1020 |
| aacggtggcg | cgattgcgtt | aggccatccg | attggtgcaa | gcggcgcacg | catcttagtg | 1080 |
| acgttactgc | acgccatgca | ggcacgcgac | aagacccttag | gcctggcgac | cttatgtatt | 1140 |
| ggtggcggtc | aaggtatcgc | catggtgatc | gaacgcctga | actga | | 1185 |

<210> SEQ ID NO 2
<211> LENGTH: 1476
<212> TYPE: DNA
<213> ORGANISM: Artificial Sequence
<220> FEATURE:
<223> OTHER INFORMATION: HMGS gene

<400> SEQUENCE: 2

| | | | | | |
|---|---|---|---|---|---|
| atgaaactga | gcaccaagct | gtgctggtgt | ggcatcaagg | gtcgcctgcg | cccacaaaag | 60 |
| cagcaacagc | tgcacaacac | gaacctgcaa | atgaccgagc | tgaaaaagca | gaagacggcc | 120 |
| gagcaaaaga | cccgcccgca | gaacgttggc | atcaagggca | tccagattta | tatcccgacg | 180 |
| cagtgtgtca | accaatctga | gctggagaaa | ttcgatggcg | tcagccaggg | taagtacacc | 240 |
| atcggcctgg | gccagaccaa | catgagcttc | gtgaacgacc | gtgaggacat | ctattctatg | 300 |
| agcctgacgg | tgctgtctaa | gctgatcaag | agctacaaca | tcgacacgaa | taagatcggt | 360 |
| cgtctggagg | tgggtacgga | gacgctgatt | gacaagagca | aaagcgtgaa | gtctgtctta | 420 |
| atgcagctgt | tcggcgagaa | cacggatgtc | gagggtatcg | acacccctgaa | cgcgtgttac | 480 |
| ggcggcacca | acgcactgtt | caatagcctg | aactggattg | agagcaacgc | ctgggatggc | 540 |

-continued

| | |
|---|---|
| cgcgatgcga tcgtcgtgtg cggcgatatc gccatctatg acaagggtgc ggcacgtccg | 600 |
| accggcggtg caggcaccgt tgcgatgtgg attggcccgg acgcaccaat tgtcttcgat | 660 |
| tctgtccgcg cgtcttacat ggagcacgcc tacgactttt acaagccgga cttcacgagc | 720 |
| gaatacccgt acgtggacgg ccacttctct ctgacctgct atgtgaaggc gctggaccag | 780 |
| gtttataagt cttatagcaa aaaggcgatt tctaagggcc tggtcagcga cccggcaggc | 840 |
| agcgacgccc tgaacgtgct gaagtatttc gactacaacg tgttccatgt cccgacctgc | 900 |
| aaattagtga ccaaatctta tggccgcctg ttatataatg atttccgtgc caacccgcag | 960 |
| ctgttcccgg aggttgacgc cgagctggcg acgcgtgatt acgacgagag cctgaccgac | 1020 |
| aagaacatcg agaagacctt cgtcaacgtc gcgaagccgt tccacaaaga gcgtgtggcc | 1080 |
| caaagcctga tcgtcccgac caacacgggc aacatgtata ccgcgtctgt ctacgcggca | 1140 |
| ttcgcgagcc tgctgaatta cgtcggttct gacgacctgc agggcaagcg cgttggcctg | 1200 |
| ttcagctacg gtagcggctt agcggccagc ctgtatagct gcaaaattgt cggcgacgtc | 1260 |
| cagcacatca tcaaggagct ggacatcacc aacaagctgg cgaagcgcat caccgagacg | 1320 |
| ccgaaagatt acgaggcagc gatcgagtta cgcgagaatg cgcatctgaa gaagaacttc | 1380 |
| aagccgcaag gtagcatcga gcacctgcag agcggcgtct actacctgac gaacattgac | 1440 |
| gacaagttcc gccgttctta tgacgtcaaa aagtaa | 1476 |

<210> SEQ ID NO 3
<211> LENGTH: 1509
<212> TYPE: DNA
<213> ORGANISM: Artificial Sequence
<220> FEATURE:
<223> OTHER INFORMATION: HMGR gene

<400> SEQUENCE: 3

| | |
|---|---|
| atggtgctga cgaacaaaac cgtcattagc ggcagcaagg tgaagtctct gagcagcgcc | 60 |
| caaagctcta gcagcggccc gtctagcagc agcgaggagg acgacagccg tgacattgag | 120 |
| tctctggaca gaagatccg cccgctggag gagttagagg ccctgctgag cagcggcaac | 180 |
| accaagcagc tgaagaacaa ggaagttgca gcgctggtga tccacggtaa gctgccactg | 240 |
| tatgcgctgg aaaagaaact gggcgatacg acgcgtgcgg tcgcggtgcg tcgcaaagcc | 300 |
| ttaagcatct tagcggaggc cccggtgtta gccagcgacc gctgccgta caagaactac | 360 |
| gactacgacc gcgtgtttgg cgcgtgctgc gagaatgtca ttggctacat gccgttaccg | 420 |
| gttggtgtga tcggcccgct ggtcattgat ggcacgagtc atcacattcc aatggcgacc | 480 |
| acggaaggtt gcttagtcgc cagcgccatg cgtggctgta aggcgattaa cgccggcggt | 540 |
| ggcgcgacga ccgtgttaac caaggatggt atgacgcgcg tccggtcgt ccgcttccca | 600 |
| acgctgaagc gcagcggcgc gtgtaagatt tggctggatt ctgaggaggg ccaaaacgcg | 660 |
| atcaagaaag ccttcaactc tacgagccgt ttcgcgcgtt acagcatat ccagacctgc | 720 |
| ctggccggcg acctgctgtt catgcgcttc cgcaccacca cgggcgatgc gatgggcatg | 780 |
| aacatgatca gcaagggcgt cgaatatagc ctgaaacaaa tggtggaaga atatggctgg | 840 |
| gaggacatgg aggttgtctc tgtgagcggc aactattgca ccgacaagaa gccggcagcc | 900 |
| attaactgga ttgagggtcg cggcaaaagc gtcgtggcag aagcgaccat cccaggcgac | 960 |
| gtggtccgta aggttctgaa gagcgacgtc agcgccctgg ttgagttaaa tatcgcgaaa | 1020 |
| aacctggtcg gcagcgcgat ggcgggcagc gtgggtggct ttaacgcaca tgcagcgaat | 1080 |

```
ctggttacgg cggttttctt agccttaggt caggacccag cccaaaatgt cgagagcagc   1140
aactgcatta ccttaatgaa agaggttgac ggtgacctgc gcatcagcgt ttctatgccg   1200
tctatcgagg tcggcacgat cggcggcggc accgttttag aaccgcaagg tgcgatgctg   1260
gatctgctgg gcgtgcgcgg cccacatgca acggccccag gcaccaatgc ccgccaactg   1320
gcccgtatcg tggcctgcgc ggttctggcg ggtgagctga gcctgtgcgc cgcattagcc   1380
gcgggccatt tagttcaatc tcacatgacc cacaaccgca agccggcaga accaaccaag   1440
ccaaataacc tggacgcaac cgacattaac cgtctgaagg atggcagcgt cacgtgcatt   1500
aaaagctga                                                           1509

<210> SEQ ID NO 4
<211> LENGTH: 1332
<212> TYPE: DNA
<213> ORGANISM: Artificial Sequence
<220> FEATURE:
<223> OTHER INFORMATION: MK gene

<400> SEQUENCE: 4
atgtctctgc cattcctgac gtctgcgcca ggtaaggtga tcatcttcgg cgagcactct     60
gcggtgtaca ataagccggc cgtcgccgcc tctgtgtctg cgttacgcac ctacctgctg    120
atcagcgaat cttctgcacc ggacacgatc gagctggact ttccggacat cagcttcaac    180
cacaagtgga gcatcaacga cttcaacgcg atcacggagg accaggtgaa cagccaaaag    240
ctggccaaag cccagcaagc aaccgacggt ctgtctcagg agctggtgtc tctgctggac    300
ccgctgttag cgcagttaag cgagagcttc cattaccacg ccgcgttctg cttcctgtac    360
atgttcgttt gcctgtgccc gcacgcaaag aacatcaagt tcagcctgaa gagcacgctg    420
ccgattggcg caggcttagg ctctagcgca tctatcagcg tgagcctggc gctggcgatg    480
gcctatctgg gtggcctgat tgcagcaaca gacctggaga aactgagcga aaacgacaag    540
cacatcgtga accagtgggc ctttatcggc gagaagtgca ttcatggcac cccgagcggc    600
attgacaacg cagttgccac gtatggcaac gccctgctgt tcgagaaaga cagccacaac    660
ggcacgatca cacgaacaa cttcaagttc tggacgact cccggcgat cccgatgatt      720 ctgacctaca cccgtatccc acgcagcacc aaggatttag tcgcccgcgt gcgtgtttta    780
gtcaccgaaa agttcccgga ggtgatgaag ccgatcctgg acgcgatggg cgagtgcgcg    840
ctgcagggtc tggagatcat gaccaagctg agcaagtgca agggcaccga cgatgaggcg    900
gtggagacca caatgagct gtacgagcag ctgctggagc tgatccgtat caatcacggc    960
ctgctggtct ctatcggtgt gtctcacccg ggcctggaac tgatcaaaaa cctgagcgac   1020
gacctgcgca ttggctctac gaaattaacg ggtgcaggtg gcggtggctg ctctttaacg   1080
ctgctgcgcc gtgacattac gcaggagcaa atcgacagct caagaagaa gctgcaggac   1140 gacttcagct acgagacgtt cgagacggac ctgggcggca cgggctgttg cctgctgagc   1200
gccaaaaatc tgaacaagga cctgaagatc aaaagcctgg tgttccagct gttcgaaaac   1260
aagacgacca cgaagcagca gatcgacgac ctgttactgc cgggtaacac caatctgccg   1320
tggacgtctt aa                                                       1332

<210> SEQ ID NO 5
<211> LENGTH: 1356
<212> TYPE: DNA
<213> ORGANISM: Artificial Sequence
<220> FEATURE:
<223> OTHER INFORMATION: PMK gene
```

<400> SEQUENCE: 5

```
atgagcgaat tacgtgcatt cagcgcgcca ggtaaggcac tgctggccgg tggctacctg      60
gtgttagaca ccaagtacga ggcgttcgtc gtcggcttat ctgcccgtat gcatgcagtt     120
gcccacccgt atggtagcct gcagggctct gacaagttcg aagtgcgtgt gaagagcaag     180
cagttcaagg acggcgagtg gctgtaccac attagcccaa agagcggctt catcccggtt     240
agcattggtg gcagcaagaa cccatttatc gagaaggtca ttgccaacgt cttcagctac     300
ttcaagccga atatggacga ttactgcaac cgcaacctgt tcgtcatcga cattttcagc     360
gacgacgcgt accacagcca agaggactct gttacgagc atcgtggtaa ccgccgcctg      420
agcttccaca gccatcgcat tgaggaggtg ccgaagacgg gtctgggttc tagcgccggt     480
ttagttaccg tcttaacgac ggcgttagcg agcttcttcg tgagcgacct ggagaacaac     540
gtggacaagt accgcgaagt gattcataac ctggcgcagg tggcacattg tcaggcccaa     600
ggtaagattg gctctggttt tgatgtggca gcggccgcct atggctctat ccgctatcgc     660
cgcttccgc cggccctgat cagcaatctg ccggacatcg gctctgcgac gtatggtagc      720
aaactggcgc atctggtgga cgaagaagac tggaacatca ccattaagtc taatcacctg     780
ccgagcggct taacgttatg gatgggcgat atcaagaacg gcagcgaaac ggttaagctg     840
gtgcagaaag tgaaaaactg gtacgacagc acatgccgg aaagcctgaa gatttacacg      900
gagctggacc acgccaatag ccgtttcatg gatggtctga gcaagctgga ccgcctgcac     960
gaaacccacg acgactacag cgaccaaatc ttcgagagcc tggagcgcaa tgactgcacc    1020
tgccagaagt acccggagat cacggaggtc cgcgatgccg tggcaacgat cgccgtagc     1080
ttccgcaaaa ttacgaagga gagcggcgcg gatatcgaac caccggtcca gacgtctctg    1140
ctggacgact gtcaaacctt aaagggcgtg ttaacgtgcc tgattccggg cgcgggtggt    1200
tacgacgcca ttgccgtcat cacgaaacag gacgtcgatc tgcgcgcaca aacggccaac    1260
gacaaacgtt tcagcaaagt ccaatggctg gatgttacgc aggccgactg gggtgttcgc    1320
aaggagaagg acccggaaac gtatctggat aagtga                             1356
```

<210> SEQ ID NO 6
<211> LENGTH: 1191
<212> TYPE: DNA
<213> ORGANISM: Artificial Sequence
<220> FEATURE:
<223> OTHER INFORMATION: PMD gene

<400> SEQUENCE: 6

```
atgaccgttt acacagcatc cgttaccgca cccgtcaaca tcgcaaccct taagtattgg      60
gggaaaaggg acacgaagtt gaatctgccc accaattcgt ccatatcagt gactttatcg     120
caagatgacc tcagaacgtt gacctctgcg gctactgcac ctgagtttga acgcgacact     180
ttgtggttaa atggagaacc acacagcatc gacaatgaaa gaactcaaaa ttgtctgcgc     240
gacctacgcc aattaagaaa ggaaatggaa tcgaaggacg cctcattgcc cacattatct     300
caatggaaac tccacattgt ctccgaaaat aactttccta cagcagctgg tttagcttcc     360
tccgctgctg gctttgctgc attggtctct gcaattgcta agttatacca attaccacag     420
tcaacttcag aaatatctag aatagcaaga aaggggtctg gttcagcttg tagatcgttg     480
tttggcggat acgtggcctg ggaaatggga aaagctgaag atggtcatga ttccatggca     540
gtacaaatcg cagacagctc tgactggcct cagatgaaag cttgtgtcct agttgtcagc    600
```

```
gatattaaaa aggatgtgag ttccactcag ggtatgcaat tgaccgtggc aacctccgaa      660
ctatttaaag aaagaattga acatgtcgta ccaaagagat ttgaagtcat gcgtaaagcc      720
attgttgaaa aagatttcgc cacctttgca aaggaaacaa tgatggattc caactctttc     780
catgccacat gtttggactc tttccctcca atattctaca tgaatgacac ttccaagcgt     840
atcatcagtt ggtgccacac cattaatcag ttttacggag aaacaatcgt tgcatacacg     900
tttgatgcag gtccaaatgc tgtgttgtac tacttagctg aaaatgagtc gaaactcttt     960
gcatttatct ataaattgtt tggctctgtt cctggatggg acaagaaatt tactactgag    1020
cagcttgagg ctttcaacca tcaatttgaa tcatctaact ttactgcacg tgaattggat    1080
cttgagttgc aaaaggatgt tgccagagtg attttaactc aagtcggttc aggcccacaa    1140
gaaacaaacg aatctttgat tgacgcaaag actggtctac caaaggaata a             1191

<210> SEQ ID NO 7
<211> LENGTH: 549
<212> TYPE: DNA
<213> ORGANISM: Artificial Sequence
<220> FEATURE:
<223> OTHER INFORMATION: IDI gene

<400> SEQUENCE: 7
atgcaaacgg aacacgtcat tttattgaat gcacagggag ttcccacggg tacgctggaa      60
aagtatgccg cacacacggc agacacccgc ttacatctcg cgttctccag ttggctgttt     120
aatgccaaag acaattatt agttacccgc cgcgcactga gcaaaaaagc atggcctggc      180
gtgtggacta actcggtttg tgggcaccca caactgggaa aaagcaacga agacgcagtg     240
atccgccgtt gccgttatga gcttggcgtg gaaattacgc ctcctgaatc tatctatcct     300
gactttcgct accgcgccac cgatccgagt ggcattgtgg aaaatgaagt gtgtccggta     360
tttgccgcac gcaccactag tgcgttacag atcaatgatg atgaagtgat ggattatcaa     420
tggtgtgatt tagcagatgt attacacggt attgatgcca cgccgtgggc gttcagtccg     480
tggatggtga tgcaggcgac aaatcgcgaa gccagaaaac gattatctgc atttacccag     540
cttaaataa                                                            549

<210> SEQ ID NO 8
<211> LENGTH: 897
<212> TYPE: DNA
<213> ORGANISM: Artificial Sequence
<220> FEATURE:
<223> OTHER INFORMATION: tGPPS gene

<400> SEQUENCE: 8
atggtggaat ttgatttta caaatatatg gatagcaaag cgatgaccgt gaacgaagcg        60
ctgaacaaag cgattccgct gcgctatccg cagaaaattt atgaaagcat gcgctatagc     120
ctgctggcgg gcgcaaaacg cgtgcgcccc gtgctgtgca ttgcggcgtg cgaactggtg     180
ggcggcaccg aagaactggc gattccgacc gcgtgcgcga ttgaaatgat tcataccatg     240
agcctgatgc atgatgatct gccgtgcatt gataacgatg atctgcgccg cggcaaaccg     300
accaaccata aaattttgg cgaagatacc gcggtgaccg cggcaacgc gctgcatagc      360 tatgcgtttg aacatattgc ggtgagcacc agcaaaaccg tgggcgcgga tcgcattctg     420
cgcatggtga cgaactggg ccgcgcgacc ggcagcgaag cgtgatggg cggccagatg      480 gtggatattg cgagcgaagg cgatccgagc attgatctgc agaccctgga atggattcat     540
attcataaaa ccgcgatgct gctggaatgc agcgtggtgt gcggcgcgat tattggcggc    600
```

```
gcgagcgaaa ttgtgattga acgcgcgcgc cgctatgcgc gctgcgtggg cctgctgttt      660
caggtggtgg atgatattct ggatgtgacc aaaagcagcg atgaactggg caaaaccgcg      720
ggcaaagatt taattagcga taaagcgacc tatccgaaac tgatgggcct ggaaaaagcg      780
aaagaattta gcgatgaact gctgaaccgc gcgaaaggcg aactgagctg ctttgatccg      840
gtgaaagcgg cgccgctgct gggcctggcg gattatgtgg cgtttcgcca gaactaa        897

<210> SEQ ID NO 9
<211> LENGTH: 1629
<212> TYPE: DNA
<213> ORGANISM: Artificial Sequence
<220> FEATURE:
<223> OTHER INFORMATION: tMS-Qi gene

<400> SEQUENCE: 9
atgcgtcgta gcgcaaatta tcagccgagc atttggaatc atgattatat tgaaagcctg       60
cgtattgaat atgttggtga aacctgtacc cgtcagatta tgttctgaa agaacaggtt      120 cgtatgatgc tgcataaagt tgttaatccg ctggaacagc tggaactgat tgaaattctg      180
cagcgtctgg gtctgagcta tcattttgaa gaagaaatta aacgtattct ggatggtgtt      240
tataataatg atcatggtgg tgatacctgg aaagcagaaa atctgtatgc aaccgcactg      300
aaatttcgtc tgctgcgtca gcatggttat agcgttagcc aggaagtttt taatagcttt      360
aaagatgaac gtggtagctt taaagcatgt ctgtgtgaag ataccaaagg tatgctgagc      420
ctgtatgaag caagcttttt tctgattgaa ggtgaaaata ttctggaaga agcacgtgat      480
tttagcacca acatctggaa gaatatgtt aaacagaata agaaaaaaa tctggcaacc      540 ctggttaatc atagcctgga atttccgctg cattggcgta tgccgcgtct ggaagcacgt      600
tggtttatta atatttatcg tcataatcag gatgttaatc cgattctgct ggaatttgca      660
gaactggatt ttaatattgt tcaggcagca catcaggcag attttaaaaca ggttagcacc      720 tggtggaaaa gcaccggtct ggttgaaaat ctgagctttg cacgtgatcg tccggttgaa      780
aatttttttt ggaccgttgg tctgattttt cagccgcagt ttggttattg tcgtcgtatg      840
tttaccaaag ttttttgcact gattaccacc attgatgatg tttatgatgt ttatggtacc      900
ctggatgaac tggaactgtt taccgatgtt gttgaacgtt gggatattaa tgcaatggat      960
cagctgccgg attatatgaa atttgttttt ctgaccctgc ataatagcgt taatgaaatg     1020
gcactggata ccatgaaaga acagcgtttt catattatta aatatctgaa aaaagcatgg     1080
gttgatctgt gtcgttatta tctggttgaa gcaaaatggt atagcaataa atatcgtccg     1140
agcctgcagg aatatattga aaatgcatgg attagcattg gtgcaccgac cattctggtt     1200
catgcatatt tttttgttac caatccgatt accaaagaag cactggattg tctggaagaa     1260
tatccgaata ttattcgttg gagcagcatt attgcacgtc tggcagatga tctgggtacc     1320
agcaccgatg aactgaaacg tggtgatgtt ccgaaagcaa ttcagtgtta tatgaatgaa     1380
accggtgcaa gcgaagaagg tgcacgtgaa tatattaaat atctgattag cgcaacctgg     1440
aaaaaaatga ataaagatcg tgcagcaagc agcccgttta gccatatttt tattgaaatt     1500
gcactgaatc tggcacgtat ggcacagtgt ctgtatcagc atggtgatgg tcatggtctg     1560
ggtaatcgtg aaaccaaaga tcgtattctg agcctgctga ttcagccgat tccgctgaat     1620
aaagattaa                                                            1629

<210> SEQ ID NO 10
```

<211> LENGTH: 12195
<212> TYPE: DNA
<213> ORGANISM: Artificial Sequence
<220> FEATURE:
<223> OTHER INFORMATION: pBbA5c-MevT(co)-MBI(co) plasmid vector

<400> SEQUENCE: 10

```
gacgtcggtg cctaatgagt gagctaactt acattaattg cgttgcgctc actgcccgct      60
ttccagtcgg gaaacctgtc gtgccagctg cattaatgaa tcggccaacg cgcggggaga     120
ggcggtttgc gtattgggcg ccagggtggt ttttcttttc accagtgaga cgggcaacag     180
ctgattgccc ttcaccgcct ggccctgaga gagttgcagc aagcggtcca cgctggtttg     240
ccccagcagg cgaaaatcct gtttgatggt ggttaacggc gggatataac atgagctgtc     300
ttcggtatcg tcgtatccca ctaccgagat gtccgcacca acgcgcagcc cggactcggt     360
aatggcgcgc attgcgccca cgccatctg atcgttggca accagcatcg cagtgggaac     420
gatgccctca ttcagcattt gcatggtttg ttgaaaaccg gacatggcac tccagtcgcc     480
ttcccgttcc gctatcggct gaatttgatt gcgagtgaga tatttatgcc agccagccag     540
acgcagacgc gccgagacag aacttaatgg gcccgctaac agcgcgattt gctggtgacc     600
caatgcgacc agatgctcca cgcccagtcg cgtaccgtct tcatgggaga aaataatact     660
gttgatgggt gtctggtcag agacatcaag aaataacgcc ggaacattag tgcaggcagc     720
ttccacagca atggcatcct ggtcatccag cggatagtta atgatcagcc cactgacgcg     780
ttgcgcgaga agattgtgca ccgccgcttt acaggcttcg acgccgcttc gttctaccat     840
cgacaccacc acgctggcac ccagttgatc ggcgcgagat taatcgccg cgacaatttg     900
cgacggcgcg tgcagggcca gactggaggt ggcaacgcca atcagcaacg actgtttgcc     960
cgccagttgt tgtgccacgc ggttgggaat gtaattcagc tccgccatcg ccgcttccac    1020
ttttttcccgc gttttcgcag aaacgtggct ggcctggttc accacgcggg aaacggtctg    1080
ataagagaca ccggcatact ctgcgacatc gtataacgtt actggtttca cattcaccac    1140
cctgaattga ctctcttccg ggcgctatca tgccataccg cgaaaggttt tgcgccattc    1200
gatggtgtcc gggatctcga cgctctccct tatgcgactc ctgcattagg aagcagccca    1260
gtagtaggtt gaggccgttg agcaccgccg ccgcaaggaa tggtgcatgc aaggagatgg    1320
cgcccaacag tccccccggcc acggggcctg ccaccatacc cacgccgaaa caagcgctca    1380
tgagcccgaa gtggcgagcc cgatcttccc catcggtgat gtcggcgata taggcgccag    1440
caaccgcacc tgtggcgccg gtgatgccgg ccacgatgcg tccggcgtag aggatcgaga    1500
tcgtttaggc accccaggct ttacacttta tgcttccggc tcgtataatg tgtggaattg    1560
tgagcggata acaatttcag aattcaaaag atctaaagga ggccatcctg gccatgaaga    1620
actgtgtgat tgtttctgcg gtccgcacgg cgatcggcag ctttaacggc tctttagcga    1680
gcacctctgc aatcgatctg ggtgcgacgg tcattaaggc cgccattgaa cgcgccaaaa    1740
tcgacagcca gcacgttgat gaggtgatca tgggcaatgt gttacaagcc ggcctgggtc    1800
aaaacccagc gcgtcaagca ctgttaaaat ctggtctggc cgagaccgtg tgtggcttca    1860
ccgtcaataa ggtttgcggc tctggcctga gagcgtggcc cctggcagca caagcgattc    1920
aagccggtca ggcacaaagc atcgttgcgg gtggcatgga aacatgtctc tggcgccgt    1980
acttattaga tgccaaagcc cgcagcggtt atcgcctggg cgatggtcag gtgtacgacg    2040
tcatcttacg cgatggctta atgtgcgcga cccacggtta ccacatgggt attacggccg    2100
aaaacgtggc gaaagaatac ggcattacgc gcgagatgca ggatgaatta gcactgcact    2160
```

```
ctcagcgcaa agcagcagcc gcgatcgagt ctggtgcgtt tacggcggaa atcgtgccag    2220
ttaacgtggt cacgcgcaag aagacgttcg ttttcagcca ggacgagttc ccgaaggcaa    2280
acagcaccgc ggaggcctta ggtgccttac gcccagcctt tgacaaagcg ggcacggtca    2340
ccgccggtaa tgcgagcggc atcaatgatg gtgcagcggc actggtcatc atggaagaga    2400
gcgccgcatt agcagcgggt ctgaccccat tagcgcgcat taaatcttat gccagcggcg    2460
gcgtcccacc agccctgatg ggcatgggtc cggtcccagc cacgcaaaaa gccctgcaat    2520
tagcgggcct gcaactggcc gacattgatc tgatcgaggc gaacgaggcg tttgcagcgc    2580
agttcctggc ggtgggtaag aatctgggct tcgacagcga gaaagtcaat gtgaacggtg    2640
gcgcgattgc gttaggccat ccgattggtg caagcggcgc acgcatctta gtgacgttac    2700
tgcacgccat gcaggcacgc gacaagacct taggcctggc gaccttatgt attggtggcg    2760
gtcaaggtat cgccatggtg atcgaacgcc tgaactgatg aaggaggaaa gcaaaatgaa    2820
actgagcacc aagctgtgct ggtgtggcat caagggtcgc ctgcgcccac aaaagcagca    2880
acagctgcac aacacgaacc tgcaaatgac cgagctgaaa aagcagaaga cggccgagca    2940
aaagacccgc ccgcagaacg ttggcatcaa gggcatccag atttatatcc cgacgcagtg    3000
tgtcaaccaa tctgagctgg agaaattcga tggcgtcagc cagggtaagt acaccatcgg    3060
cctgggccag accaacatga gcttcgtgaa cgaccgtgag gacatctatt ctatgagcct    3120
gacggtgctg tctaagctga tcaagagcta caacatcgac acgaataaga tcggtcgtct    3180
ggaggtgggt acgagacgc tgattgacaa gagcaaaagc gtgaagtctg tcttaatgca    3240
gctgttcggc gagaacacgg atgtcgaggg tatcgacacc ctgaacgcgt gttacggcgg    3300
caccaacgca ctgttcaata gcctgaactg gattgagagc aacgcctggg atggccgcga    3360
tgcgatcgtc gtgtgcggcg atatcgccat ctatgacaag ggtgcggcac gtccgaccgg    3420
cggtgcaggc accgttgcga tgtggattgg cccggacgca ccaattgtct tcgattctgt    3480
ccgcgcgtct tacatggagc acgcctacga cttttacaag ccggacttca cgagcgaata    3540
cccgtacgtg gacggccact tctctctgac ctgctatgtg aaggcgctgg accaggttta    3600
taagtcttat agcaaaaagg cgatttctaa gggcctggtc agcgacccgg caggcagcga    3660
cgccctgaac gtgctgaagt atttcgacta caacgtgttc catgtcccga cctgcaaatt    3720
agtgaccaaa tcttatggcc gcctgttata taatgatttc cgtgccaacc cgcagctgtt    3780
cccggaggtt gacgccgagc tggcgacgcg tgattacgac gagagcctga ccgacaagaa    3840
catcgagaag accttcgtca acgtcgcgaa gccgttccac aaaagagcgtg tggcccaaag    3900 cctgatcgtc ccgaccaaca cgggcaacat gtataccgcg tctgtctacg cggcattcgc    3960
gagcctgctg aattacgtcg gttctgacga cctgcagggc aagcgcgttg gcctgttcag    4020
ctacggtagc ggcttagcgg ccagcctgta tagctgcaaa attgtcggcg acgtccagca    4080
catcatcaag gagctggaca tcaccaacaa gctggcgaag cgcatcaccg agacgccgaa    4140
agattacgag gcagcgatcg agttacgcga gaatgcgcat ctgaagaaga acttcaagcc    4200
gcaaggtagc atcgagcacc tgcagagcgg cgtctactac ctgacgaaca ttgacgacaa    4260
gttccgccgt tcttatgacg tcaaaaagta actagtagga ggaaacatc atggtgctga    4320 cgaacaaaac cgtcattagc ggcagcaagg tgaagtctct gagcagcgcc caaagctcta    4380
gcagcggccc gtctagcagc agcgaggagg acgacagccg tgacattgag tctctggaca    4440
agaagatccg cccgctggag gagttagagg ccctgctgag cagcggcaac accaagcagc    4500
```

```
tgaagaacaa ggaagttgca gcgctggtga tccacggtaa gctgccactg tatgcgctgg    4560
aaaagaaact gggcgatacg acgcgtgcgg tcgcggtgcg tcgcaaagcc ttaagcatct    4620
tagcggaggc cccggtgtta gccagcgacc gcctgccgta caagaactac gactacgacc    4680
gcgtgtttgg cgcgtgctgc gagaatgtca ttggctacat gccgttaccg gttggtgtga    4740
tcggcccgct ggtcattgat ggcacgagct atcacattcc aatggcgacc acggaaggtt    4800
gcttagtcgc cagcgccatg cgtggctgta aggcgattaa cgccggcggt ggcgcgacga    4860
ccgtgttaac caaggatggt atgacgcgcg gtccggtcgt ccgcttccca acgctgaagc    4920
gcagcggcgc gtgtaagatt tggctggatt ctgaggaggg ccaaaacgcg atcaagaaag    4980
ccttcaactc tacgagccgt ttcgcgcgtt tacagcatat ccagacctgc ctggccggcg    5040
acctgctgtt catgcgcttc cgcaccacca cgggcgatgc gatgggcatg aacatgatca    5100
gcaagggcgt cgaatatagc ctgaaacaaa tggtggaaga atatggctgg gaggacatgg    5160
aggttgtctc tgtgagcggc aactattgca ccgacaagaa gccggcagcc attaactgga    5220
ttgagggtcg cggcaaaagc gtcgtggcag aagcgaccat cccaggcgac gtggtccgta    5280
aggttctgaa gagcgacgtc agcgccctgg ttgagttaaa tatcgcgaaa aacctggtcg    5340
gcagcgcgat ggcgggcagc gtgggtggct ttaacgcaca tgcagcgaat ctggttacgg    5400
cggttttctt agccttaggt caggacccag cccaaaatgt cgagagcagc aactgcatta    5460
ccttaatgaa agaggttgac ggtgacctgc gcatcagcgc ttctatgccg tctatcgagg    5520
tcggcacgat cggcggcggc accgttttag aaccgcaagg tgcgatgctg gatctgctgg    5580
gcgtgcgcgg cccacatgca acggcccag gcaccaatgc cgccaactg gcccgtatcg    5640 tggcctgcgc ggttctggcg ggtgagctga gcctgtgcgc cgcattagcc gcgggccatt    5700
tagttcaatc tcacatgacc cacaaccgca agcggcaga accaaccaag ccaaataacc    5760
tggacgcaac cgacattaac cgtctgaagg atggcagcgt cacgtgcatt aaaagctgag    5820
gatctaggag gaaataacca tgtctctgcc attcctgacg tctgcgccag gtaaggtgat    5880
catcttcggc gagcactctg cggtgtacaa taagccggcc gtcgccgcct ctgtgtctgc    5940
gttacgcacc tacctgctga tcagcgaatc ttctgcaccg gacacgatcg agctggactt    6000
tccggacatc agcttcaacc acaagtggag catcaacgac ttcaacgcga tcacggagga    6060
ccaggtgaac agccaaaagc tggccaaagc ccagcaagca accgacggtc tgtctcagga    6120
gctggtgtct ctgctggacc gctgttagc gcagttaagc gagagcttcc attaccacgc    6180
cgcgttctgc ttcctgtaca tgttcgtttg cctgtgcccg cacgcaaaga acatcaagtt    6240
cagcctgaag agcacgctgc cgattggcgc aggcttaggc tctagcgcat ctatcagcgt    6300
gagcctggcg ctggcgatgg cctatctggg tggcctgatt ggcagcaacg acctggagaa    6360
actgagcgaa aacgacaagc acatcgtgaa ccagtgggcc tttatcggcg agaagtgcat    6420
tcatggcacc ccgagcggca ttgacaacgc agttgccacg tatggcaacg ccctgctgtt    6480
cgagaaagac agccacaacg gcacgatcaa cacgaacaac ttcaagttcc tggacgactt    6540
cccggcgatc ccgatgattc tgacctacac ccgtatccca cgcagcacca aggatttagt    6600
cgcccgcgtg cgtgttttag tcaccgaaaa gttcccggag gtgatgaagc cgatcctgga    6660
cgcgatgggc gagtgcgcgc tgcagggtct ggagatcatg accaagctga gcaagtgcaa    6720
gggcaccgac gatgaggcgg tggagaccaa caatgagctg tacgagcagc tgctggagct    6780
gatccgtatc aatcacggcc tgctggtctc tatcggtgtg tctcacccgg gcctggaact    6840
gatcaaaaac ctgagcgacg acctgcgcat tggctctacg aaattaacgg gtgcaggtgg    6900
```

```
cggtggctgc tctttaacgc tgctgcgccg tgacattacg caggagcaaa tcgacagctt    6960
caagaagaag ctgcaggacg acttcagcta cgagacgttc gagacggacc tgggcggcac    7020
gggctgttgc ctgctgagcg ccaaaaatct gaacaaggac ctgaagatca aaagcctggt    7080
gttccagctg ttcgaaaaca agacgaccac gaagcagcag atcgacgacc tgttactgcc    7140
gggtaacacc aatctgccgt ggacgtctta aggatctagg agggagatca tatgagcgaa    7200
ttacgtgcat tcagcgcgcc aggtaaggca ctgctggccg gtggctacct ggtgttagac    7260
accaagtacg aggcgttcgt cgtcggctta tctgcccgta tgcatgcagt tgcccacccg    7320
tatggtagcc tgcagggctc tgacaagttc gaagtgcgtg tgaagagcaa gcagttcaag    7380
gacggcgagt ggctgtacca cattagccca agagcggct tcatcccggt tagcattggt    7440
ggcagcaaga acccatttat cgagaaggtc attgccaacg tcttcagcta cttcaagccg    7500
aatatggacg attactgcaa ccgcaacctg ttcgtcatcg acattttcag cgacgacgcg    7560
taccacagcc aagaggactc tgttacggag catcgtggta accgccgcct gagcttccac    7620
agccatcgca ttgaggaggt gccgaagacg gtctgggtt ctagcgccgg tttagttacc    7680
gtcttaacga cggcgttagc gagcttcttc gtgagcgacc tggagaacaa cgtgacaag    7740 taccgcgaag tgattcataa cctggcgcag gtggcacatt gtcaggccca aggtaagatt    7800
ggctctggtt ttgatgtggc agcggccgcc tatggctcta ccgctatcg ccgctttccg    7860 ccggccctga tcagcaatct gccggacatc ggctctgcga cgtatggtag caaactggcg    7920
catctggtgg acgaagaaga ctggaacatc accattaagt ctaatcacct gccgagcggc    7980
ttaacgttat ggatgggcga tatcaagaac ggcagcgaaa cggttaagct ggtgcagaaa    8040
gtgaaaaact ggtacgacag ccacatgccg gaaagcctga agatttacac ggagctggac    8100
cacgccaata gccgtttcat ggatggtctg agcaagctgg accgcctgca cgaaacccac    8160
gacgactaca gcgaccaaat cttcgagagc ctggagcgca atgactgcac ctgccagaag    8220
tacccggaga tcacggaggt ccgcgatgcc gtggcaacga ttcgccgtag cttccgcaaa    8280
attacgaagg agagcggcgc ggatatcgaa ccaccggtcc agacgtctct gctggacgac    8340
tgtcaaacct taagggcgt gttaacgtgc ctgattccgg gcgcgggtgg ttacgacgcc    8400
attgccgtca tcacgaaaca ggacgtcgat ctgcgcgcac aaacggccaa cgacaaacgt    8460
ttcagcaaag tccaatggct ggatgttacg caggccgact ggggtgttcg caaggagaag    8520
gacccggaaa cgtatctgga taagtgagga tctaggagga ttatgagatg accgtttaca    8580
cagcatccgt taccgcaccc gtcaacatcg caacccttaa gtattggggg aaaagggaca    8640
cgaagttgaa tctgcccacc aattcgtcca tatcagtgac tttatcgcaa gatgacctca    8700
gaacgttgac ctctgcggct actgcacctg agtttgaacg cgacactttg tggttaaatg    8760
gagaaccaca cagcatcgac aatgaaagaa ctcaaaattg tctgcgcgac ctacgccaat    8820
taagaaagga aatggaatcg aaggacgcct cattgcccac attatctcaa tggaaactcc    8880
acattgtctc cgaaaataac tttcctacag cagctggttt agcttcctcc gctgctggct    8940
ttgctgcatt ggtctctgca attgctaagt tataccaatt accacagtca acttcagaaa    9000
tatctagaat agcaagaaag gggtctggtt cagcttgtag atcgttgttt ggcggatacg    9060
tggcctggga aatgggaaaa gctgaagatg gtcatgattc catggcagta caaatcgcag    9120
acagctctga ctggcctcag atgaaagctt gtgtcctagt tgtcagcgat attaaaaagg    9180
atgtgagttc cactcagggt atgcaattga ccgtggcaac ctccgaacta tttaaagaaa    9240
```

```
gaattgaaca tgtcgtacca aagagatttg aagtcatgcg taaagccatt gttgaaaaag   9300
atttcgccac ctttgcaaag gaaacaatga tggattccaa ctctttccat gccacatgtt   9360
tggactcttt ccctccaata ttctacatga atgacacttc caagcgtatc atcagttggt   9420
gccacaccat taatcagttt tacggagaaa caatcgttgc atacacgttt gatgcaggtc   9480
caaatgctgt gttgtactac ttagctgaaa atgagtcgaa actctttgca tttatctata   9540
aattgtttgg ctctgttcct ggatgggaca agaaatttac tactgagcag cttgaggctt   9600
tcaaccatca atttgaatca tctaacttta ctgcacgtga attggatctt gagttgcaaa   9660
aggatgttgc cagagtgatt ttaactcaag tcggttcagg cccacaagaa acaaacgaat   9720
ctttgattga cgcaaagact ggtctaccaa aggaataagg atctaggagg taatgataat   9780
gcaaacggaa cacgtcattt tattgaatgc acagggagtt cccacgggta cgctggaaaa   9840
gtatgccgca cacacggcag acacccgctt acatctcgcg ttctccagtt ggctgtttaa   9900
tgccaaagga caattattag ttacccgccg cgcactgagc aaaaaagcat ggcctggcgt   9960
gtggactaac tcggtttgtg ggcacccaca actgggagaa agcaacgaag acgcagtgat  10020
ccgccgttgc cgttatgagc ttggcgtgga aattacgcct cctgaatcta tctatcctga  10080
cttccgctac cgcgccaccg atccgagtgg cattgtggaa aatgaagtgt gtccggtatt  10140
tgccgcacgc accactagtg cgttacagat caatgatgat gaagtgatgg attatcaatg  10200
gtgtgattta gcagatgtat tacacggtat tgatgccacg ccgtgggcgt tcagtccgtg  10260
gatggtgatg caggcgacaa atcgcgaagc cagaaaacga ttatctgcat ttacccagct  10320
taaataagga tccaaactcg agtaaggatc tccaggcatc aaataaaacg aaaggctcag  10380
tcgaaagact gggcctttcg ttttatctgt tgtttgtcgg tgaacgctct ctactagagt  10440
cacactggct caccttcggg tgggcctttc tgcgtttata cctagggata tattccgctt  10500
cctcgctcac tgactcgcta cgctcggtcg ttcgactgcg gcgagcggaa atggcttacg  10560
aacggggcgg agatttcctg gaagatgcca ggaagatact aacagggaa gtgagagggc  10620 cgcggcaaag ccgttttcc ataggctccg ccccctgac aagcatcacg aaatctgacg  10680
ctcaaatcag tggtggcgaa acccgacagg actataaaga taccaggcgt ttccccctgg  10740
cggctccctc gtgcgctctc ctgttcctgc ctttcggttt accggtgtca ttccgctgtt  10800
atggccgcgt ttgtctcatt ccacgcctga cactcagttc cgggtaggca gttcgctcca  10860
agctggactg tatgcacgaa ccccccgttc agtccgaccg ctgcgcctta tccggtaact  10920
atcgtcttga gtccaacccg gaaagacatg caaaagcacc actggcagca gccactggta  10980
attgatttag aggagttagt cttgaagtca tgcgccggtt aaggctaaac tgaaaggaca  11040
agttttggtg actgcgctcc tccaagccag ttacctcggt tcaaagagtt ggtagctcag  11100
agaaccttcg aaaaaccgcc ctgcaaggcg gttttttcgt tttcagagca agagattacg  11160
cgcagaccaa aacgatctca agaagatcat cttattaatc agataaaata tttctagatt  11220
tcagtgcaat ttatctcttc aaatgtagca cctgaagtca gccccatacg atataagttg  11280
ttactagtgc ttggattctc accaataaaa aacgcccggc ggcaaccgag cgttctgaac  11340
aaatccagat ggagttctga ggtcattact ggatctatca acaggagtcc aagcgagctc  11400
gatatcaaat tacgccccgc cctgccactc atcgcagtac tgttgtaatt cattaagcat  11460
tctgccgaca tggaagccat cacaaacggc atgatgaacc tgaatcgcca gcggcatcag  11520
caccttgtcg ccttgcgtat aatatttgcc catggtgaaa acgggggcga agaagttgtc  11580
catattggcc acgtttaaat caaaactggt gaaactcacc cagggattgg ctgagacgaa  11640
```

```
aaacatattc tcaataaacc ctttagggaa ataggccagg ttttcaccgt aacacgccac    11700
atcttgcgaa tatatgtgta gaaactgccg gaaatcgtcg tggtattcac tccagagcga    11760
tgaaaacgtt tcagtttgct catggaaaac ggtgtaacaa gggtgaacac tatcccatat    11820
caccagctca ccgtctttca ttgccatacg aaattccgga tgagcattca tcaggcgggc    11880
aagaatgtga ataaaggccg gataaaactt gtgcttattt ttctttacgg tcttaaaaa    11940 ggccgtaata tccagctgaa cggtctggtt ataggtacat tgagcaactg actgaaatgc    12000
ctcaaaatgt tctttacgat gccattggga tatatcaacg gtggtatatc cagtgatttt    12060
tttctccatt ttagcttcct tagctcctga aatctcgat aactcaaaaa atacgcccgg    12120
tagtgatctt atttcattat ggtgaaagtt ggaacctctt acgtgccgat caacgtctca    12180
ttttcgccag atatc                                                    12195

<210> SEQ ID NO 11
<211> LENGTH: 13118
<212> TYPE: DNA
<213> ORGANISM: Artificial Sequence
<220> FEATURE:
<223> OTHER INFORMATION: pBbA5c-MevT(co)-MBIG(co) plasmid vector

<400> SEQUENCE: 11
gacgtcggtg cctaatgagt gagctaactt acattaattg cgttgcgctc actgcccgct      60
ttccagtcgg gaaacctgtc gtgccagctg cattaatgaa tcggccaacg cgcggggaga     120
ggcggtttgc gtattgggcg ccagggtggt ttttcttttc accagtgaga cgggcaacag     180
ctgattgccc ttcaccgcct ggccctgaga gagttgcagc aagcggtcca cgctggtttg     240
ccccagcagg cgaaaatcct gtttgatggt ggttaacggc gggatataac atgagctgtc     300 tcggtatcg tcgtatccca ctaccgagat gtccgcacca acgcgcagcc cggactcggt     360
aatggcgcgc attgcgccca gcgccatctg atcgttggca accagcatcg cagtgggaac     420
gatgccctca ttcagcattt gcatggtttg ttgaaaaccg gacatggcac tccagtcgcc     480
ttcccgttcc gctatcggct gaatttgatt gcgagtgaga tatttatgcc agccagccag     540
acgcagacgc gccgagacag aacttaatgg gcccgctaac agcgcgattt gctggtgacc     600
caatgcgacc agatgctcca cgcccagtcg cgtaccgtct tcatgggaga aaataatact     660
gttgatgggt gtctggtcag agacatcaag aaataacgcc ggaacattag tgcaggcagc     720
ttccacagca atggcatcct ggtcatccag cggatagtta atgatcagcc cactgacgcg     780
ttgcgcgaga agattgtgca ccgccgcttt acaggcttcg acgccgcttc gttctaccat     840
cgacaccacc acgctggcac ccagttgatc ggcgcgagat taatcgccg cgacaatttg     900 cgacggcgcg tgcagggcca gactggaggt ggcaacgcca atcagcaacg actgtttgcc     960
cgccagttgt tgtgccacgc ggttgggaat gtaattcagc tccgccatcg ccgcttccac    1020 ttttcccgc gttttcgcag aaacgtggct ggcctggttc accacgcggg aaacggtctg    1080
ataagagaca ccggcatact ctgcgacatc gtataacgtt actggtttca cattcaccac    1140
cctgaattga ctctcttccg ggcgctatca tgccataccg cgaaaggttt tgcgccattc    1200
gatggtgtcc gggatctcga cgctctccct tatgcgactc ctgcattagg aagcagccca    1260
gtagtaggtt gaggccgttg agcaccgccg ccgcaaggaa tggtgcatgc aaggagatgg    1320
cgcccaacag tcccccggcc acggggcctg ccaccatacc cacgccgaaa caagcgctca    1380
tgagcccgaa gtggcgagcc cgatcttccc catcggtgat gtcggcgata taggcgccag    1440
```

-continued

```
caaccgcacc tgtggcgccg gtgatgccgg ccacgatgcg tccggcgtag aggatcgaga    1500
tcgtttaggc accccaggct ttacacttta tgcttccggc tcgtataatg tgtggaattg    1560
tgagcggata acaatttcag aattcaaaag atctaaagga ggccatcctg gccatgaaga    1620
actgtgtgat tgtttctgcg gtccgcacgg cgatcggcag ctttaacggc tctttagcga    1680
gcacctctgc aatcgatctg ggtgcgacgg tcattaaggc cgccattgaa cgcgccaaaa    1740
tcgacagcca gcacgttgat gaggtgatca tgggcaatgt gttacaagcc ggcctgggtc    1800
aaaacccagc gcgtcaagca ctgttaaaat ctggtctggc cgagaccgtg tgtggcttca    1860
ccgtcaataa ggtttgcggc tctggcctga gagcgtggc cctggcagca caagcgattc     1920
aagccggtca ggcacaaagc atcgttgcgg gtggcatgga aacatgtct ctggcgccgt     1980 acttattaga tgccaaagcc cgcagcggtt atcgcctggg cgatggtcag gtgtacgacg    2040
tcatcttacg cgatggctta atgtgcgcga cccacggtta ccacatgggt attacggccg    2100
aaaacgtggc gaaagaatac ggcattacgc gcgagatgca ggatgaatta gcactgcact    2160
ctcagcgcaa agcagcagcc gcgatcgagt ctggtgcgtt tacggcggaa atcgtgccag    2220
ttaacgtggt cacgcgcaag aagacgttcg ttttcagcca ggacgagttc ccgaaggcaa    2280
acagcaccgc ggaggcctta ggtgcctac  gcccagcctt tgacaaagcg gcacggtca     2340 ccgccggtaa tgcgagcggc atcaatgatg gtgcagcggc actggtcatc atggaagaga    2400
gcgccgcatt agcagcgggt ctgacccat tagcgcgcat taaatcttat gccagcggcg     2460
gcgtcccacc agccctgatg gcatgggtc cggtcccagc cacgcaaaaa gccctgcaat     2520
tagcgggcct gcaactggcc gacattgatc tgatcgaggc gaacgaggcg tttgcagcgc    2580
agttcctggc ggtgggtaag aatctgggct tcgacagcga gaaagtcaat gtgaacggtg    2640
gcgcgattgc gttaggccat ccgattggtg caagcggcgc acgcatctta gtgacgttac    2700
tgcacgccat gcaggcacgc gacaagacct taggcctggc gaccttatgt attggtggcg    2760
gtcaaggtat cgccatggtg atcgaacgcc tgaactgatg aaggaggaaa gcaaaatgaa    2820
actgagcacc aagctgtgct ggtgtggcat caagggtcgc ctgcgcccac aaaagcagca    2880
acagctgcac aacacgaacc tgcaaatgac cgagctgaaa aagcagaaga cggccgagca    2940
aaagacccgc ccgcagaacg ttggcatcaa gggcatccag atttatatcc cgacgcagtg    3000
tgtcaaccaa tctgagctgg agaaattcga tggcgtcagc cagggtaagt acaccatcgg    3060
cctgggccag accaacatga gcttcgtgaa cgaccgtgag gacatctatt ctatgagcct    3120
gacggtgctg tctaagctga tcaagagcta caacatcgac acgaataaga tcggtcgtct    3180
ggaggtgggt acggagacgc tgattgacaa gagcaaaagc gtgaagtctg tcttaatgca    3240
gctgttcggc gagaacacgg atgtcgaggg tatcgacacc ctgaacgcgt gttacgcgg    3300 caccaacgca ctgttcaata gcctgaactg gattgagagc aacgcctggg atggccgcga    3360
tgcgatcgtc gtgtgcggcg atatcgccat ctatgacaag ggtgcggcac gtccgaccgg    3420
cggtgcaggc accgttgcga tgtggattgg cccggacgca ccaattgtct tcgattctgt    3480
ccgcgcgtct tacatggagc acgcctacga cttttacaag ccggacttca cgagcgaata    3540
cccgtacgtg gacggccact tctctctgac ctgctatgtg aaggcgctgg accaggttta    3600
taagtcttat agcaaaaagg cgatttctaa gggcctggtc agcgacccgg caggcagcga    3660
cgccctgaac gtgctgaagt atttcgacta caacgtgttc catgtcccga cctgcaaatt    3720
agtgaccaaa tcttatggcc gcctgttata taatgatttc cgtgccaacc cgcagctgtt    3780
cccggaggtt gacgccgagc tggcgacgcg tgattacgac gagagcctga ccgacaagaa    3840
```

```
catcgagaag accttcgtca acgtcgcgaa gccgttccac aaagagcgtg tggcccaaag    3900
cctgatcgtc ccgaccaaca cgggcaacat gtataccgcg tctgtctacg cggcattcgc    3960
gagcctgctg aattacgtcg gttctgacga cctgcagggc aagcgcgttg gcctgttcag    4020
ctacggtagc ggcttagcgg ccagcctgta tagctgcaaa attgtcggcg acgtccagca    4080
catcatcaag gagctggaca tcaccaacaa gctggcgaag cgcatcaccg agacgccgaa    4140
agattacgag gcagcgatcg agttacgcga gaatgcgcat ctgaagaaga acttcaagcc    4200
gcaaggtagc atcgagcacc tgcagagcgg cgtctactac ctgacgaaca ttgacgacaa    4260
gttccgccgt tcttatgacg tcaaaaagta actagtagga ggaaaacatc atggtgctga    4320
cgaacaaaac cgtcattagc ggcagcaagg tgaagtctct gagcagcgcc aaagctcta     4380
gcagcggccc gtctagcagc agcgaggagg acgacagccg tgacattgag tctctggaca    4440
agaagatccg cccgctggag gagttagagg ccctgctgag cagcggcaac accaagcagc    4500
tgaagaacaa ggaagttgca cgcgctggtga tccacggtaa gctgccactg tatgcgctgg    4560
aaaagaaact gggcgatacg acgcgtgcgg tcgcggtgcg tcgcaaagcc ttaagcatct    4620
tagcggaggc cccggtgtta gccagcgacc gcctgccgta caagaactac gactacgacc    4680
gcgtgtttgg cgcgtgctgc gagaatgtca ttggctacat gccgttaccg gttggtgtga    4740
tcggcccgct ggtcattgat ggcacgagct atcacattcc aatggcgacc acggaaggtt    4800
gcttagtcgc cagcgccatg cgtggctgta aggcgattaa cgccggcggt ggcgcgacga    4860
ccgtgttaac caaggatggt atgacgcgcg gtccggtcgt ccgcttccca acgctgaagc    4920
gcagcggcgc gtgtaagatt tggctggatt ctgaggaggg ccaaaacgcg atcaagaaag    4980
ccttcaactc tacgagccgt ttcgcgcgtt tacagcatat ccagacctgc ctggccggcg    5040
acctgctgtt catgcgcttc cgcaccacca cgggcgatgc gatgggcatg aacatgatca    5100
gcaagggcgt cgaatatagc ctgaaacaaa tggtggaaga atatggctgg gaggacatgg    5160
aggttgtctc tgtgagcggc aactattgca ccgacaagaa gccggcagcc attaactgga    5220
ttgagggtcg cggcaaaagc gtcgtggcag aagcgaccat cccaggcgac gtggtccgta    5280
aggttctgaa gagcgacgtc agcgccctgg ttgagttaaa tatcgcgaaa aacctggtcg    5340
gcagcgcgat ggcggggcagc gtgggtggct taacgcaca tgcagcgaat ctggttacgg    5400
cggttttctt agccttaggt caggacccag cccaaaatgt cgagagcagc aactgcatta    5460
ccttaatgaa agaggttgac ggtgacctgc gcatcagcgt ttctatgccg tctatcgagg    5520
tcggcacgat cggcggcggc accgttttag aaccgcaagg tgcgatgctg atctgctgg     5580
gcgtgcgcgg cccacatgca acggcccag gcaccaatgc cgccaactg gcccgtatcg      5640
tggcctgcgc ggttctggcg ggtgagctga gcctgtgcgc cgcattagcc gcgggccatt    5700
tagttcaatc tcacatgacc cacaaccgca agccggcaga accaaccaag ccaaataacc    5760
tggacgcaac cgacattaac cgtctgaagg atggcagcgt cacgtgcatt aaaagctgag    5820
gatctaggag gaaataacca tgtctctgcc attcctgacg tctgcgccag gtaaggtgat    5880
catcttcggc gagcactctg cggtgtacaa taagccggcc gtcgccgcct ctgtgtctgc    5940
gttacgcacc tacctgctga tcagcgaatc ttctgcaccg gacacgatcg agctggactt    6000
tccggacatc agcttcaacc acaagtggag catcaacgac ttcaacgcga tcacggagga    6060
ccaggtgaac agccaaaagc tggccaaagc ccagcaagca accgacggtc tgtctcagga    6120
gctggtgtct ctgctggacc cgctgttagc gcagttaagc gagagcttcc attaccacgc    6180
```

```
cgcgttctgc ttcctgtaca tgttcgtttg cctgtgcccg cacgcaaaga acatcaagtt    6240
cagcctgaag agcacgctgc cgattggcgc aggcttaggc tctagcgcat ctatcagcgt    6300
gagcctggcg ctggcgatgg cctatctggg tggcctgatt ggcagcaacg acctggagaa    6360
actgagcgaa aacgcaaagc acatcgtgaa ccagtgggcc tttatcggcg agaagtgcat    6420
tcatggcacc ccgagcggca ttgacaacgc agttgccacg tatggcaacg ccctgctgtt    6480
cgagaaagac agccacaacg gcacgatcaa cacgaacaac ttcaagttcc tggacgactt    6540
cccggcgatc ccgatgattc tgacctacac ccgtatccca cgcagcacca aggatttagt    6600
cgcccgcgtg cgtgttttag tcaccgaaaa gttcccggag gtgatgaagc cgatcctgga    6660
cgcgatgggc gagtgcgcgc tgcagggtct ggagatcatg accaagctga gcaagtgcaa    6720
gggcaccgac gatgaggcgg tggagaccaa caatgagctg tacgagcagc tgctggagct    6780
gatccgtatc aatcacggcc tgctggtctc tatcggtgtg tctcacccgg gcctggaact    6840
gatcaaaaac ctgagcgacg acctgcgcat tggctctacg aaattaacgg gtgcaggtgg    6900
cggtggctgc tctttaacgc tgctgcgccg tgacattacg caggagcaaa tcgacagctt    6960
caagaagaag ctgcaggacg acttcagcta cgagacgttc gagacggacc tgggcggcac    7020
gggctgttgc ctgctgagcg ccaaaaatct gaacaaggac ctgaagatca aaagcctggt    7080
gttccagctg ttcgaaaaca agacgaccac gaagcagcag atcgacgacc tgttactgcc    7140
gggtaacacc aatctgccgt ggacgtctta aggatctagg agggagatca tatgagcgaa    7200
ttacgtgcat tcagcgcgcc aggtaaggca ctgctggccg gtggctacct ggtgttagac    7260
accaagtacg aggcgttcgt cgtcggctta tctgcccgta tgcatgcagt tgcccacccg    7320
tatggtagcc tgcagggctc tgacaagttc gaagtgcgtg tgaagagcaa gcagttcaag    7380
gacggcgagt ggctgtacca cattagccca aagagcggct tcatcccggt tagcattggt    7440
ggcagcaaga acccatttat cgagaaggtc attgccaacg tcttcagcta cttcaagccg    7500
aatatggacg attactgcaa ccgcaacctg ttcgtcatcg acattttcag cgacgacgcg    7560
taccacagcc aagaggactc tgttacggag catcgtggta accgccgcct gagcttccac    7620
agccatcgca ttgaggaggt gccgaagacg ggtctgggtt ctagcgccgg tttagttacc    7680
gtcttaacga cggcgttagc gagcttcttc gtgagcgacc tggagaacaa cgtggacaag    7740
taccgcgaag tgattcataa cctggcgcag gtggcacatt gtcaggccca aggtaagatt    7800
ggctctggtt ttgatgtggc agcggccgcc tatggctcta tccgctatcg ccgcttttcg    7860
ccggccctga tcagcaatct gccggacatc ggctctgcga cgtatggtag caaactggcg    7920
catctggtgg acgaagaaga ctggaacatc accattaagt ctaatcacct gccgagcggc    7980
ttaacgttat ggatgggcga tatcaagaac ggcagcgaaa cggttaagct ggtgcagaaa    8040
gtgaaaaact ggtacgacag ccacatgccg gaaagcctga gatttacac ggagctggac    8100 cacgccaata gccgtttcat ggatggtctg agcaagctgg accgcctgca cgaaacccac    8160
gacgactaca gcgaccaaat cttcgagagc ctggagcgca atgactgcac ctgccagaag    8220
tacccggaga tcacggaggt ccgcgatgcc gtggcaacga ttcgccgtag cttccgcaaa    8280
attacgaagg agagcggcgc ggatatcgaa ccaccggtcc agacgtctct gctggacgac    8340
tgtcaaacct taagggcgt gttaacgtgc ctgattccgg gcgcgggtgg ttacgacgcc    8400
attgccgtca tcacgaaaca ggacgtcgat ctgcgcgcac aaacggccaa cgacaaacgt    8460
ttcagcaaag tccaatggct ggatgttacg caggccgact ggggtgttcg caaggagaag    8520
gacccggaaa cgtatctgga taagtgagga tctaggagga ttatgagatg accgtttaca    8580
```

```
cagcatccgt taccgcaccc gtcaacatcg caacccttaa gtattggggg aaaagggaca    8640
cgaagttgaa tctgcccacc aattcgtcca tatcagtgac tttatcgcaa gatgacctca    8700
gaacgttgac ctctgcggct actgcacctg agtttgaacg cgacactttg tggttaaatg    8760
gagaaccaca cagcatcgac aatgaaagaa ctcaaaattg tctgcgcgac ctacgccaat    8820
taagaaagga aatggaatcg aaggacgcct cattgcccac attatctcaa tggaaactcc    8880
acattgtctc cgaaaataac tttcctacag cagctggttt agcttcctcc gctgctggct    8940
ttgctgcatt ggtctctgca attgctaagt ataccaatt accacagtca acttcagaaa     9000
tatctagaat agcaagaaag gggtctggtt cagcttgtag atcgttgttt ggcggatacg    9060
tggcctggga aatgggaaaa gctgaagatg gtcatgattc catggcagta caaatcgcag    9120
acagctctga ctggcctcag atgaaagctt gtgtcctagt tgtcagcgat attaaaaagg    9180
atgtgagttc cactcagggt atgcaattga ccgtggcaac ctccgaacta tttaaagaaa    9240
gaattgaaca tgtcgtacca aagagatttg aagtcatgcg taaagccatt gttgaaaaag    9300
atttcgccac ctttgcaaag gaaacaatga tggattccaa ctctttccat gccacatgtt    9360
tggactcttt ccctccaata ttctacatga atgcacttc caagcgtatc atcagttggt     9420
gccacaccat taatcagttt tacggagaaa caatcgttgc atacacgttt gatgcaggtc    9480
caaatgctgt gttgtactac ttagctgaaa atgagtcgaa actctttgca tttatctata    9540
aattgtttgg ctctgttcct ggatgggaca agaaatttac tactgagcag cttgaggctt    9600
tcaaccatca atttgaatca tctaaccttta ctgcacgtga attggatctt gagttgcaaa    9660
aggatgttgc cagagtgatt ttaactcaag tcggttcagg cccacaagaa acaaacgaat    9720
ctttgattga cgcaaagact ggtctaccaa aggaataagg atctaggagg taatgataat    9780
gcaaacggaa cacgtcattt tattgaatgc acagggagtt cccacgggta cgctggaaaa    9840
gtatgccgca cacacggcag acacccgctt acatctcgcg ttctccagtt ggctgtttaa    9900
tgccaaagga caattattag ttacccgccg cgcactgagc aaaaaagcat ggcctggcgt    9960
gtggactaac tcggtttgtg ggcacccaca actgggagaa agcaacgaag acgcagtgat    10020
ccgccgttgc cgttatgagc ttggcgtgga aattacgcct cctgaatcta tctatcctga    10080
ctttcgctac cgcgccaccg atccgagtgg cattgtggaa aatgaagtgt gtccggtatt    10140
tgccgcacgc accactagtg cgttacagat caatgatgat gaagtgatgg attatcaatg    10200
gtgtgattta gcagatgtat tacacggtat tgatgccacg ccgtgggcgt tcagtccgtg    10260
gatggtgatg caggcgacaa atcgcgaagc cagaaaacga ttatctgcat ttacccagct    10320
taaataagga tcttttaaga aggagatata catatggtgg aatttgattt taacaaatat    10380
atggatagca aagcgatgac cgtgaacgaa gcgctgaaca aagcgattcc gctgcgctat    10440
ccgcagaaaa tttatgaaag catgcgctat agcctgctgg cgggcggcaa acgcgtgcgc    10500
ccggtgctgt gcattgcggc gtgcgaactg gtgggcggca ccgaagaact ggcgattccg    10560
accgcgtgcg cgattgaaat gattcatacc atgagcctga tgcatgatga tctgccgtgc    10620
attgataacg atgatctgcg ccgcggcaaa ccgaccaacc ataaaatttt tggcgaagat    10680
accgcggtga ccgcgggcaa cgcgctgcat agctatgcgt ttgaacatat tgcggtgagc    10740
accagcaaaa ccgtgggcgc ggatcgcatt ctgcgcatgg tgagcgaact gggccgcgcg    10800
accggcagcg aaggcgtgat gggcggccag atggtggata ttgcgagcga aggcgatccg    10860
agcattgatc tgcagaccct ggaatggatt catattcata aaccgcgat gctgctggaa    10920
```

```
tgcagcgtgg tgtgcggcgc gattattggc ggcgcgagcg aaattgtgat tgaacgcgcg   10980
cgccgctatg cgcgctgcgt gggcctgctg tttcaggtgg tggatgatat tctggatgtg   11040
accaaaagca gcgatgaact gggcaaaacc gcgggcaaag atttaattag cgataaagcg   11100
acctatccga aactgatggg cctggaaaaa gcgaaagaat ttagcgatga actgctgaac   11160
cgcgcgaaag gcgaactgag ctgctttgat ccggtgaaag cggcgccgct gctgggcctg   11220
gcggattatg tggcgtttcg ccagaactaa ggatccaaac tcgagtaagg atctccaggc   11280
atcaaataaa acgaaaggct cagtcgaaag actgggcctt tcgttttatc tgttgtttgt   11340
cggtgaacgc tctctactag agtcacactg gctcaccttc gggtgggcct ttctgcgttt   11400
atacctaggg atatattccg cttcctcgct cactgactcg ctacgctcgg tcgttcgact   11460
gcggcgagcg gaaatggctt acgaacgggg cggagatttc ctggaagatg ccaggaagat   11520
acttaacagg gaagtgagag ggccgcggca agccgttttt ccataggctc cgcccccct   11580 gacaagcatc acgaaatctg acgctcaaat cagtggtggc gaaacccgac aggactataa   11640
agataccagg cgtttccccc tggcggctcc ctcgtgcgct ctcctgttcc tgcctttcgg   11700
tttaccggtg tcattccgct gttatggccg cgtttgtctc attccacgcc tgacactcag   11760
ttccgggtag gcagttcgct ccaagctgga ctgtatgcac gaaccccccg ttcagtccga   11820
ccgctgcgcc ttatccggta actatcgtct tgagtccaac ccggaaagac atgcaaaagc   11880
accactggca gcagccactg gtaattgatt tagaggagtt agtcttgaag tcatgcgccg   11940
gttaaggcta aactgaaagg acaagttttg gtgactgcgc tcctccaagc cagttacctc   12000
ggttcaaaga gttggtagct cagagaacct tcgaaaaacc gccctgcaag cggttttt    12060 cgttttcaga gcaagagatt acgcgcagac caaaacgatc tcaagaagat catcttatta   12120
atcagataaa atatttctag atttcagtgc aatttatctc ttcaaatgta gcacctgaag   12180
tcagccccat acgatataag ttgttactag tgcttggatt ctcaccaata aaaaacgccc   12240
ggcggcaacc gagcgttctg aacaaatcca gatggagttc tgaggtcatt actgatcta    12300 tcaacaggag tccaagcgag ctcgatatca aattacgccc cgccctgcca ctcatcgcag   12360
tactgttgta attcattaag cattctgccg acatggaagc catcacaaac ggcatgatga   12420
acctgaatcg ccagcggcat cagcaccttg tcgccttgcg tataatattt gcccatggtg   12480
aaaacggggg cgaagaagtt gtccatattg gccacgttta aatcaaaact ggtgaaactc   12540
acccagggat tggctgagac gaaaaacata ttctcaataa acccctttagg gaaataggcc   12600 aggttttcac cgtaacacgc cacatcttgc gaatatatgt gtagaaactg ccggaaatcg   12660
tcgtggtatt cactccagag cgatgaaaac gtttcagttt gctcatggaa aacggtgtaa   12720
caagggtgaa cactatccca tatcaccagc tcaccgtctt tcattgccat acgaaattcc   12780
ggatgagcat tcatcaggcg ggcaagaatg tgaataaagg ccggataaaa cttgtgctta   12840
tttttcttta cggtctttaa aaaggccgta atatccagct gaacggtctg gttataggta   12900
cattgagcaa ctgactgaaa tgcctcaaaa tgttctttac gatgccattg ggatatatca   12960
acggtggtat atccagtgat ttttttctcc attttagctt ccttagctcc tgaaaatctc   13020
gataactcaa aaaatacgcc cggtagtgat cttatttcat tatggtgaaa gttggaacct   13080
cttacgtgcc gatcaacgtc tcattttcgc cagatatc                          13118
```

<210> SEQ ID NO 12
<211> LENGTH: 12594
<212> TYPE: DNA
<213> ORGANISM: Artificial Sequence
<220> FEATURE:
<223> OTHER INFORMATION: pBbA5c-MevT(co)-T1-MBI(co) plasmid vector

<400> SEQUENCE: 12

| | | | | | |
|---|---|---|---|---|---|
| gacgtcggtg | cctaatgagt | gagctaactt | acattaattg | cgttgcgctc | actgcccgct | 60 |
| ttccagtcgg | gaaacctgtc | gtgccagctg | cattaatgaa | tcggccaacg | cgcggggaga | 120 |
| ggcggtttgc | gtattgggcg | ccagggtggt | ttttcttttc | accagtgaga | cgggcaacag | 180 |
| ctgattgccc | ttcaccgcct | ggccctgaga | gagttgcagc | aagcggtcca | cgctggtttg | 240 |
| ccccagcagg | cgaaaatcct | gtttgatggt | ggttaacggc | gggatataac | atgagctgtc | 300 |
| tcggtatcg | tcgtatccca | ctaccgagat | gtccgcacca | acgcgcagcc | cggactcggt | 360 |
| aatggcgcgc | attgcgccca | gcgccatctg | atcgttggca | accagcatcg | cagtgggaac | 420 |
| gatgccctca | ttcagcattt | gcatggtttg | ttgaaaaccg | gacatggcac | tccagtcgcc | 480 |
| ttcccgttcc | gctatcggct | gaatttgatt | gcgagtgaga | tatttatgcc | agccagccag | 540 |
| acgcagacgc | gccgagacag | aacttaatgg | gcccgctaac | agcgcgattt | gctggtgacc | 600 |
| caatgcgacc | agatgctcca | cgcccagtcg | cgtaccgtct | tcatgggaga | aaataatact | 660 |
| gttgatgggt | gtctggtcag | agacatcaag | aaataacgcc | ggaacattag | tgcaggcagc | 720 |
| ttccacagca | atggcatcct | ggtcatccag | cggatagtta | atgatcagcc | cactgacgcg | 780 |
| ttgcgcgaga | agattgtgca | ccgccgcttt | acaggcttcg | acgccgcttc | gttctaccat | 840 |
| cgacaccacc | acgctggcac | ccagttgatc | ggcgcgagat | ttaatcgccg | cgacaatttg | 900 |
| cgacggcgcg | tgcagggcca | gactggaggt | ggcaacgcca | atcagcaacg | actgtttgcc | 960 |
| cgccagttgt | tgtgccacgc | ggttgggaat | gtaattcagc | tccgccatcg | ccgcttccac | 1020 |
| tttttcccgc | gttttcgcag | aaacgtggct | ggcctggttc | accacgcggg | aaacggtctg | 1080 |
| ataagagaca | ccggcatact | ctgcgacatc | gtataacgtt | actggtttca | cattcaccac | 1140 |
| cctgaattga | ctctcttccg | ggcgctatca | tgccataccg | cgaaaggttt | tgcgccattc | 1200 |
| gatggtgtcc | gggatctcga | cgctctccct | tatgcgactc | ctgcattagg | aagcagccca | 1260 |
| gtagtaggtt | gaggccgttg | agcaccgccg | ccgcaaggaa | tggtgcatgc | aaggagatgg | 1320 |
| cgcccaacag | tccccggcc | acggggcctg | ccaccatacc | cacgccgaaa | caagcgctca | 1380 |
| tgagcccgaa | gtggcgagcc | cgatcttccc | catcggtgat | gtcggcgata | taggcgccag | 1440 |
| caaccgcacc | tgtggcgccg | gtgatgccgg | ccacgatgcg | tccggcgtag | aggatcgaga | 1500 |
| tcgtttaggc | accccaggct | ttacacttta | tgcttccggc | tcgtataatg | tgtggaattg | 1560 |
| tgagcggata | acaatttcag | aattcaaaag | atctaaagga | ggccatcctg | ccatgaagaa | 1620 |
| actgtgtgat | tgtttctgcg | gtccgcacgg | cgatcggcag | ctttaacggc | tctttagcga | 1680 |
| gcacctctgc | aatcgatctg | ggtgcgacgg | tcattaaggc | cgccattgaa | cgcgccaaaa | 1740 |
| tcgacagcca | gcacgttgat | gaggtgatca | tgggcaatgt | gttacaagcc | ggcctgggtc | 1800 |
| aaaacccagc | gcgtcaagca | ctgttaaaat | ctggtctggc | cgagaccgtg | tgtgccttca | 1860 |
| ccgtcaataa | ggtttgcggc | tctggcctga | agagcgtggc | cctggcagca | caagcgattc | 1920 |
| aagccggtca | ggcacaaagc | atcgttgcgg | gtggcatgga | gaacatgtct | ctggcgccgt | 1980 |
| acttattaga | tgccaaagcc | cgcagcggtt | atcgcctggg | cgatggtcag | gtgtacgacg | 2040 |
| tcatcttacg | cgatggctta | atgtgcgcga | cccacggtta | ccacatgggt | attacggccg | 2100 |
| aaaacgtggc | gaaagaatac | ggcattacgc | gcgagatgca | ggatgaatta | gcactgcact | 2160 |
| ctcagcgcaa | agcagcagcc | gcgatcgagt | ctggtgcgtt | tacggcggaa | atcgtgccag | 2220 |

```
ttaacgtggt cacgcgcaag aagacgttcg ttttcagcca ggacgagttc ccgaaggcaa   2280
acagcaccgc ggaggcctta ggtgccttac gcccagcctt tgacaaagcg ggcacggtca   2340
ccgccggtaa tgcgagcggc atcaatgatg gtgcagcggc actggtcatc atggaagaga   2400
gcgccgcatt agcagcgggt ctgacccat tagcgcgcat taaatcttat gccagcggcg    2460
gcgtcccacc agccctgatg ggcatgggtc cggtcccagc cacgcaaaaa gccctgcaat   2520
tagcgggcct gcaactggcc gacattgatc tgatcgaggc gaacgaggcg tttgcagcgc   2580
agttcctggc ggtgggtaag aatctgggct tcgacagcga gaaagtcaat gtgaacggtg   2640
gcgcgattgc gttaggccat ccgattggtg caagcggcgc acgcatctta gtgacgttac   2700
tgcacgccat gcaggcacgc gacaagacct taggcctggc gaccttatgt attggtggcg   2760
gtcaaggtat cgccatggtg atcgaacgcc tgaactgatg aaggaggaaa gcaaaatgaa   2820
actgagcacc aagctgtgct ggtgtggcat caagggtcgc ctgcgcccac aaaagcagca   2880
acagctgcac aacacgaacc tgcaaatgac cgagctgaaa aagcagaaga cggccgagca   2940
aaagacccgc ccgcagaacg ttggcatcaa gggcatccag atttatatcc cgacgcagtg   3000
tgtcaaccaa tctgagctgg agaaattcga tggcgtcagc cagggtaagt acaccatcgg   3060
cctgggccag accaacatga gcttcgtgaa cgaccgtgag gacatctatt ctatgagcct   3120
gacggtgctg tctaagctga tcaagagcta caacatcgac acgaataaga tcggtcgtct   3180
ggaggtgggt acggagacgc tgattgacaa gagcaaaagc gtgaagtctg tcttaatgca   3240
gctgttcggc gagaacacgg atgtcgaggg tatcgacacc ctgaacgcgt gttacggcgg   3300
caccaacgca ctgttcaata gcctgaactg gattgagagc aacgcctggg atggccgcga   3360
tgcgatcgtc gtgtgcggcg atatcgccat ctatgacaag ggtgcggcac gtccgaccgg   3420
cggtgcaggc accgttgcga tgtggattgg cccggacgca ccaattgtct tcgattctgt   3480
ccgcgcgtct tacatggagc acgcctacga cttttacaag ccggacttca cgagcgaata   3540
cccgtacgtg gacggccact ctctctgac ctgctatgtg aaggcgctgg accaggttta   3600
taagtcttat agcaaaaagg cgatttctaa gggcctggtc agcgacccgg caggcagcga   3660
cgccctgaac gtgctgaagt atttcgacta caacgtgttc catgtcccga cctgcaaatt   3720
agtgaccaaa tcttatggcc gcctgttata taatgatttc cgtgccaacc cgcagctgtt   3780
cccggaggtt gacgccgagc tggcgacgcg tgattacgac gagagcctga ccgacaagaa   3840
catcgagaag accttcgtca acgtcgcgaa gccgttccac aaagagcgtg tggcccaaag   3900
cctgatcgtc ccgaccaaca cgggcaacat gtataccgcg tctgtctacg cggcattcgc   3960
gagcctgctg aattacgtcg gttctgacga cctgcagggc aagcgcgttg gcctgttcag   4020
ctacggtagc ggcttagcgg ccagcctgta tagctgcaaa attgtcggcg acgtccagca   4080
catcatcaag gagctggaca tcaccaacaa gctggcgaag cgcatcaccg agacgccgaa   4140
agattacgag gcagcgatcg agttacgcga gaatgcgcat ctgaagaaga acttcaagcc   4200
gcaaggtagc atcgagcacc tgcagagcgg cgtctactac ctgacgaaca ttgacgacaa   4260
gttccgccgt tcttatgacg tcaaaaagta actagtagga ggaaaacatc atggtgctga   4320
cgaacaaaac cgtcattagc ggcagcaagg tgaagtctct gagcagcgcc caaagctcta   4380
gcagcggccc gtctagcagc agcgaggagg acgacagccg tgacattgag tctctggaca   4440
agaagatccg cccgctggag gagttagagg ccctgctgag cagcggcaac accaagcagc   4500
tgaagaacaa ggaagttgca gcgctggtga tccacggtaa gctgccactg tatgcgctgg   4560
aaaagaaact gggcgatacg acgcgtgcgg tcgcggtgcg tcgcaaagcc ttaagcatct   4620
```

```
tagcggaggc cccggtgtta gccagcgacc gcctgccgta caagaactac gactacgacc    4680
gcgtgtttgg cgcgtgctgc gagaatgtca ttggctacat gccgttaccg gttggtgtga    4740
tcggcccgct ggtcattgat ggcacgagct atcacattcc aatggcgacc acggaaggtt    4800
gcttagtcgc cagcgccatg cgtggctgta aggcgattaa cgccggcggt ggcgcgacga    4860
ccgtgttaac caaggatggt atgacgcgcg gtccggtcgt ccgcttccca acgctgaagc    4920
gcagcggcgc gtgtaagatt tggctggatt ctgaggaggg ccaaaacgcg atcaagaaag    4980
ccttcaactc tacgagccgt ttcgcgcgtt tacagcatat ccagacctgc ctggccggcg    5040
acctgctgtt catgcgcttc cgcaccacca cgggcgatgc gatgggcatg aacatgatca    5100
gcaagggcgt cgaatatagc ctgaaacaaa tggtggaaga atatggctgg gaggacatgg    5160
aggttgtctc tgtgagcggc aactattgca ccgacaagaa gccggcagcc attaactgga    5220
ttgagggtcg cggcaaaagc gtcgtggcag aagcgaccat cccaggcgac gtggtccgta    5280
aggttctgaa gagcgacgtc agcgcccctgg ttgagttaaa tatcgcgaaa aacctggtcg    5340
gcagcgcgat ggcgggcagc gtgggtggct ttaacgcaca tgcagcgaat ctggttacgg    5400
cggttttctt agccttaggt caggacccag cccaaaatgt cgagagcagc aactgcatta    5460
ccttaatgaa agaggttgac ggtgacctgc gcatcagcgt ttctatgccg tctatcgagg    5520
tcggcacgat cggcggcggc accgttttag aaccgcaagg tgcgatgctg gatctgctgg    5580
gcgtgcgcgg cccacatgca acggcccag gcaccaatgc ccgccaactg gcccgtatcg    5640
tggcctgcgc ggttctggcg ggtgagctga gcctgtgcgc cgcattagcc gcgggccatt    5700
tagttcaatc tcacatgacc cacaaccgca agccggcaga accaaccaag ccaaataacc    5760
tggacgcaac cgacattaac cgtctgaagg atggcagcgt cacgtgcatt aaaagctgag    5820
gatctccagg catcaaataa aacgaaaggc tcagtcgaaa gactgggcct ttcgttttat    5880
ctgttgtttg tcggtgaacg ctctctacta gagtcacact ggctcacctt cgggtgggcc    5940
tttctgcgtt tatagcgaat tgatctggtt tgacagctta tcatcgactg cacggtgcac    6000
caatgcttct ggcgtcaggc agccatcgga agctgtggta tggctgtgca ggtcgtaaat    6060
cactgcataa ttcgtgtcgc tcaaggcgca ctcccgttct ggataatgtt ttttgcgccg    6120
acatcataac ggttctggca atattctga aatgagctgt tgacaattaa tcatccggct    6180
cgtataatgt gtggaattgt gagcggataa caatttcagg atctaggagg aaataaccat    6240
gtctctgcca ttcctgacgt ctgcgccagg taaggtgatc atcttcggcg agcactctgc    6300
ggtgtacaat aagccggccg tcgccgcctc tgtgtctgcg ttacgcacct acctgctgat    6360
cagcgaatct tctgcaccgg acacgatcga gctggacttt ccggacatca gcttcaacca    6420
caagtggagc atcaacgact tcaacgcgat cacggaggac caggtgaaca gccaaaagct    6480
ggccaaagcc cagcaagcaa ccgacggtct gtctcaggag ctggtgtctc tgctggaccc    6540
gctgttagcg cagttaagcg agagcttcca ttaccacgcc gcgttctgct tcctgtacat    6600
gttcgtttgc ctgtgcccgc acgcaaagaa catcaagttc agcctgaaga gcacgctgcc    6660
gattggcgca ggcttaggct ctagcgcatc tatcagcgtg agcctggcgc tggcgatggc    6720
ctatctgggt ggcctgattg cagcaacga cctggagaaa ctgagcgaaa cgacaagca    6780 catcgtgaac cagtgggcct ttatcggcga gaagtgcatt catggcaccc cgagcggcat    6840
tgacaacgca gttgccacgt atggcaacgc cctgctgttc gagaaagaca gccacaacgg    6900
cacgatcaac acgaacaact tcaagttcct ggacgacttc ccggcgatcc cgatgattct    6960
```

-continued

```
gacctacacc cgtatcccac gcagcaccaa ggatttagtc gcccgcgtgc gtgttttagt    7020
caccgaaaag ttcccggagg tgatgaagcc gatcctggac gcgatgggcg agtgcgcgct    7080
gcagggtctg gagatcatga ccaagctgag caagtgcaag ggcaccgacg atgaggcggt    7140
ggagaccaac aatgagctgt acgagcagct gctggagctg atccgtatca atcacggcct    7200
gctggtctct atcggtgtgt ctcacccggg cctggaactg atcaaaaacc tgagcgacga    7260
cctgcgcatt ggctctacga aattaacggg tgcaggtggc ggtggctgct ctttaacgct    7320
gctgcgccgt gacattacgc aggagcaaat cgacagcttc aagaagaagc tgcaggacga    7380
cttcagctac gagacgttcg agacggacct gggcggcacg ggctgttgcc tgctgagcgc    7440
caaaaatctg aacaaggacc tgaagatcaa aagcctggtg ttccagctgt cgaaaacaa    7500 gacgaccacg aagcagcaga tcgacgacct gttactgccg ggtaacacca atctgccgtg    7560
gacgtcttaa ggatctagga gggagatcat atgagcgaat acgtgcatt cagcgcgcca    7620 ggtaaggcac tgctggccgg tggctacctg gtgttagaca ccaagtacga ggcgttcgtc    7680
gtcggcttat ctgcccgtat gcatgcagtt gcccacccgt atggtagcct gcagggctct    7740
gacaagttcg aagtgcgtgt gaagagcaag cagttcaagg acggcgagtg gctgtaccac    7800
attagcccaa agagcggctt catcccggtt agcattggtg gcagcaagaa cccatttatc    7860
gagaaggtca ttgccaacgt cttcagctac ttcaagccga atatggacga ttactgcaac    7920
cgcaacctgt tcgtcatcga catttcagc gacgacgcgc accacagcca agaggactct    7980
gttacggagc atcgtggtaa ccgccgcctg agcttccaca gccatcgcat tgaggaggtg    8040
ccgaagacgg gtctgggttc tagcgccggt ttagttaccg tcttaacgac ggcgttagcg    8100
agcttcttcg tgagcgacct ggagaacaac gtggacaagt accgcgaagt gattcataac    8160
ctggcgcagg tggcacattg tcaggcccaa ggtaagattg gctctggttt tgatgtggca    8220
gcggccgcct atggctctat ccgctatcgc cgctttccgc cggccctgat cagcaatctg    8280
ccggacatcg gctctgcgac gtatggtagc aaactggcgc atctggtgga cgaagaagac    8340
tggaacatca ccattaagtc taatcacctg ccgagcggct aacgttatg gatgggcgat     8400 atcaagaacg gcagcgaaac ggttaagctg gtgcagaaag tgaaaaactg gtacgacagc    8460
cacatgccgg aaagcctgaa gatttacacg gagctggacc acgccaatag ccgtttcatg    8520
gatggtctga gcaagctgga ccgcctgcac gaaacccacg acgactacag cgaccaaatc    8580
ttcgagagcc tggagcgcaa tgactgcacc tgccagaagt acccggagat cacggaggtc    8640
cgcgatgccg tggcaacgat cgccgtagcc ttccgcaaaa ttacgaagga gagcggcgcg    8700
gatatcgaac caccggtcca gacgtctctg ctggacgact gtcaaacctt aaagggcgtg    8760
ttaacgtgcc tgattccggg cgcgggtggt tacgacgcca ttgccgtcat cacgaaacag    8820
gacgtcgatc tgcgcgcaca aacggccaac gacaaacgtt tcagcaaagt ccaatggctg    8880
gatgttacgc aggccgactg gggtgttcgc aaggagaagg acccggaaac gtatctggat    8940
aagtgaggat ctaggaggat tatgagatga ccgtttacac agcatccgtt accgcacccg    9000
tcaacatcgc aaccccttaag tattggggga aaagggacac gaagttgaat ctgcccacca    9060
attcgtccat atcagtgact ttatcgcaag atgacctcag aacgttgacc tctgcggcta    9120
ctgcacctga gtttgaacgc gacactttgt ggttaaatgg agaaccacac agcatcgaca    9180
atgaaagaac tcaaaattgt ctgcgcgacc tacgccaatt aagaaaggaa atggaatcga    9240
aggacgcctc attgcccaca ttatctcaat ggaaactcca cattgtctcc gaaaataact    9300
ttcctacagc agctggttta gcttcctccg ctgctggctt tgctgcattg gtctctgcaa    9360
```

| | |
|---|---|
| ttgctaagtt ataccaatta ccacagtcaa cttcagaaat atctagaata gcaagaaagg | 9420 |
| ggtctggttc agcttgtaga tcgttgtttg gcggatacgt ggcctgggaa atgggaaaag | 9480 |
| ctgaagatgg tcatgattcc atggcagtac aaatcgcaga cagctctgac tggcctcaga | 9540 |
| tgaaagcttg tgtcctagtt gtcagcgata ttaaaaagga tgtgagttcc actcagggta | 9600 |
| tgcaattgac cgtggcaacc tccgaactat ttaaagaaag aattgaacat gtcgtaccaa | 9660 |
| agagatttga agtcatgcgt aaagccattg ttgaaaaaga tttcgccacc tttgcaaagg | 9720 |
| aaacaatgat ggattccaac tctttccatg ccacatgttt ggactctttc cctccaatat | 9780 |
| tctacatgaa tgcacttcc aagcgtatca tcagttggtg ccacaccatt aatcagtttt | 9840 |
| acggagaaac aatcgttgca tacacgtttg atgcaggtcc aaatgctgtg ttgtactact | 9900 |
| tagctgaaaa tgagtcgaaa ctcttttgcat ttatctataa attgtttggc tctgttcctg | 9960 |
| gatgggacaa gaaatttact actgagcagc ttgaggcttt caaccatcaa tttgaatcat | 10020 |
| ctaactttac tgcacgtgaa ttggatcttg agttgcaaaa ggatgttgcc agagtgattt | 10080 |
| taactcaagt cggttcaggc ccacaagaaa caaacgaatc tttgattgac gcaaagactg | 10140 |
| gtctaccaaa ggaataagga tctaggaggt aatgataatg caaacggaac acgtcatttt | 10200 |
| attgaatgca cagggagttc ccacgggtac gctggaaaag tatgccgcac acacggcaga | 10260 |
| cacccgctta catctcgcgt tctccagttg gctgtttaat gccaaaggac aattattagt | 10320 |
| tacccgccgc gcactgagca aaaaagcatg gcctggcgtg tggactaact cggtttgtgg | 10380 |
| gcacccacaa ctgggagaaa gcaacgaaga cgcagtgatc cgccgttgcc gttatgagct | 10440 |
| tggcgtggaa attacgcctc ctgaatctat ctatcctgac tttcgctacc gcgccaccga | 10500 |
| tccgagtggc attgtggaaa atgaagtgtg tccggtattt gccgcacgca ccactagtgc | 10560 |
| gttacagatc aatgatgatg aagtgatgga ttatcaatgg tgtgatttag cagatgtatt | 10620 |
| acacggtatt gatgccacgc cgtgggcgtt cagtccgtgg atggtgatgc aggcgacaaa | 10680 |
| tcgcgaagcc agaaaacgat tatctgcatt tacccagctt aaataaggat ccaaactcga | 10740 |
| gtaaggatct ccaggcatca aataaaacga aaggctcagt cgaaagactg gcctttcgt | 10800 |
| tttatctgtt gtttgtcggt gaacgctctc tactagagtc acactggctc accttcgggt | 10860 |
| gggcctttct gcgtttatac ctagggatat attccgcttc ctcgctcact gactcgctac | 10920 |
| gctcggtcgt tcgactgcgg cgagcggaaa tggcttacga acggggcgga gatttcctgg | 10980 |
| aagatgccag gaagatactt aacagggaag tgagagggcc gcggcaaagc cgttttttcca | 11040 |
| taggctccgc ccccctgaca agcatcacga aatctgacgc tcaaatcagt ggtggcgaaa | 11100 |
| cccgacagga ctataaagat accaggcgtt tccccctggc ggctccctcg tgcgctctcc | 11160 |
| tgttcctgcc tttcggttta ccggtgtcat tccgctgtta tggccgcgtt tgtctcattc | 11220 |
| cacgcctgac actcagttcc gggtaggcag ttcgctccaa gctggactgt atgcacgaac | 11280 |
| cccccgttca gtccgaccgc tgcgccttat ccggtaacta tcgtcttgag tccaacccgg | 11340 |
| aaagacatgc aaaagcacca ctggcagcag ccactggtaa ttgatttaga ggagttagtc | 11400 |
| ttgaagtcat gcgccggtta aggctaaact gaaaggacaa gttttggtga ctgcgctcct | 11460 |
| ccaagccagt tacctcggtt caagagttg gtagctcaga gaaccttcga aaaccgccc | 11520 |
| tgcaaggcgg ttttttcgtt ttcagagcaa gagattacgc gcagaccaaa acgatctcaa | 11580 |
| gaagatcatc ttattaatca gataaaatat ttctagattt cagtgcaatt tatctcttca | 11640 |
| aatgtagcac ctgaagtcag ccccatacga tataagttgt tactagtgct tggattctca | 11700 |

| | |
|---|---|
| ccaataaaaa acgcccggcg gcaaccgagc gttctgaaca atccagatg gagttctgag | 11760 |
| gtcattactg gatctatcaa caggagtcca agcgagctcg atatcaaatt acgccccgcc | 11820 |
| ctgccactca tcgcagtact gttgtaattc attaagcatt ctgccgacat ggaagccatc | 11880 |
| acaaacggca tgatgaacct gaatcgccag cggcatcagc accttgtcgc cttgcgtata | 11940 |
| atatttgccc atggtgaaaa cggggggcgaa gaagttgtcc atattggcca cgtttaaatc | 12000 |
| aaaactggtg aaactcaccc agggattggc tgagacgaaa aacatattct caataaaccc | 12060 |
| tttagggaaa taggccaggt tttcaccgta acacgccaca tcttgcgaat atatgtgtag | 12120 |
| aaactgccgg aaatcgtcgt ggtattcact ccagagcgat gaaaacgttt cagtttgctc | 12180 |
| atggaaaacg gtgtaacaag ggtgaacact atcccatatc accagctcac cgtctttcat | 12240 |
| tgccatacga aattccggat gagcattcat caggcgggca agaatgtgaa taaaggccgg | 12300 |
| ataaaacttg tgcttatttt tctttacggt cttttaaaaag gccgtaatat ccagctgaac | 12360 |
| ggtctggtta taggtacatt gagcaactga ctgaaatgcc tcaaaatgtt ctttacgatg | 12420 |
| ccattgggat atatcaacgg tggtatatcc agtgattttt ttctccattt tagcttcctt | 12480 |
| agctcctgaa aatctcgata actcaaaaaa tacgcccggt agtgatctta tttcattatg | 12540 |
| gtgaaagttg gaacctctta cgtgccgatc aacgtctcat tttcgccaga tatc | 12594 |

<210> SEQ ID NO 13
<211> LENGTH: 13517
<212> TYPE: DNA
<213> ORGANISM: Artificial Sequence
<220> FEATURE:
<223> OTHER INFORMATION: pBbA5c-MevT(co)-T1-MBIG(co) plasmid vector

<400> SEQUENCE: 13

| | |
|---|---|
| gacgtcggtg cctaatgagt gagctaactt acattaattg cgttgcgctc actgcccgct | 60 |
| ttccagtcgg gaaacctgtc gtgccagctg cattaatgaa tcggccaacg cgcggggaga | 120 |
| ggcggtttgc gtattgggcg ccagggtggt ttttcttttc accagtgaga cgggcaacag | 180 |
| ctgattgccc ttcaccgcct ggccctgaga gagttgcagc aagcggtcca cgctggtttg | 240 |
| ccccagcagg cgaaaatcct gtttgatggt ggttaacggc gggatataac atgagctgtc | 300 |
| ttcggtatcg tcgtatccca ctaccgagat gtccgcacca acgcgcagcc cggactcggt | 360 |
| aatggcgcgc attgcgccca cgcgcatctg atcgttggca accagcatcg cagtgggaac | 420 |
| gatgccctca ttcagcattt gcatggtttg ttgaaaaccg gacatggcac tccagtcgcc | 480 |
| ttcccgttcc gctatcggct gaatttgatt gcgagtgaga tatttatgcc agccagccag | 540 |
| acgcagacgc gccgagacag aacttaatgg gcccgctaac agcgcgattt gctggtgacc | 600 |
| caatgcgacc agatgctcca cgcccagtcg cgtaccgtct tcatgggaga aaataatact | 660 |
| gttgatgggt gtctggtcag agacatcaag aaataacgcc ggaacattag tgcaggcagc | 720 |
| ttccacagca atggcatcct ggtcatccag cggatagtta atgatcagcc cactgacgcg | 780 |
| ttgcgcgaga agattgtgca ccgccgcttt acaggcttcg acgccgcttc gttctaccat | 840 |
| cgacaccacc acgctggcac ccagttgatc ggcgcgagat ttaatcgccg cgacaatttg | 900 |
| cgacggcgcg tgcagggcca gactggaggt ggcaacgcca atcagcaacg actgtttgcc | 960 |
| cgccagttgt tgtgccacgc ggttgggaat gtaattcagc tccgccatcg ccgcttccac | 1020 |
| tttttcccgc gttttcgcag aaacgtggct ggcctggttc accacgcggg aaacggtctg | 1080 |
| ataagagaca ccggcatact ctgcgacatc gtataacgtt actggtttca cattcaccac | 1140 |
| cctgaattga ctctcttccg ggcgctatca tgccataccg cgaaaggttt tgcgccattc | 1200 |

```
gatggtgtcc gggatctcga cgctctccct tatgcgactc ctgcattagg aagcagccca   1260
gtagtaggtt gaggccgttg agcaccgccg ccgcaaggaa tggtgcatgc aaggagatgg   1320
cgcccaacag tcccccggcc acggggcctg ccaccatacc cacgccgaaa caagcgctca   1380
tgagcccgaa gtggcgagcc cgatcttccc catcggtgat gtcggcgata taggcgccag   1440
caaccgcacc tgtggcgccg gtgatgccgg ccacgatgcg tccggcgtag aggatcgaga   1500
tcgtttaggc accccaggct ttacacttta tgcttccggc tcgtataatg tgtggaattg   1560
tgagcggata acaatttcag aattcaaaag atctaaagga ggccatcctg gccatgaaga   1620
actgtgtgat tgtttctgcg gtccgcacgg cgatcggcag cttaacggc tctttagcga    1680 gcacctctgc aatcgatctg ggtgcgacgg tcattaaggc cgccattgaa cgcgccaaaa   1740
tcgacagcca gcacgttgat gaggtgatca tgggcaatgt gttacaagcc ggcctgggtc   1800
aaaacccagc gcgtcaagca ctgttaaaat ctggtctggc cgagaccgtg tgtggcttca   1860
ccgtcaataa ggtttgcggc tctggcctga agagcgtggc cctggcagca caagcgattc   1920
aagccggtca ggcacaaagc atcgttgcgg gtggcatgga aacatgtct ctggcgccgt    1980 acttattaga tgccaaagcc cgcagcggtt atcgcctggg cgatggtcag gtgtacgacg   2040
tcatcttacg cgatggctta atgtgcgcga cccacggtta ccacatgggt attacggccg   2100
aaaacgtggc gaaagaatac ggcattacgc gcgagatgca ggatgaatta gcactgcact   2160
ctcagcgcaa agcagcagcc gcgatcgagt ctggtgcgtt tacggcggaa atcgtgccag   2220
ttaacgtggt cacgcgcaag aagacgttcg ttttcagcca ggacgagttc ccgaaggcaa   2280
acagcaccgc ggaggcctta ggtgccttac gcccagcctt tgacaaagcg gcacggtca    2340 ccgccggtaa tgcgagcggc atcaatgatg gtgcagcggc actggtcatc atggaagaga   2400
gcgccgcatt agcagcgggt ctgaccccat tagcgcgcat taaatcttat gccagcggcg   2460
gcgtcccacc agccctgatg ggcatgggtc cggtcccagc cacgcaaaaa gccctgcaat   2520
tagcgggcct gcaactggcc gacattgatc tgatcgaggc gaacgaggcg tttgcagcgc   2580
agttcctggc ggtgggtaag aatctggct tcgacagcga aaagtcaat gtgaacggtg     2640 gcgcgattgc gttaggccat ccgattggtg caagcggcgc acgcatctta gtgacgttac   2700
tgcacgccat gcaggcacgc gacaagacct taggcctggc gaccttatgt attggtggcg   2760
gtcaaggtat cgccatggtg atcgaacgcc tgaactgatg aaggaggaaa gcaaaatgaa   2820
actgagcacc aagctgtgct ggtgtggcat caagggtcgc ctgcgcccac aaaagcagca   2880
acagctgcac aacacgaacc tgcaaatgac cgagctgaaa aagcagaaga cggccgagca   2940
aaagacccgc ccgcagaacg ttggcatcaa gggcatccag atttatatcc gacgcagtg    3000 tgtcaaccaa tctgagctgg agaaattcga tggcgtcagc cagggtaagt acaccatcgg   3060
cctgggccag accaacatga gcttcgtgaa cgaccgtgag gacatctatt ctatgagcct   3120
gacggtgctg tctaagctga tcaagagcta caacatcgac acgaataaga tcggtcgtct   3180
ggaggtgggt acggagacgc tgattgacaa gagcaaaagc gtgaagtctg tcttaatgca   3240
gctgttcggc gagaacacgg atgtcgaggg tatcgacacc ctgaacgcgt gttacggcgg   3300
caccaacgca ctgttcaata gcctgaactg gattgagagc aacgcctggg atggccgcga   3360
tgcgatcgtc gtgtgcggcg atatcgccat ctatgacaag ggtgcggcac gtccgaccgg   3420
cggtgcaggc accgttgcga tgtggattgg cccggacgca ccaattgtct tcgattctgt   3480
ccgcgcgtct tacatggagc acgcctacga cttttacaag ccggacttca cgagcgaata   3540
```

```
cccgtacgtg gacggccact tctctctgac ctgctatgtg aaggcgctgg accaggttta   3600
taagtcttat agcaaaaagg cgatttctaa gggcctggtc agcgacccgg caggcagcga   3660
cgccctgaac gtgctgaagt atttcgacta caacgtgttc catgtcccga cctgcaaatt   3720
agtgaccaaa tcttatggcc gcctgttata taatgatttc cgtgccaacc cgcagctgtt   3780
cccggaggtt gacgccgagc tggcgacgcg tgattacgac gagagcctga ccgacaagaa   3840
catcgagaag accttcgtca acgtcgcgaa gccgttccac aaagagcgtg tgcccaaag   3900
cctgatcgtc ccgaccaaca cgggcaacat gtataccgcg tctgtctacg cggcattcgc   3960
gagcctgctg aattacgtcg gttctgacga cctgcagggc aagcgcgttg gcctgttcag   4020
ctacggtagc ggcttagcgg ccagcctgta tagctgcaaa attgtcggcg acgtccagca   4080
catcatcaag gagctggaca tcaccaacaa gctggcgaag cgcatcaccg agacgccgaa   4140
agattacgag gcagcgatcg agttacgcga gaatgcgcat ctgaagaaga acttcaagcc   4200
gcaaggtagc atcgagacac ctgcagagcgg cgtctactac ctgacgaaca ttgacgacaa   4260
gttccgccgt tcttatgacg tcaaaaagta actagtagga ggaaaacatc atggtgctga   4320
cgaacaaaac cgtcattagc ggcagcaagg tgaagtctct gagcagcgcc caaagctcta   4380
gcagcggccc gtctagcagc agcgaggagg acgacagccg tgacattgag tctctggaca   4440
agaagatccg cccgctggag gagttagagg ccctgctgag cagcggcaac accaagcagc   4500
tgaagaacaa ggaagttgca gcgctggtga tccacggtaa gctgccactg tatgcgctgg   4560
aaaagaaact gggcgatacg acgcgtgcgg tcgcggtgcg tcgcaaagcc ttaagcatct   4620
tagcggaggc cccggtgtta gccagcgacc gcctgccgta caagaactac gactacgacc   4680
gcgtgtttgg cgcgtgctgc gagaatgtca ttggctacat gccgttaccg gttggtgtga   4740
tcggcccgct ggtcattgat ggcacgagct atcacattcc aatggcgacc acggaaggtt   4800
gcttagtcgc cagcgccatg cgtggctgta aggcgattaa cgccggcggt ggcgcgacga   4860
ccgtgttaac caaggatggt atgacgcgcg gtccggtcgt ccgcttccca acgctgaagc   4920
gcagcggcgc gtgtaagatt tggctggatt ctgaggaggg ccaaaacgcg atcaagaaag   4980
ccttcaactc tacgagccgt ttcgcgcgtt tacagcatat ccagacctgc ctggccggcg   5040
acctgctgtt catgcgcttc cgcaccacca cgggcgatgc gatgggcatg aacatgatca   5100
gcaagggcgt cgaatatagc ctgaaacaaa tggtggaaga atatggctgg gaggacatgg   5160
aggttgtctc tgtgagcggc aactattgca ccgacaagaa gccggcagcc attaactgga   5220
ttgagggtcg cggcaaaagc gtcgtggcag aagcgaccat cccaggcgac gtggtccgta   5280
aggttctgaa gagcgacgtc agcgccctgg ttgagttaaa tatcgcgaaa aacctggtcg   5340
gcagcgcgat ggcgggcagc gtgggtggct ttaacgcaca tgcagcgaat ctggttacgg   5400
cggtttttctt agccttaggt caggacccag cccaaaatgt cgagagcagc aactgcatta   5460
ccttaatgaa agaggttgac ggtgacctgc gcatcagcgt ttctatgccg tctatcgagg   5520
tcggcacgat cggcggcggc accgtttag aaccgcaagg tgcgatgctg gatctgctgg   5580
gcgtgcgcgg cccacatgca acggcccag gcaccaatgc cgccaactg gcccgtatcg   5640
tggcctgcgc ggttctggcg ggtgagctga gcctgtgcgc cgcattagcc gcgggccatt   5700
tagttcaatc tcacatgacc cacaaccgca agccggcaga accaaccaag ccaaataacc   5760
tggacgcaac cgacattaac cgtctgaagg atgcagcgt cacgtgcatt aaaagctgag   5820
gatctccagg catcaaataa aacgaaaggc tcagtcgaaa gactgggcct ttcgttttat   5880
ctgttgtttg tcggtgaacg ctctctacta gagtcacact ggctcacctt cgggtgggcc   5940
```

```
tttctgcgtt tatagcgaat tgatctggtt tgacagctta tcatcgactg cacggtgcac   6000
caatgcttct ggcgtcaggc agccatcgga agctgtggta tggctgtgca ggtcgtaaat   6060
cactgcataa ttcgtgtcgc tcaaggcgca ctcccgttct ggataatgtt ttttgcgccg   6120
acatcataac ggttctggca atattctgaa atgagctgtt tgacaattaa tcatccggct   6180
cgtataatgt gtggaattgt gagcggataa caatttcagg atctaggagg aaataaccat   6240
gtctctgcca ttcctgacgt ctgcgccagg taaggtgatc atcttcggcg agcactctgc   6300
ggtgtacaat aagccggccg tcgccgcctc tgtgtctgcg ttacgcacct acctgctgat   6360
cagcgaatct tctgcaccgg acacgatcga gctggacttt ccggacatca gcttcaacca   6420
caagtggagc atcaacgact tcaacgcgat cacggaggac caggtgaaca gccaaaagct   6480
ggccaaagcc cagcaagcaa ccgacggtct gtctcaggag ctggtgtctc tgctggaccc   6540
gctgttagcg cagttaagcg agagcttcca ttaccacgcc gcgttctgct tcctgtacat   6600
gttcgtttgc ctgtgcccgc acgcaaagaa catcaagttc agcctgaaga gcacgctgcc   6660
gattggcgca ggcttaggct ctagcgcatc tatcagcgtg agcctggcgc tggcgatggc   6720
ctatctgggt ggcctgattg gcagcaacga cctggagaaa ctgagcgaaa cgacaagca   6780 catcgtgaac cagtgggcct ttatcggcga gaagtgcatt catggcaccc cgagcggcat   6840
tgacaacgca gttgccacgt atggcaacgc cctgctgttc gagaaagaca gccacaacgg   6900
cacgatcaac acgaacaact tcaagttcct ggacgacttc ccggcgatcc cgatgattct   6960
gacctacacc cgtatcccac gcagcaccaa ggatttagtc gcccgcgtgc gtgttttagt   7020
caccgaaaag ttcccggagg tgatgaagcc gatcctggac gcgatgggcg agtgcgcgct   7080
gcagggtctg gagatcatga ccaagctgag caagtgcaag ggcaccgacg atgaggcggt   7140
ggagaccaac aatgagctgt acgagcagct gctggagctg atccgtatca atcacggcct   7200
gctggtctct atcggtgtgt ctcacccggg cctggaactg atcaaaaacc tgagcgacga   7260
cctgcgcatt ggctctacga aattaacggg tgcaggtggc ggtggctgct ctttaacgct   7320
gctgcgccgt gacattacgc aggagcaaat cgacagcttc aagaagaagc tgcaggacga   7380
cttcagctac gagacgttcg agacggacct gggcggcacg ggctgttgcc tgctgagcgc   7440
caaaaatctg aacaaggacc tgaagatcaa aagcctggtg ttccagctgt cgaaaacaa   7500 gacgaccacg aagcagcaga tcgacgcct gttactgccg ggtaacacca atctgccgtg   7560
gacgtcttaa ggatctagga gggagatcat atgagcgaat tacgtgcatt cagcgcgcca   7620
ggtaaggcac tgctggccgg tggctacctg gtgttagaca ccaagtacga ggcgttcgtc   7680
gtcggcttat ctgcccgtat gcatgcagtt gcccacccgt atggtagcct gcagggctct   7740
gacaagttcg aagtgcgtgt gaagagcaag cagttcaagg acggcgagtg gctgtaccac   7800
attagcccaa agagcggctt catcccggtt agcattggtg gcagcaagaa cccatttatc   7860
gagaaggtca ttgccaacgt cttcagctac ttcaagccga atatggacga ttactgcaac   7920
cgcaacctgt tcgtcatcga cattttcagc gacgacgcgt accacagcca agaggactct   7980
gttacggagc atcgtggtaa ccgccgcctg agcttccaca gccatcgcat tgaggaggtg   8040
ccgaagacgg gtctgggttc tagcgccggt ttagttaccg tcttaacgac ggcgttagcg   8100
agcttcttcg tgagcgacct ggagaacaac gtggacaagt accgcgaagt gattcataac   8160
ctggcgcagg tggcacattg tcaggcccaa ggtaagattg gctctggttt tgatgtggca   8220
gcggccgcct atggctctat ccgctatcgc cgctttccgc cggccctgat cagcaatctg   8280
```

```
ccggacatcg gctctgcgac gtatggtagc aaactggcgc atctggtgga cgaagaagac    8340
tggaacatca ccattaagtc taatcacctg ccgagcggct taacgttatg gatgggcgat    8400
atcaagaacg gcagcgaaac ggttaagctg gtgcagaaag tgaaaaactg gtacgacagc    8460
cacatgccgg aaagcctgaa gatttacacg gagctggacc acgccaatag ccgtttcatg    8520
gatggtctga gcaagctgga ccgcctgcac gaaacccacg acgactacag cgaccaaatc    8580
ttcgagagcc tggagcgcaa tgactgcacc tgccagaagt acccgagat cacggaggtc     8640 cgcgatgccg tggcaacgat tcgccgtagc ttccgcaaaa ttacgaagga gagcggcgcg    8700
gatatcgaac caccggtcca gacgtctctg ctggacgact gtcaaacctt aaagggcgtg    8760
ttaacgtgcc tgattccggg cgcgggtggt tacgacgcca ttgccgtcat cacgaaacag    8820
gacgtcgatc tgcgcgcaca aacggccaac gacaaacgtt tcagcaaagt ccaatggctg    8880
gatgttacgc aggccgactg gggtgttcgc aaggagaagg acccggaaac gtatctggat    8940
aagtgaggat ctaggaggat tatgagatga ccgtttacac agcatccgtt accgcacccg    9000
tcaacatcgc aaaccttaag tattggggga aaagggcaca gaagttgaat ctgcccacca    9060
attcgtccat atcagtgact ttatcgcaag atgacctcag aacgttgacc tctgcggcta    9120
ctgcacctga gtttgaacgc gacactttgt ggttaaatgg agaaccacac agcatcgaca    9180
atgaaagaac tcaaaattgt ctgcgcgacc tacgccaatt aagaaaggaa atggaatcga    9240
aggacgcctc attgcccaca ttatctcaat ggaaactcca cattgtctcc gaaataact     9300 ttcctacagc agctggttta gcttcctccg ctgctggctt tgctgcattg gtctctgcaa    9360
ttgctaagtt ataccaatta ccacagtcaa cttcagaaat atctagaata gcaagaaagg    9420
ggtctggttc agcttgtaga tcgttgtttg gcggatacgt ggcctgggaa atgggaaaag    9480
ctgaagatgg tcatgattcc atggcagtac aaatcgcaga cagctctgac tggcctcaga    9540
tgaaagcttg tgtcctagtt gtcagcgata ttaaaaagga tgtgagttcc actcagggta    9600
tgcaattgac cgtggcaacc tccgaactat ttaaagaaag aattgaacat gtcgtaccaa    9660
agagatttga agtcatgcgt aaagccattg ttgaaaaaga tttcgccacc tttgcaaagg    9720
aaacaatgat ggattccaac tcttccatg ccacatgttt ggactctttc cctccaatat     9780
tctacatgaa tgacacttcc aagcgtatca tcagttggtg ccacaccatt aatcagtttt    9840
acggagaaac aatcgttgca tacacgtttg atgcaggtcc aaatgctgtg ttgtactact    9900
tagctgaaaa tgagtcgaaa ctctttgcat ttatctataa attgtttggc tctgttcctg    9960
gatgggacaa gaaatttact actgagcagc ttgaggcttt caaccatcaa tttgaatcat    10020
ctaactttac tgcacgtgaa ttggatcttg agttgcaaaa ggatgttgcc agagtgattt    10080
taactcaagt cggttcaggc ccacaagaaa caaacgaatc tttgattgac gcaaagactg    10140
gtctaccaaa ggaataagga tctaggaggt aatgataatg caaacggaac acgtcatttt    10200
attgaatgca cagggagttc ccacgggtac gctggaaaag tatgccgcac acacggcaga    10260 caccccgctta catctcgcgt tctccagttg gctgtttaat gccaaaggac aattattagt    10320
tacccgccgc gcactgagca aaaaagcatg gcctggcgtg tggactaact cggtttgtgg    10380
gcacccacaa ctgggagaaa gcaacgaaga cgcagtgatc cgccgttgcc gttatgagct    10440
tggcgtggaa attcgcctc ctgaatctat ctatcctgac tttcgctacc gcgccaccga     10500
tccgagtggc attgtggaaa atgaagtgtg tccggtattt gccgcacgca ccactagtgc    10560
gttacagatc aatgatgatg aagtgatgga ttatcaatgg tgtgatttag cagatgtatt    10620
acacggtatt gatgccacgc cgtgggcgtt cagtccgtgg atggtgatgc aggcgacaaa    10680
```

```
tcgcgaagcc agaaaacgat tatctgcatt tacccagctt aaataaggat cttttaagaa    10740
ggagatatac atatggtgga atttgatttt aacaaatata tggatagcaa agcgatgacc    10800
gtgaacgaag cgctgaacaa agcgattccg ctgcgctatc cgcagaaaat ttatgaaagc    10860
atgcgctata gcctgctggc gggcggcaaa cgcgtgcgcc cggtgctgtg cattgcggcg    10920
tgcgaactgg tgggcggcac cgaagaactg gcgattccga ccgcgtgcgc gattgaaatg    10980
attcatacca tgagcctgat gcatgatgat ctgccgtgca ttgataacga tgatctgcgc    11040
cgcggcaaac cgaccaacca taaaattttt ggcgaagata ccgcggtgac cgcgggcaac    11100
gcgctgcata gctatgcgtt tgaacatatt gcggtgagca ccagcaaaac cgtgggcgcg    11160
gatcgcattc tgcgcatggt gagcgaactg ggccgcgcga ccggcagcga aggcgtgatg    11220
ggcggccaga tggtggatat tgcgagcgaa ggcgatccga gcattgatct gcagaccctg    11280
gaatggattc atattcataa aaccgcgatg ctgctggaat gcagcgtggt gtgcggcgcg    11340
attattggcg gcgcgagcga aattgtgatt gaacgcgcgc gccgctatgc gcgctgcgtg    11400
ggcctgctgt ttcaggtggt ggatgatatt ctggatgtga ccaaaagcag cgatgaactg    11460
ggcaaaaccg cgggcaaaga tttaattagc gataaagcga cctatccgaa actgatgggc    11520
ctggaaaaag cgaaagaatt tagcgatgaa ctgctgaacc gcgcgaaagg cgaactgagc    11580
tgctttgatc cggtgaaagc ggcgccgctg ctgggcctgg cggattatgt ggcgtttcgc    11640
cagaactaag gatccaaact cgagtaagga tctccaggca tcaaataaaa cgaaaggctc    11700
agtcgaaaga ctgggccttt cgttttatct gttgtttgtc ggtgaacgct ctctactaga    11760
gtcacactgg ctcaccttcg ggtgggcctt tctgcgttta tacctaggga tatattccgc    11820
ttcctcgctc actgactcgc tacgctcggt cgttcgactg cggcgagcgg aaatggctta    11880
cgaacggggc ggagatttcc tggaagatgc caggaagata cttaacaggg aagtgagagg    11940
gccgcggcaa agccgttttt ccataggctc cgcccccctg acaagcatca cgaaatctga    12000
cgctcaaatc agtggtggcg aaacccgaca ggactataaa gataccaggc gtttccccct    12060
ggcggctccc tcgtgcgctc tcctgttcct gcctttcggt ttaccggtgt cattccgctg    12120
ttatggccgc gtttgtctca ttccacgcct gacactcagt tccgggtagg cagttcgctc    12180
caagctggac tgtatgcacg aaccccccgt tcagtccgac cgctgcgcct tatccggtaa    12240
ctatcgtctt gagtccaacc cggaaagaca tgcaaaagca ccactggcag cagccactgg    12300
taattgattt agaggagtta gtcttgaagt catgcgccgg ttaaggctaa actgaaagga    12360
caagttttgg tgactgcgct cctccaagcc agttacctcg gttcaaagag ttggtagctc    12420
agagaacctt cgaaaaaccg ccctgcaagg cggttttttc gttttcagag caagagatta    12480
cgcgcagacc aaaacgatct caagaagatc atcttattaa tcagataaaa tatttctaga    12540
tttcagtgca atttatctct tcaaatgtag cacctgaagt cagccccata cgatataagt    12600
tgttactagt gcttggattc tcaccaataa aaaacgcccg cggcaaccg agcgttctga    12660 acaaatccag atggagttct gaggtcatta ctggatctat caacaggagt ccaagcgagc    12720
tcgatatcaa attacgcccc gccctgccac tcatcgcagt actgttgtaa ttcattaagc    12780
attctgccga catggaagcc atcacaaacg gcatgatgaa cctgaatcgc cagcggcatc    12840
agcaccttgt cgccttgcgt ataatatttg cccatggtga aacgggggc gaagaagttg    12900 tccatattgg ccacgtttaa atcaaaactg gtgaaactca cccagggatt ggctgagacg    12960
aaaaacatat tctcaataaa ccctttaggg aaataggcca ggttttcacc gtaacacgcc    13020
```

-continued

```
acatcttgcg aatatatgtg tagaaactgc cggaaatcgt cgtggtattc actccagagc    13080
gatgaaaacg tttcagtttg ctcatggaaa acggtgtaac aagggtgaac actatcccat    13140
atcaccagct caccgtcttt cattgccata cgaaattccg gatgagcatt catcaggcgg    13200
gcaagaatgt gaataaaggc cggataaaac ttgtgcttat ttttctttac ggtctttaaa    13260
aaggccgtaa tatccagctg aacggtctgg ttataggtac attgagcaac tgactgaaat    13320
gcctcaaaat gttctttacg atgccattgg gatatatcaa cggtggtata tccagtgatt    13380 ttttctcca ttttagcttc cttagctcct gaaaatctcg ataactcaaa aaatacgccc    13440
ggtagtgatc ttatttcatt atggtgaaag ttggaacctc ttacgtgccg atcaacgtct    13500
cattttcgcc agatatc                                                  13517
```

<210> SEQ ID NO 14
<211> LENGTH: 5216
<212> TYPE: DNA
<213> ORGANISM: Artificial Sequence
<220> FEATURE:
<223> OTHER INFORMATION: pBbE1a-tMS(co.Qi) plasmid vector

<400> SEQUENCE: 14

```
gacgtcgaca ccatcgaatg gtgcaaaacc tttcgcggta tggcatgata gcgcccggaa      60
gagagtcaat tcagggtggt gaatgtgaaa ccagtaacgt tatacgatgt cgcagagtat     120
gccggtgtct cttatcagac cgtttcccgc gtggtgaacc aggccagcca cgtttctgcg     180
aaaacgcggg aaaaagtgga agcggcgatg cggagctga attacattcc caaccgcgtg     240
gcacaacaac tggcgggcaa acagtcgttg ctgattggcg ttgccacctc cagtctggcc     300
ctgcacgcgc cgtcgcaaat tgtcgcggcg attaaatctc gcgccgatca actgggtgcc     360
agcgtggtgg tgtcgatggt agaacgaagc ggcgtcgaag cctgtaaagc ggcggtgcac     420
aatcttctcg cgcaacgcgt cagtgggctg atcattaact atccgctgga tgaccaggat     480
gccattgctg tggaagctgc ctgcactaat gttccggcgt tatttcttga tgtctctgac     540
cagacaccca tcaacagtat tattttctcc catgaagacg gtacgcgact gggcgtggag     600
catctggtcg cattgggtca ccagcaaatc gcgctgttag cgggcccatt aagttctgtc     660
tcggcgcgtc tgcgtctggc tggctggcat aaatatctca ctcgcaatca aattcagccg     720
atagcggaac gggaaggcga ctggagtgcc atgtccggtt ttcaacaaac catgcaaatg     780
ctgaatgagg gcatcgttcc cactgcgatg ctggttgcca acgatcagat ggcgctgggc     840
gcaatgcgcg ccattaccga gtccgggctg cgcgttggtg cggatatctc ggtagtggga     900
tacgacgata ccgaagacag ctcatgttat atcccgccgt taaccaccat caaacaggat     960
tttcgcctgc tggggcaaac cagcgtggac cgcttgctgc aactctctca gggccaggcg    1020
gtgaagggca atcagctgtt gcccgtctca ctggtgaaaa gaaaaaccac cctggcgccc    1080
aatacgcaaa ccgcctctcc ccgcgcgttg gccgattcat taatgcagct ggcacgacag    1140
gtttcccgac tggaaagcgg gcagtgagcg caacgcaatt aatgtaagtt agcgcgaatt    1200
gatctggttt gacagcttat catcgactgc acggtgcacc aatgcttctg cgtcaggca     1260 gccatcggaa gctgtggtat ggctgtgcag gtcgtaaatc actgcataat tcgtgtcgct    1320
caaggcgcac tcccgttctg gataatgttt tttgcgccga catcataacg gttctggcaa    1380
atattctgaa atgagctgtt gacaattaat catccggctc gtataatgtg tggaattgtg    1440
agcggataac aatttcagaa ttcaaaagat cttttaagaa ggagatatac atatgcgtcg    1500
tagcgcaaat tatcagccga gcatttggaa tcatgattat attgaaagcc tgcgtattga    1560
```

```
atatgttggt gaaacctgta cccgtcagat taatgttctg aaagaacagg ttcgtatgat    1620
gctgcataaa gttgttaatc cgctggaaca gctggaactg attgaaattc tgcagcgtct    1680
gggtctgagc tatcattttg aagaagaaat taaacgtatt ctggatggtg tttataataa    1740
tgatcatggt ggtgatacct ggaaagcaga aaatctgtat gcaaccgcac tgaaatttcg    1800
tctgctgcgt cagcatggtt atagcgttag ccaggaagtt tttaatagct ttaaagatga    1860
acgtggtagc tttaaagcat gtctgtgtga agataccaaa ggtatgctga gcctgtatga    1920
agcaagcttt tttctgattg aaggtgaaaa tattctggaa gaagcacgtg attttagcac    1980
caaacatctg gaagaatatg ttaaacagaa taaagaaaaa atctggcaa ccctggttaa     2040 tcatagcctg gaatttccgc tgcattggcg tatgccgcgt ctggaagcac gttggtttat    2100
taatatttat cgtcataatc aggatgttaa tccgattctg ctggaatttg cagaactgga    2160
ttttaatatt gttcaggcag cacatcaggc agatttaaaa caggttagca cctggtggaa    2220
aagcaccggt ctggttgaaa atctgagctt gcacgtgat cgtccggttg aaaatttttt     2280
ttggaccgtt ggtctgattt ttcagccgca gtttggttat tgtcgtcgta tgtttaccaa    2340 agttttttgca ctgattacca ccattgatga tgtttatgat gtttatggta ccctggatga   2400
actggaactg tttaccgatg ttgttgaacg ttgggatatt aatgcaatgg atcagctgcc    2460
ggattatatg aaaatttgtt ttctgaccct gcataatagc gttaatgaaa tggcactgga    2520
taccatgaaa gaacagcgtt ttcatattat taaatatctg aaaaaagcat gggttgatct    2580
gtgtcgttat tatctggttg aagcaaaatg gtatagcaat aaatatcgtc gagcctgca    2640 ggaatatatt gaaaatgcat ggattagcat tggtgcaccg accattctgg ttcatgcata    2700 ttttttttgtt accaatccga ttaccaaaga agcactggat tgtctggaag aatatccgaa   2760
tattattcgt tggagcagca ttattgcacg tctggcagat gatctgggta ccagcaccga    2820
tgaactgaaa cgtggtgatg ttccgaaagc aattcagtgt tatatgaatg aaaccggtgc    2880
aagcgaagaa ggtgcacgtg aatatattaa atatctgatt agcgcaacct ggaaaaaaat    2940
gaataaagat cgtgcagcaa gcagcccgtt tagccatatt tttattgaaa ttgcactgaa    3000
tctggcacgt atggcacagt gtctgtatca gcatggtgat ggtcatggtc tgggtaatcg    3060
tgaaaccaaa gatcgtattc tgagcctgct gattcagccg attccgctga taaagatta    3120 aggatccaaa ctcgagtaag gatctccagg catcaaataa aacgaaaggc tcagtcgaaa    3180
gactgggcct ttcgttttat ctgttgtttg tcggtgaacg ctctctacta gagtcacact    3240
ggctcaccct cgggtgggcc tttctgcgtt tatacctagg gcgttcggct gcggcgagcg    3300
gtatcagctc actcaaaggc ggtaatacgg ttatccacag aatcagggga taacgcagga    3360
aagaacatgt gagcaaaagg ccagcaaaag gccaggaacc gtaaaaaggc cgcgttgctg    3420 gcgttttttcc ataggctccg ccccctgac gagcatcaca aaaatcgacg ctcaagtcag    3480
aggtggcgaa acccgacagg actataaaga taccaggcgt tttcccctgg aagctccctc    3540
gtgcgctctc ctgttccgac cctgccgctt accggatacc tgtccgcctt ctccccttcg    3600
ggaagcgtgg cgctttctca tagctcacgc tgtaggtatc tcagttcggt gtaggtcgtt    3660
cgctccaagc tgggctgtgt gcacgaaccc ccgttcagc cgaccgctg cgccttatcc      3720 ggtaactatc gtcttgagtc aacccggta agacacgact tatcgccact ggcagcagcc     3780
actggtaaca ggattagcag agcgaggtat gtaggcggtg ctacagagtt cttgaagtgg    3840
tggcctaact acggctacac tagaaggaca gtatttggta tctgcgctct gctgaagcca    3900
```

```
gttaccttcg gaaaaagagt tggtagctct tgatccggca acaaaccac cgctggtagc      3960 ggtggttttt ttgtttgcaa gcagcagatt acgcgcagaa aaaaggatc tcaagaagat      4020 cctttgatct tttctacggg gtctgacgct cagtggaacg aaaactcacg ttaagggatt    4080
ttggtcatga ctagtgcttg gattctcacc aataaaaaac gcccggcggc aaccgagcgt    4140
tctgaacaaa tccagatgga gttctgaggt cattactgga tctatcaaca ggagtccaag    4200
cgagctcgta aacttggtct gacagttacc aatgcttaat cagtgaggca cctatctcag    4260
cgatctgtct atttcgttca tccatagttg cctgactccc cgtcgtgtag ataactacga    4320
tacgggaggg cttaccatct ggccccagtg ctgcaatgat accgcgagac ccacgctcac    4380
cggctccaga tttatcagca ataaaccagc cagccggaag ggccgagcgc agaagtggtc    4440
ctgcaacttt atccgcctcc atccagtcta ttaattgttg ccgggaagct agagtaagta    4500
gttcgccagt taatagtttg cgcaacgttg ttgccattgc tacaggcatc gtggtgtcac    4560
gctcgtcgtt tggtatggct tcattcagct ccggttccca acgatcaagg cgagttacat    4620 gatccccat gttgtgcaaa aaagcggtta gctccttcgg tcctccgatc gttgtcagaa    4680
gtaagttggc cgcagtgtta tcactcatgg ttatggcagc actgcataat tctcttactg    4740
tcatgccatc cgtaagatgc ttttctgtga ctggtgagta ctcaaccaag tcattctgag    4800
aatagtgtat gcggcgaccg agttgctctt gcccggcgtc aatacgggat aataccgcgc    4860
cacatagcag aactttaaaa gtgctcatca ttggaaaacg ttcttcgggg cgaaaactct    4920
caaggatctt accgctgttg agatccagtt cgatgtaacc cactcgtgca cccaactgat    4980
cttcagcatc ttttactttc accagcgttt ctgggtgagc aaaaacagga aggcaaaatg    5040
ccgcaaaaaa gggaataagg gcgacacgga aatgttgaat actcatactc ttcctttttc    5100
aatattattg aagcatttat cagggttatt gtctcatgag cggatacata tttgaatgta    5160
tttagaaaaa taaacaaata ggggttccgc gcacatttcc ccgaaaagtg ccacct        5216
```

<210> SEQ ID NO 15
<211> LENGTH: 6139
<212> TYPE: DNA
<213> ORGANISM: Artificial Sequence
<220> FEATURE:
<223> OTHER INFORMATION: pBbE1a-tGPPS2(co)-tMS(co.Qi) plasmid vector

<400> SEQUENCE: 15

```
gacgtcgaca ccatcgaatg gtgcaaaacc tttcgcggta tggcatgata gcgcccggaa      60
gagagtcaat tcagggtggt gaatgtgaaa ccagtaacgt tatacgatgt cgcagagtat    120
gccggtgtct cttatcagac cgtttcccgc gtggtgaacc aggccagcca cgtttctgcg    180
aaaacgcggg aaaaagtgga agcggcgatg gcggagctga attacattcc caaccgcgtg    240
gcacaacaac tggcgggcaa acagtcgttg ctgattggcg ttgccacctc cagtctggcc    300
ctgcacgcgc cgtcgcaaat tgtcgcggcg attaaatctc gcgccgatca actgggtgcc    360
agcgtggtgg tgtcgatggt agaacgaagc ggcgtcgaag cctgtaaagc ggcggtgcac    420
aatcttctcg cgcaacgcgt cagtgggctg atcattaact atccgctgga tgaccaggat    480
gccattgctg tggaagctgc ctgcactaat gttccggcgt tatttcttga tgtctctgac    540
cagacaccca tcaacagtat tattttctcc catgaagacg gtacgcgact gggcgtggag    600
catctggtcg cattgggtca ccagcaaatc gcgctgttag cgggcccatt aagttctgtc    660
tcggcgcgtc tgcgtctggc tggctggcat aaatatctca ctcgcaatca aattcagccg    720
atagcggaac gggaaggcga ctggagtgcc atgtccggtt ttcaacaaac catgcaaatg    780
```

```
ctgaatgagg gcatcgttcc cactgcgatg ctggttgcca acgatcagat ggcgctgggc    840
gcaatgcgcg ccattaccga gtccgggctg cgcgttggtg cggatatctc ggtagtggga    900
tacgacgata ccgaagacag ctcatgttat atcccgccgt taaccaccat caaacaggat    960
tttcgcctgc tggggcaaac cagcgtggac cgcttgctgc aactctctca gggccaggcg   1020
gtgaagggca atcagctgtt gcccgtctca ctggtgaaaa gaaaaaccac cctggcgccc   1080
aatacgcaaa ccgcctctcc ccgcgcgttg gccgattcat taatgcagct ggcacgacag   1140
gtttcccgac tggaaagcgg gcagtgagcg caacgcaatt aatgtaagtt agcgcgaatt   1200
gatctggttt gacagcttat catcgactgc acggtgcacc aatgcttctg cgtcaggca    1260 gccatcggaa gctgtggtat ggctgtgcag gtcgtaaatc actgcataat tcgtgtcgct   1320
caaggcgcac tcccgttctg gataatgttt tttgcgccga catcataacg gttctggcaa   1380
atattctgaa atgagctgtt gacaattaat catccggctc gtataatgtg tggaattgtg   1440
agcggataac aatttcagaa ttcaaaagat cttttaagaa ggagatatac atatggtgga   1500
atttgatttt aacaaatata tggatagcaa agcgatgacc gtgaacgaag cgctgaacaa   1560
agcgattccg ctgcgctatc cgcagaaaat ttatgaaagc atgcgctata gcctgctggc   1620
gggcggcaaa cgcgtgcgcc cggtgctgtg cattgcggcg tgcgaactgg tgggcggcac   1680
cgaagaactg gcgattccga ccgcgtgcgc gattgaaatg attcatacca tgagcctgat   1740
gcatgatgat ctgccgtgca ttgataacga tgatctgcgc gcggcaaac cgaccaacca   1800 taaaattttt ggcgaagata ccgcggtgac cgcgggcaac gcgctgcata gctatgcgtt   1860
tgaacatatt gcggtgagca ccagcaaaac cgtgggcgcg gatcgcattc tgcgcatggt   1920
gagcgaactg ggccgcgcga ccggcagcga aggcgtgatg ggcggccaga tggtggatat   1980
tgcgagcgaa ggcgatccga gcattgatct gcagaccctg gaatggattc atattcataa   2040
aaccgcgatg ctgctggaat gcagcgtggt gtgcggcgcg attattggcg gcgcgagcga   2100
aattgtgatt gaacgcgcgc gccgctatgc gcgctgcgtg ggcctgctgt tcaggtggt    2160 ggatgatatt ctggatgtga ccaaaagcag cgatgaactg ggcaaaaccg cgggcaaaga   2220
tttaattagc gataaagcga cctatccgaa actgatgggc ctggaaaaag cgaaagaatt   2280
tagcgatgaa ctgctgaacc gcgcgaaagg cgaactgagc tgctttgatc cggtgaaagc   2340
ggcgccgctg ctgggcctgg cggattatgt ggcgtttcgc cagaactaag gatcttttaa   2400
gaaggagata tacatatgcg tcgtagcgca aattatcagc cgagcatttg gaatcatgat   2460
tatattgaaa gcctgcgtat tgaatatgtt ggtgaaacct gtacccgtca gattaatgtt   2520
ctgaaagaac aggttcgtat gatgctgcat aaagttgtta atccgctgga acagctggaa   2580
ctgattgaaa ttctgcagcg tctgggtctg agctatcatt ttgaagaaga aattaaacgt   2640
attctggatg gtgtttataa taatgatcat ggtggtgata cctggaaagc agaaaatctg   2700
tatgcaaccg cactgaaatt tcgtctgctg cgtcagcatg gttatagcgt tagccaggaa   2760
gtttttaata gctttaaaga tgaacgtggt agctttaaag catgtctgtg tgaagatacc   2820
aaaggtatgc tgagcctgta tgaagcaagc ttttttctga ttgaaggtga aaatattctg   2880
gaagaagcac gtgattttag caccaaacat ctggaagaat atgttaaaca gaataaagaa   2940
aaaaatctgg caaccctggt taatcatagc ctggaatttc cgctgcattg gcgtatgccg   3000
cgtctggaag cacgttggtt tattaatatt tatcgtcata atcaggatgt taatccgatt   3060
ctgctggaat ttgcagaact ggattttaat attgttcagg cagcacatca ggcagattta   3120
```

```
aaacaggtta gcacctggtg gaaaagcacc ggtctggttg aaaatctgag ctttgcacgt    3180
gatcgtccgg ttgaaaattt tttttggacc gttggtctga ttttcagcc gcagtttggt    3240
tattgtcgtc gtatgtttac caaagttttt gcactgatta ccaccattga tgatgtttat    3300
gatgtttatg gtaccctgga tgaactggaa ctgtttaccg atgttgttga acgttgggat    3360
attaatgcaa tggatcagct gccggattat atgaaaattt gttttctgac cctgcataat    3420
agcgttaatg aaatggcact ggataccatg aaagaacagc gttttcatat tattaaaatat    3480
ctgaaaaaag catgggttga tctgtgtcgt tattatctgg ttgaagcaaa atggtatagc    3540
aataaatatc gtccgagcct gcaggaatat attgaaaatg catggattag cattggtgca    3600
ccgaccattc tggttcatgc atattttttt gttaccaatc cgattaccaa agaagcactg    3660
gattgtctgg aagaatatcc gaatattatt cgttggagca gcattattgc acgtctggca    3720
gatgatctgg gtaccagcac cgatgaactg aaacgtggtg atgttccgaa agcaattcag    3780
tgttatatga tgaaaccgg tgcaagcgaa gaaggtgcac gtgaatatat taaatatctg    3840
attagcgcaa cctggaaaaa aatgaataaa gatcgtgcag caagcagccc gtttagccat    3900
atttttattg aaattgcact gaatctggca cgtatggcac agtgtctgta tcagcatggt    3960
gatggtcatg gtctgggtaa tcgtgaaacc aaagatcgta ttctgagcct gctgattcag    4020
ccgattccgc tgaataaaga ttaaggatcc aaactcgagt aaggatctcc aggcatcaaa    4080
taaaacgaaa ggctcagtcg aaagactggg cctttcgttt tatctgttgt ttgtcggtga    4140
acgctctcta ctagagtcac actggctcac cttcgggtgg gcctttctgc gtttatacct    4200
agggcgttcg gctgcggcga gcggtatcag ctcactcaaa ggcggtaata cggttatcca    4260
cagaatcagg ggataacgca ggaaagaaca tgtgagcaaa aggccagcaa aaggccagga    4320
accgtaaaaa ggccgcgttg ctggcgtttt tccataggct ccgcccccct gacgagcatc    4380
acaaaaatcg acgctcaagt cagaggtggc gaaacccgac aggactataa agataccagg    4440
cgtttccccc tggaagctcc ctcgtgcgct ctcctgttcc gaccctgccg cttaccggat    4500
acctgtccgc ctttctccct tcgggaagcg tggcgctttc tcatagctca cgctgtaggt    4560
atctcagttc ggtgtaggtc gttcgctcca agctgggctg tgtgcacgaa ccccccgttc    4620
agcccgaccg ctgcgcctta tccggtaact atcgtcttga gtccaacccg gtaagacacg    4680
acttatcgcc actggcagca gccactggta acaggattag cagagcgagg tatgtaggcg    4740
gtgctacaga gttcttgaag tggtggccta actacggcta cactagaagg acagtatttg    4800
gtatctgcgc tctgctgaag ccagttacct tcggaaaaag agttggtagc tcttgatccg    4860
gcaaacaaac caccgctggt agcggtggtt tttttgtttg caagcagcag attacgcgca    4920
gaaaaaagg atctcaagaa gatcctttga tcttttctac ggggtctgac gctcagtgga    4980
acgaaaactc acgttaaggg attttggtca tgactagtgc ttggattctc accaataaaa    5040
aacgcccggc ggcaaccgag cgttctgaac aaatccagat ggagttctga ggtcattact    5100
ggatctatca acaggagtcc aagcgagctc gtaaacttgg tctgacagtt accaatgctt    5160
aatcagtgag gcacctatct cagcgatctg tctatttcgt tcatccatag ttgcctgact    5220
ccccgtcgtg tagataacta cgatacggga gggcttacca tctggcccca gtgctgcaat    5280
gataccgcga gacccacgct caccggctcc agatttatca gcaataaacc agccagccgg    5340
aagggccgag cgcagaagtg gtcctgcaac tttatccgcc tccatccagt ctattaattg    5400
ttgccgggaa gctagagtaa gtagttcgcc agttaatagt ttgcgcaacg ttgttgccat    5460
tgctacaggc atcgtggtgt cacgctcgtc gtttggtatg gcttcattca gctccggttc    5520
```

```
ccaacgatca aggcgagtta catgatcccc catgttgtgc aaaaaagcgg ttagctcctt    5580
cggtcctccg atcgttgtca gaagtaagtt ggccgcagtg ttatcactca tggttatggc    5640
agcactgcat aattctctta ctgtcatgcc atccgtaaga tgcttttctg tgactggtga    5700
gtactcaacc aagtcattct gagaatagtg tatgcggcga ccgagttgct cttgcccggc    5760
gtcaatacgg gataataccg cgccacatag cagaacttta aaagtgctca tcattggaaa    5820
acgttcttcg gggcgaaaac tctcaaggat cttaccgctg ttgagatcca gttcgatgta    5880
acccactcgt gcacccaact gatcttcagc atcttttact ttcaccagcg tttctgggtg    5940
agcaaaaaca ggaaggcaaa atgccgcaaa aaagggaata agggcgacac ggaaatgttg    6000
aatactcata ctcttccttt ttcaatatta ttgaagcatt tatcagggtt attgtctcat    6060
gagcggatac atatttgaat gtatttagaa aaataaacaa atagggttc cgcgcacatt    6120 tccccgaaaa gtgccacct                                                6139
```